(12) United States Patent
Weiss et al.

(10) Patent No.: US 9,109,150 B2
(45) Date of Patent: Aug. 18, 2015

(54) FAST RECOVERY OF THIXOTROPY BY ORGANOGELS WITH LOW MOLECULAR WEIGHT GELATORS

(75) Inventors: Richard G. Weiss, Bethesda, MD (US); Ajaya Mallia Viswanatha Mallya, Washington, DC (US)

(73) Assignee: GEORGETOWN UNIVERSITY, Washington, DC (US)

(*) Notice: Subject to any disclaimer, the term of this patent is extended or adjusted under 35 U.S.C. 154(b) by 604 days.

(21) Appl. No.: 13/043,200

(22) Filed: Mar. 8, 2011

(65) Prior Publication Data
US 2011/0251294 A1 Oct. 13, 2011

Related U.S. Application Data

(60) Provisional application No. 61/282,609, filed on Mar. 8, 2010, provisional application No. 61/346,388, filed on May 19, 2010.

(51) Int. Cl.
| | |
|---|---|
| A61K 47/12 | (2006.01) |
| C09K 3/32 | (2006.01) |
| A23L 1/05 | (2006.01) |
| A61K 8/04 | (2006.01) |
| A61K 8/42 | (2006.01) |
| A61K 8/97 | (2006.01) |
| A61K 47/18 | (2006.01) |
| A61Q 19/00 | (2006.01) |
| C07C 215/08 | (2006.01) |
| C07C 235/06 | (2006.01) |
| A61K 9/06 | (2006.01) |

(52) U.S. Cl.
CPC ... *C09K 3/32* (2013.01); *A23L 1/05* (2013.01); *A61K 8/042* (2013.01); *A61K 8/42* (2013.01); *A61K 8/97* (2013.01); *A61K 47/18* (2013.01); *A61Q 19/00* (2013.01); *C07C 215/08* (2013.01); *C07C 235/06* (2013.01); *A61K 9/06* (2013.01); *A61K 2800/48* (2013.01)

(58) Field of Classification Search
CPC .......... C09K 3/32; A61K 8/042; A61K 8/42; A61K 8/97; A61K 9/06; A61K 2800/48; A61Q 19/00; C07C 15/08; C07C 235/06
USPC ............. 516/27, 102; 564/303, 304, 503
See application file for complete search history.

(56) References Cited

U.S. PATENT DOCUMENTS

| | | | | | |
|---|---|---|---|---|---|
| 1,836,048 | A | * | 12/1931 | Somerville | 564/463 |
| 2,558,666 | A | * | 6/1951 | Vander Wal | 516/73 |
| 2,712,558 | A | * | 7/1955 | Vander Wal et al. | 564/503 |
| 2,818,434 | A | * | 12/1957 | Vander Wal J et al. | 564/292 |
| 2,837,170 | A | * | 6/1958 | Francis et al. | 252/88.2 |
| 3,177,254 | A | * | 4/1965 | Rogier et al. | 564/503 |
| 3,969,087 | A | * | 7/1976 | Saito et al. | 516/102 |
| 4,413,138 | A | * | 11/1983 | Gladfelter et al. | 549/551 |
| 4,502,975 | A | | 3/1985 | Kobayashi | |
| 4,790,961 | A | * | 12/1988 | Weiss et al. | 516/108 |
| 4,829,142 | A | * | 5/1989 | Gonzalez et al. | 528/111 |
| 4,970,961 | A | | 11/1990 | Hestrom | |
| 5,607,972 | A | * | 3/1997 | Motley | 514/558 |
| 5,892,116 | A | * | 4/1999 | Weiss et al. | 564/281 |
| 6,217,889 | B1 | * | 4/2001 | Lorenzi et al. | 424/401 |
| 2004/0223994 | A1 | | 11/2004 | Emslie | |
| 2004/0224854 | A1 | | 11/2004 | Boudreau | |
| 2011/0251294 | A1 | | 10/2011 | Weiss | |
| 2012/0129947 | A1 | * | 5/2012 | Dagan et al. | 564/503 |
| 2012/0136074 | A1 | * | 5/2012 | Weiss et al. | 516/102 |

OTHER PUBLICATIONS

Habel et al, "1-Phenylethyl isocyanate is a powerful reagent for the chiral analysis of secondary alcohols and hydroxy fatty acids with remote stereogenic centres", Journal of Chromatography A, vol. 1165, Issues 1-2, (Sep. 21, 2007) pp. 182-190.*
P. Terech, V. Rodriguez, J. D. Barnes, G. B. McKenna, "Organogels and Aerogels of Racemic and Chiral 12-Hydroxyoctadecanoic Acid" Langmuir, vol. 10, Issue 10 (Oct. 1994) pp. 3373-3918.*
Pierre Terech and Richard G. Weiss, "Low Molecular Mass Gelators of Organic Liquids and the Properties of Their Gels", vol. 97, Issue 8, pp. 3133-3159 (Dec. 1997; Web: Dec. 18, 1997) DOI: 10.1021/cr9700282.*
Taro Tachibana, Tomoko Mori & Kayako Hori, "New type of twisted mesophase in jellies and solid films of chiral 12-hydroxyoctadecanoic acid", Nature, vol. 278 No. 5704 pp. 493-579 (Apr. 5, 1979) doi:10.1038/278578a0.*
Entire patent prosecution history of U.S. Appl. No. 13/218,953, filed Aug. 26, 2011, entitled, "Systems and Methods Employing Low Molecular Weight Gelators for Crude Oil, Petroleum Product or Chemical Spill Containment and Remediation."
International Preliminary Report on Patentability for International Application No. PCT/US2011/001505 issued Feb. 26, 2013.
International Search Report for International Application No. PCT/US2011/001505 mailed Jan. 19, 2012.

* cited by examiner

*Primary Examiner* — Daniel S Metzmaier
(74) *Attorney, Agent, or Firm* — RatnerPrestia

(57) ABSTRACT

Low molecular weight gelators, methods of making such gelators, organogels comprising such gelators and methods of using such organogels are described. In exemplary methods, the gelators can be used in a variety of applications including the delivery of pharmaceutical active pharmaceutical ingredients, in food, cosmetics and consumer products, and in containing the unexpected release of chemical that occur for example in spills.

2 Claims, 28 Drawing Sheets

FIG. 1  Representation of the Design of LMOGs with Increasing Complexity

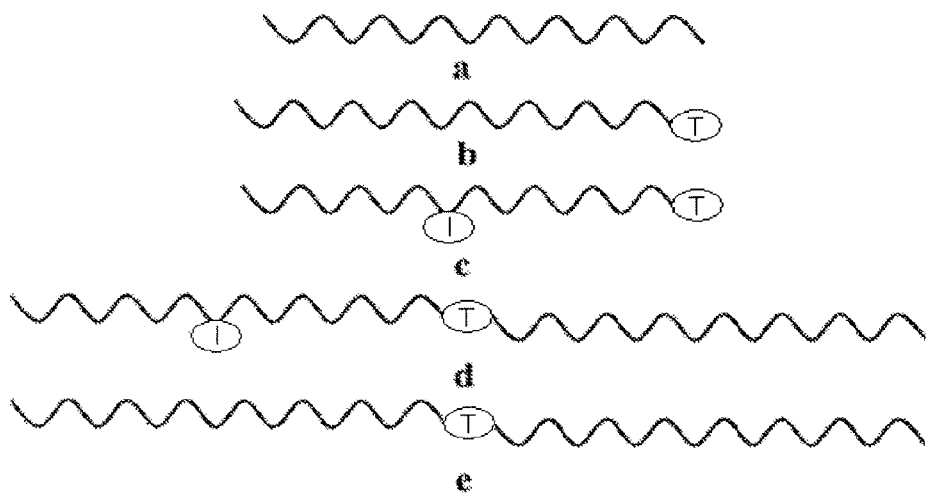

Starting from  (a) an n-alkane gelator and
changing to    (b) an n-alkane with a terminal functional group (T),
               (c) an n-alkane with a terminal and an "interior" pendant functional group (I),
               (d) an n-alkane with two functional groups, including an alkyl chain on the terminal functionality, and
               (e) an n-alkane with terminal functionality to which an alkyl group has been appended.

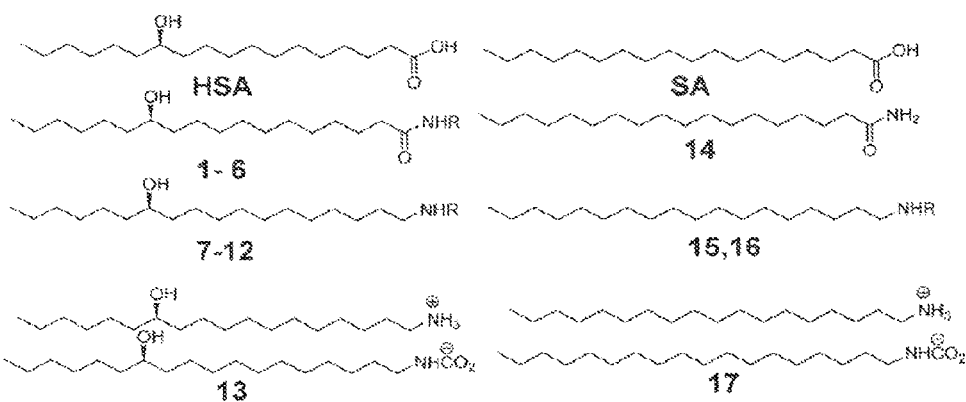

FIG. 2  Structures of LMOGs derived from HSA and those lacking a hydroxyl group from SA upon which comparisons are made for *1*, *7*, and *15* (R = H); for *2* and *8*(R = CH$_3$); for *3* and *9*(R = C$_2$H$_5$); for *4* and *10* (R = C$_3$H$_7$); for *5* and *11*(R = C$_4$H$_9$); for *6*,*12*, and *16* (R = C$_{18}$H$_{37}$); and for *13* and *17*.

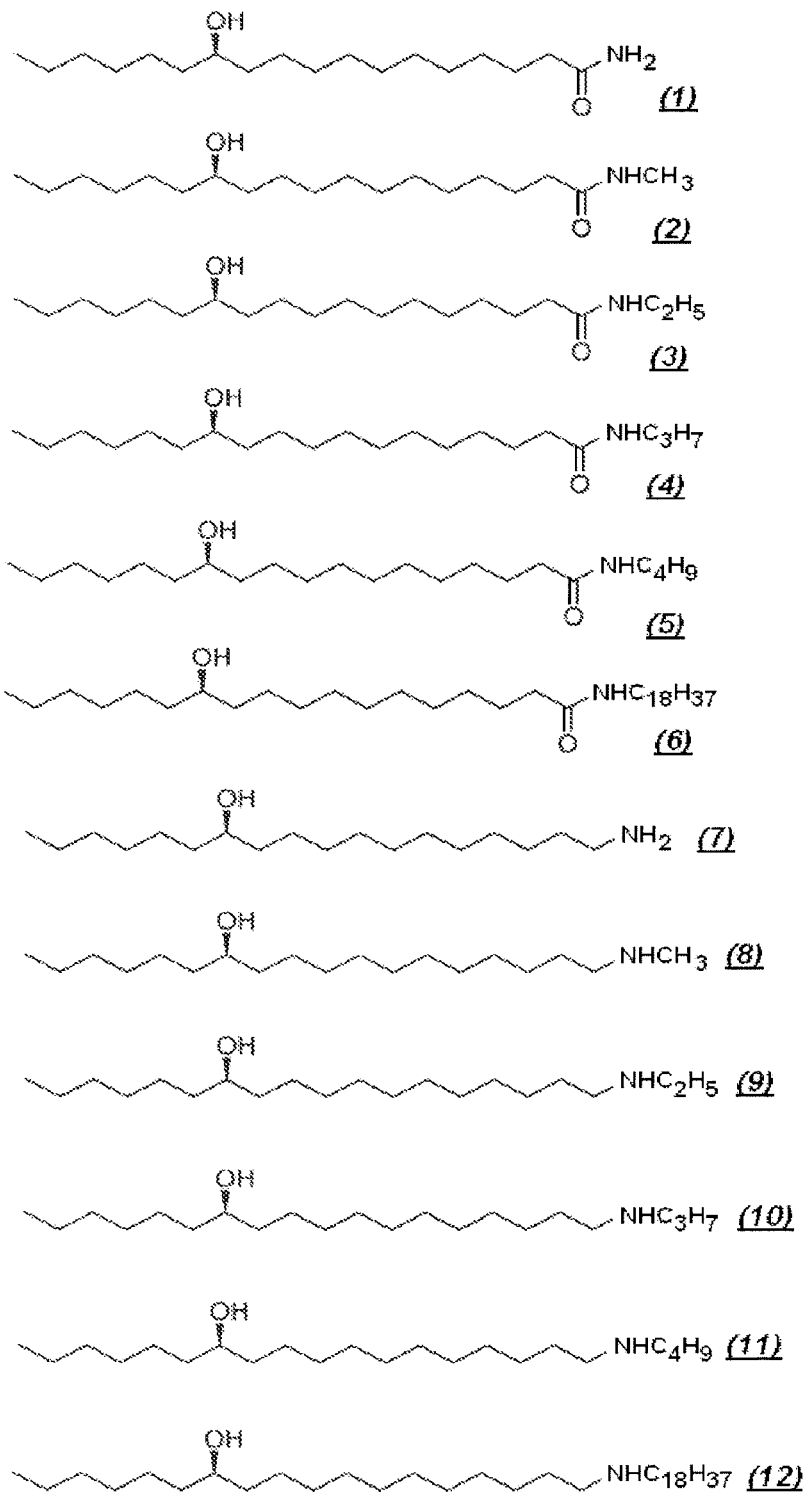
FIG. 3  Chemical Structures of Compound *1 - 12*

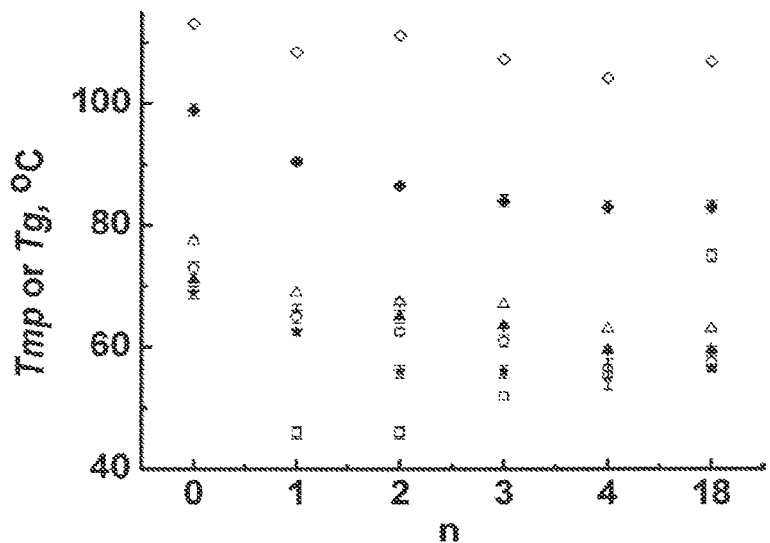

FIG. 4  Plots of the melting points ($T_{mp}$) of the neat amide gelators (1-6) (◇) or the $T_g$ values of their gels with various liquids versus $n$, the number of carbon atoms in their N-alkyl chains: 2 wt % gel in silicone oil (◆), 5 wt % gel in CCl₄ (Δ), 5 wt % gel in benzene (□), 5 wt % gel in toluene (▲), 5 wt % gel in chlorobenzene (★), and 2 wt % gel in DMSO (□). Temperature ranges of vertical bars indicate when the initial and final portions of an inverted gel sample fell on being heated slowly.

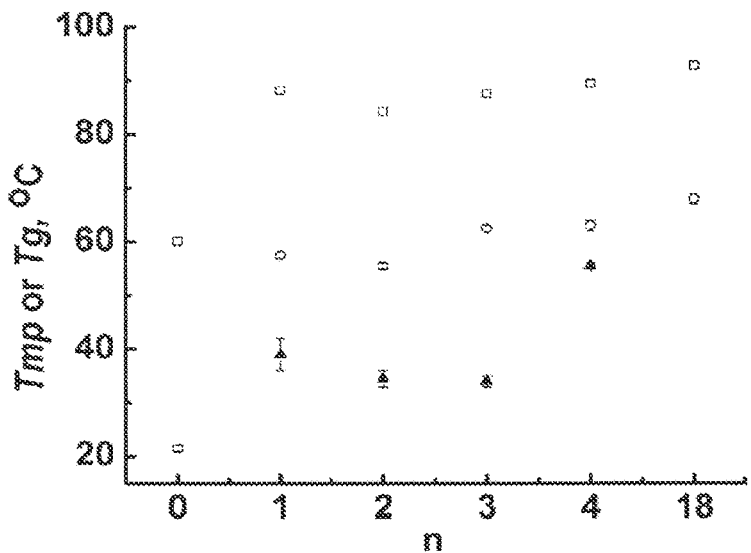

FIG. 5  Plots of the melting points ($T_{mp}$) of the neat amine gelators (7-12) (□) or the $T_g$ values of their gels with various liquids versus $n$, the number of carbon atoms in their N-alkyl chains: 2 wt % gel in silicone oil (○) and 2 wt % gel in DMSO (▲). Temperature ranges of vertical bars refer to when the initial and final portions of a gel sample fell on being heated slowly; the absence of a space bar indicates that the range was smaller than the symbol.

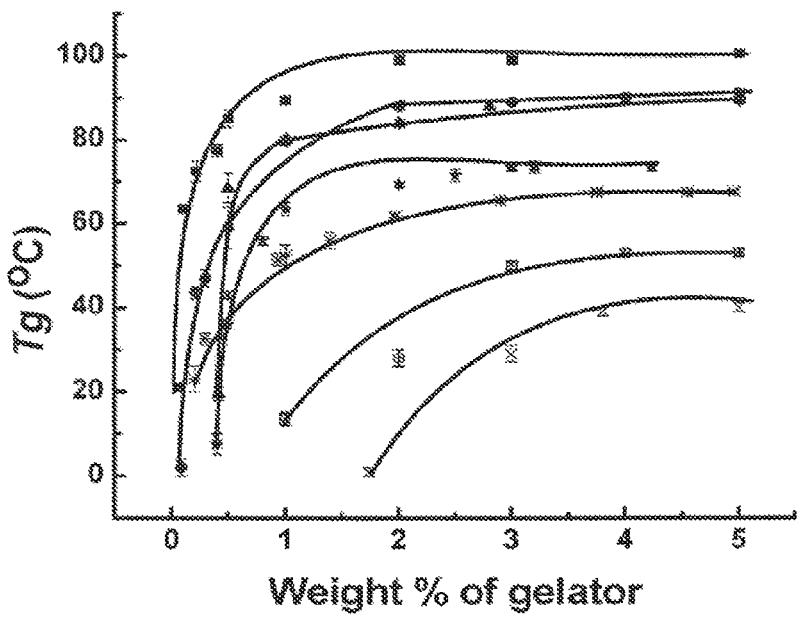

FIG. 6  $T_g$ values of silicone oil gels as a function of concentration of 1 (■), 4 (●), 6 (▲), 7 (▦), 10 (*), 12 (★), and 13 (×). The lines have no physical meaning; they are included to observe trends. Temperature ranges of vertical bars refer to when the initial and final portions of a gel sample fell on being heated slowly.

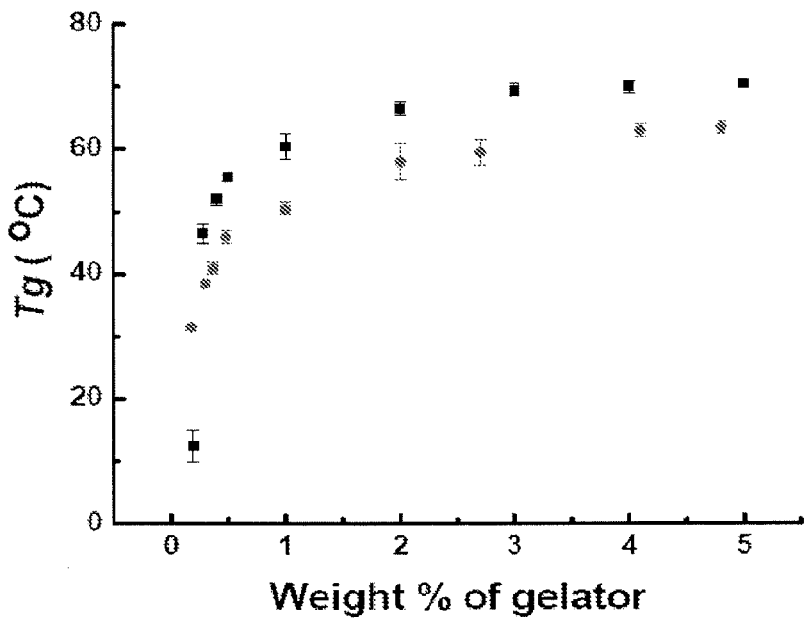

FIG. 7  Tg values of toluene gels as a function of concentration of 1 (box) or 4 (circle). Temperature ranges are between the initial and final falling of portions of each gel.

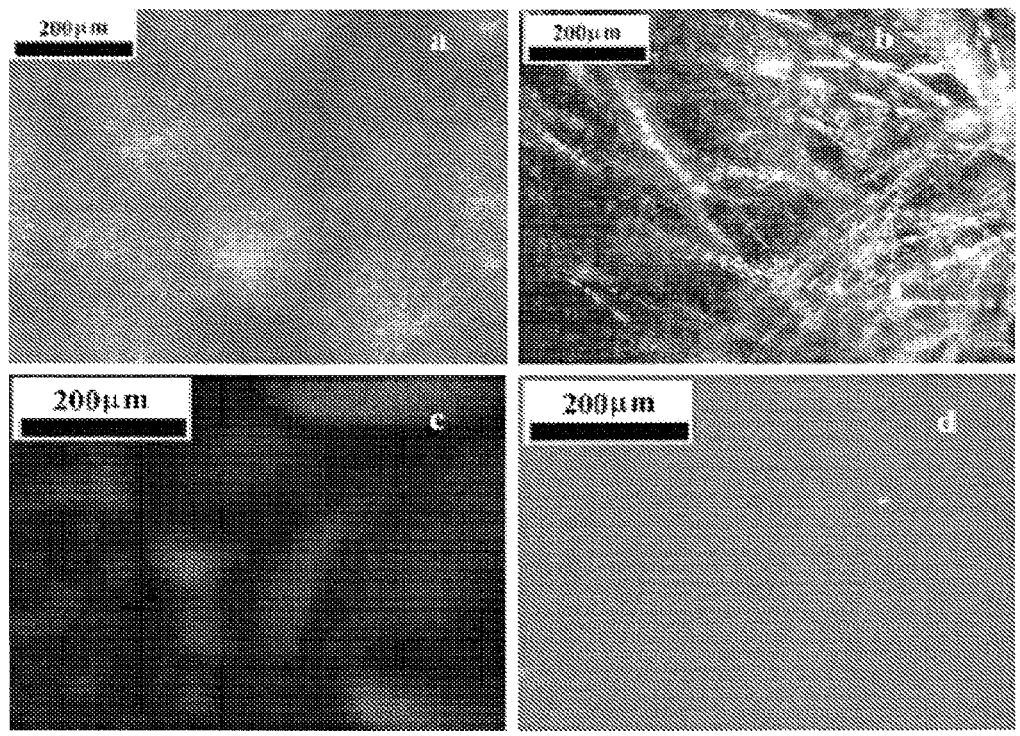

FIG. 8  Polarizing optical micrographs at 24 °C of 2 wt % 1 in (a, b) silicone oil and (c, d) toluene gels prepared by (a, c) fast-cooling and (b, d) slow-cooling protocols. Both silicone oil micrographs show spherulitic textures.

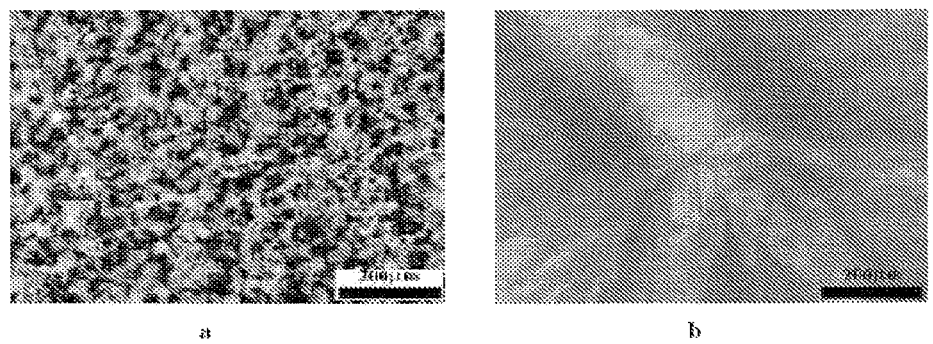

FIG. 9  Polarizing optical micrographs at 24 °C of gels of 2 wt % 4 in decane prepared by (a) fast-cooling and (b) slow-cooling protocols. The images were taken with a full-wave plate.

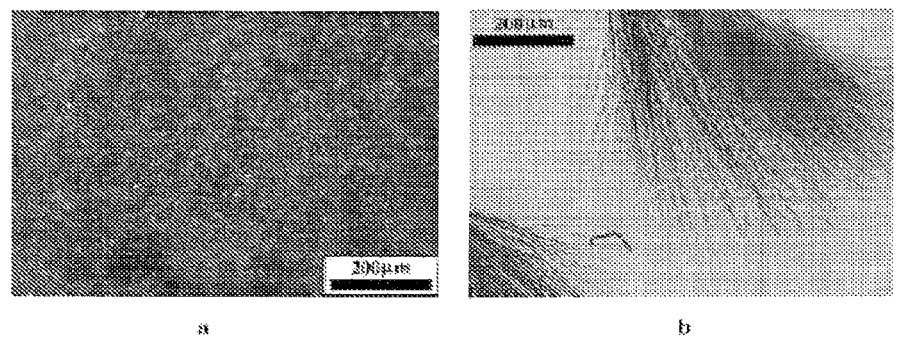

FIG. 10  Polarizing optical micrographs at 24 °C of gels of 2 wt % *4* in CCl₄ prepared by (a) fast-cooling and (b) slow-cooling protocols. The image of the sample prepared by the slow-cooling protocol was taken with a full-wave plate.

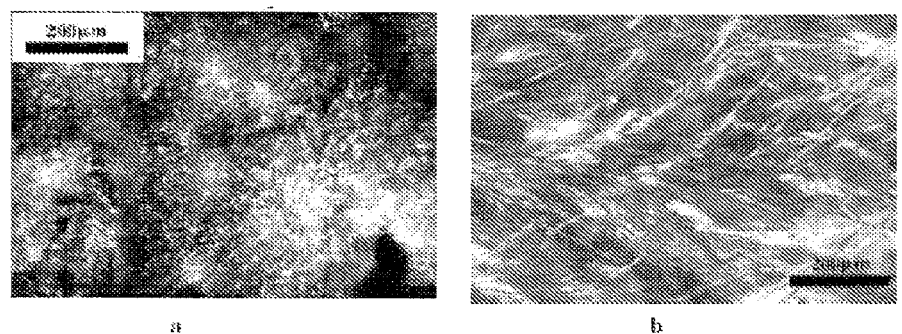

FIG. 11  Polarizing optical micrographs (24 °C) of gels of 2 wt % *4* in DMSO prepared by (a) fast-cooling and (b) slow-cooling protocols.

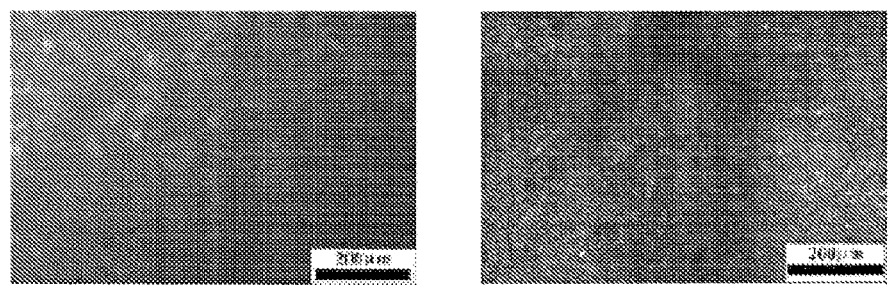

FIG. 12  Polarizing optical micrographs (24 °C) of gels of 2 wt % *4* in toluene prepared by (a) fast-cooling and (b) slow-cooling protocols.

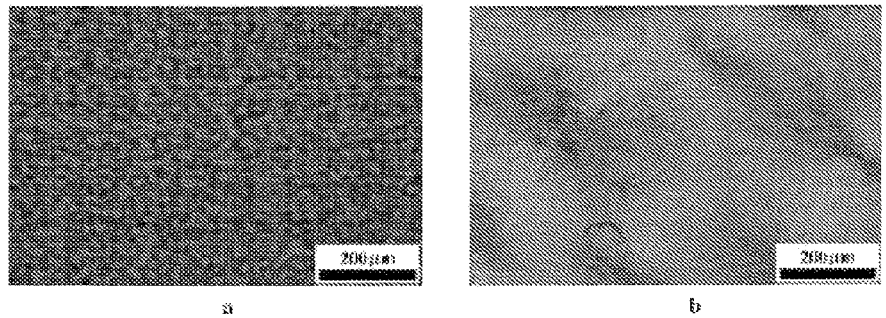

FIG. 13 Polarizing optical micrographs (24 °C) of gels of 2 wt % 4 in silicone oil prepared by (a) fast-cooling and (b) slow-cooling protocols. The images were taken with a full-wave plate.

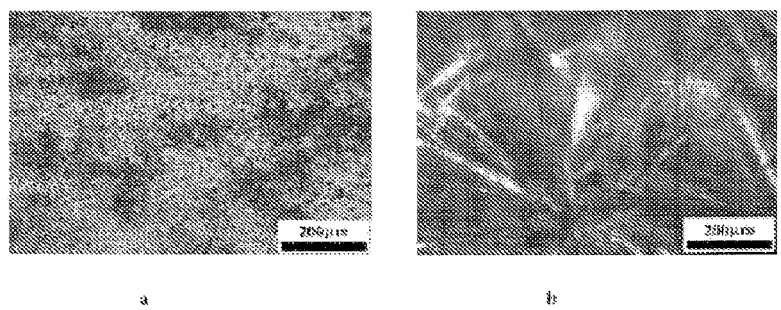

FIG. 14 Polarizing optical micrographs (24 °C) of gels of 2 wt % 6 in decane prepared by (a) fast-cooling and (b) slow-cooling protocols. The image of the sample prepared by the slow-cooling protocol was taken with a full-wave plate.

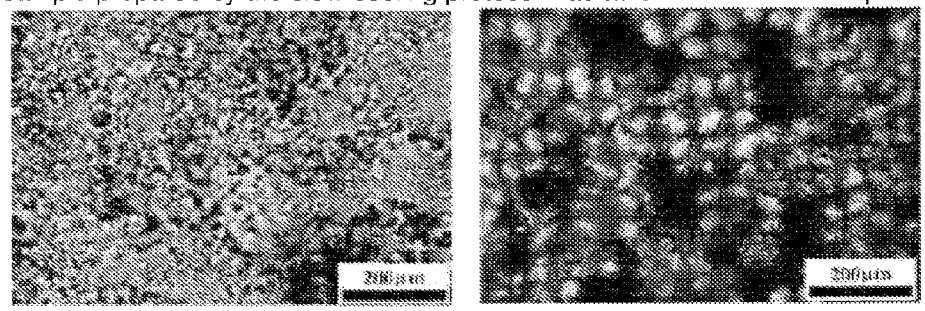

FIG. 15 Polarizing optical micrographs (24 °C) of gels of 2 wt % 6 in CCl$_4$ prepared by (a) fast-cooling and (b) slow-cooling protocols. The image of the sample prepared by the fast-cooling protocol was taken with a full-wave plate.

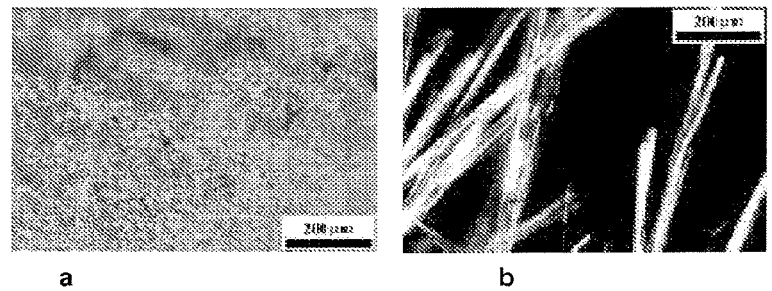

FIG. 16 Polarizing optical micrographs (24 °C) of gels of 2 wt % 6 in DMSO prepared by (a) fast-cooling and (b) slow-cooling protocols. The image of the sample prepared by the fast-cooling protocol was taken with a full-wave plate.

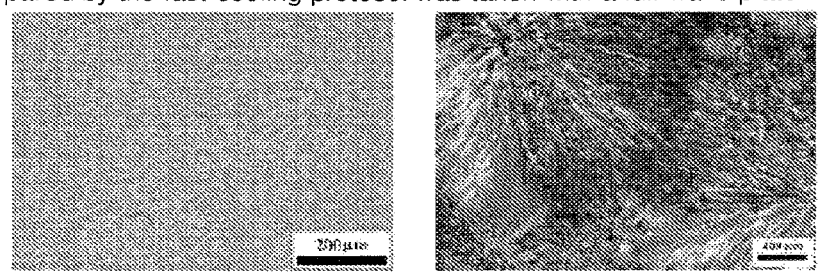

FIG. 17 Polarizing optical micrographs (24 °C) of gels of 2 wt % 6 in silicone oil prepared by (a) fast-cooling and (b) slow-cooling protocols. The images were taken with a full-wave plate.

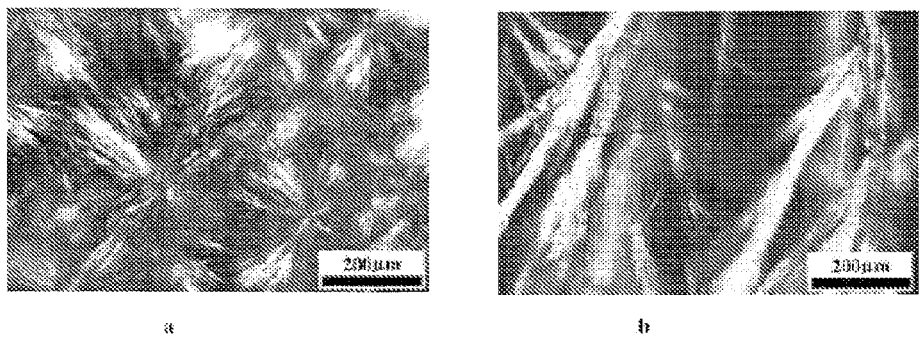

FIG. 18 Polarizing optical micrographs (24 °C) of gels of 2 wt % 10 in $CCl_4$ prepared by (a) fast-cooling and (b) slow-cooling protocols.

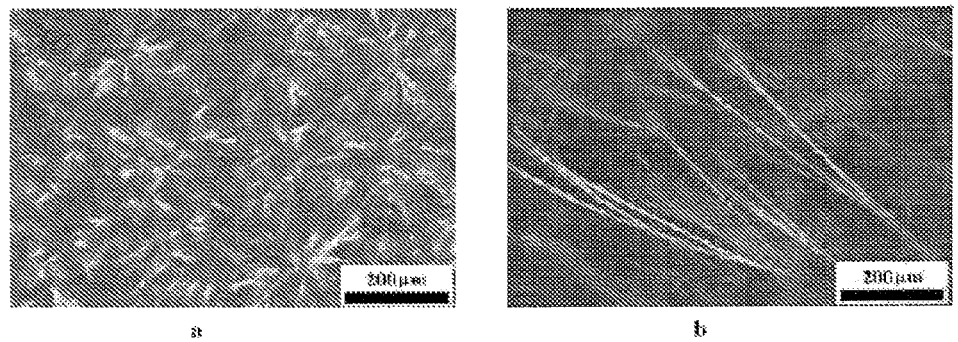
FIG. 19  Polarizing optical micrographs (24 °C) of gels of 2 wt % *10* in decane prepared by (a) fast-cooling and (b) slow-cooling protocols.
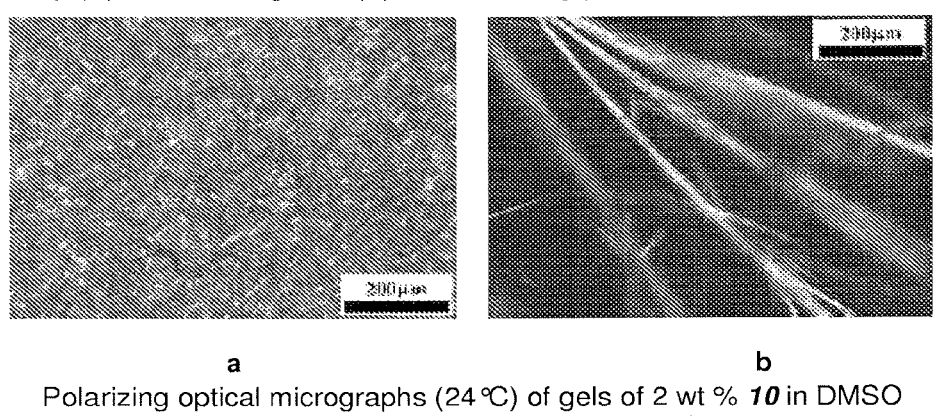
FIG. 20  Polarizing optical micrographs (24 °C) of gels of 2 wt % *10* in DMSO prepared by (a) fast-cooling and (b) slow-cooling protocols.
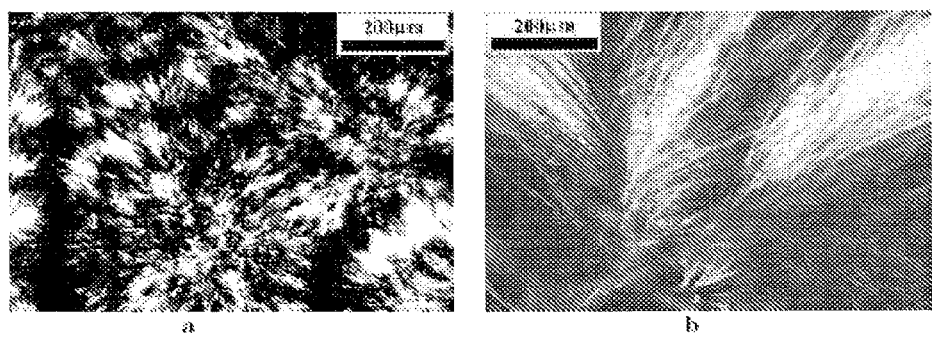
FIG. 21  Polarizing optical micrographs (24 °C) of gels of 2 wt % *10* in toluene prepared by (a) fast-cooling and (b) slow-cooling protocols.

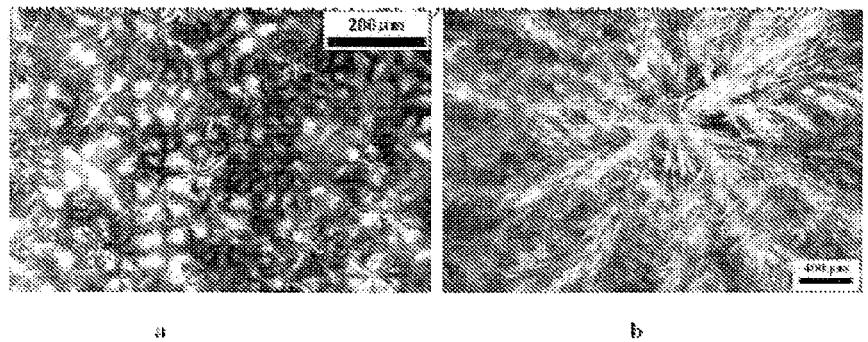

FIG. 22  Polarizing optical micrographs (24 °C) of gels of 2 wt % *10* in silicone oil prepared by (a) fast-cooling and (b) slow-cooling.

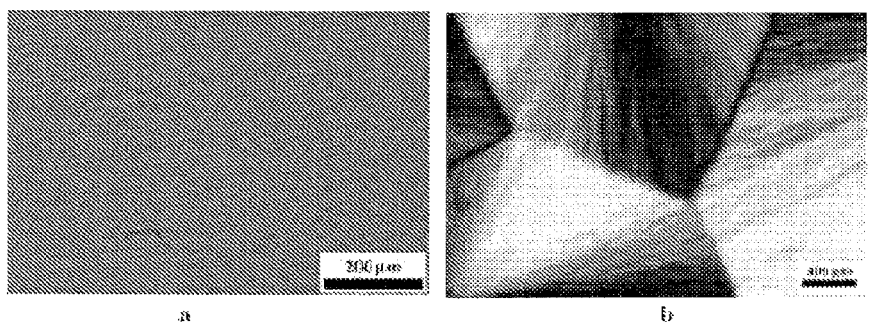

FIG. 23  Polarizing optical micrographs (24 °C) of gels of 2 wt % *12* in silicone oil prepared by (a) fast-cooling and (b) slow-cooling protocols. The images were taken with a full-wave plate.

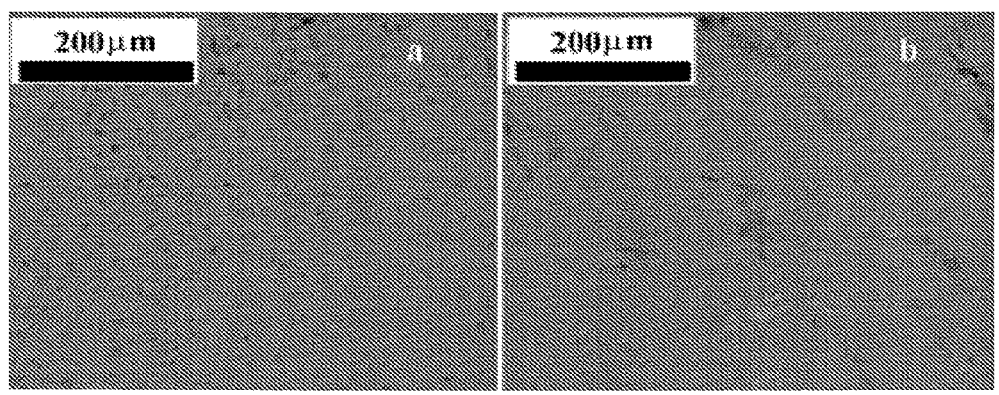

FIG. 24  Polarizing optical micrographs at 24 °C of gels of 0.42 wt % *6* in silicone oil prepared by (a) fast-cooling and (b) slow-cooling protocols. The images were taken with a full-wave plate.

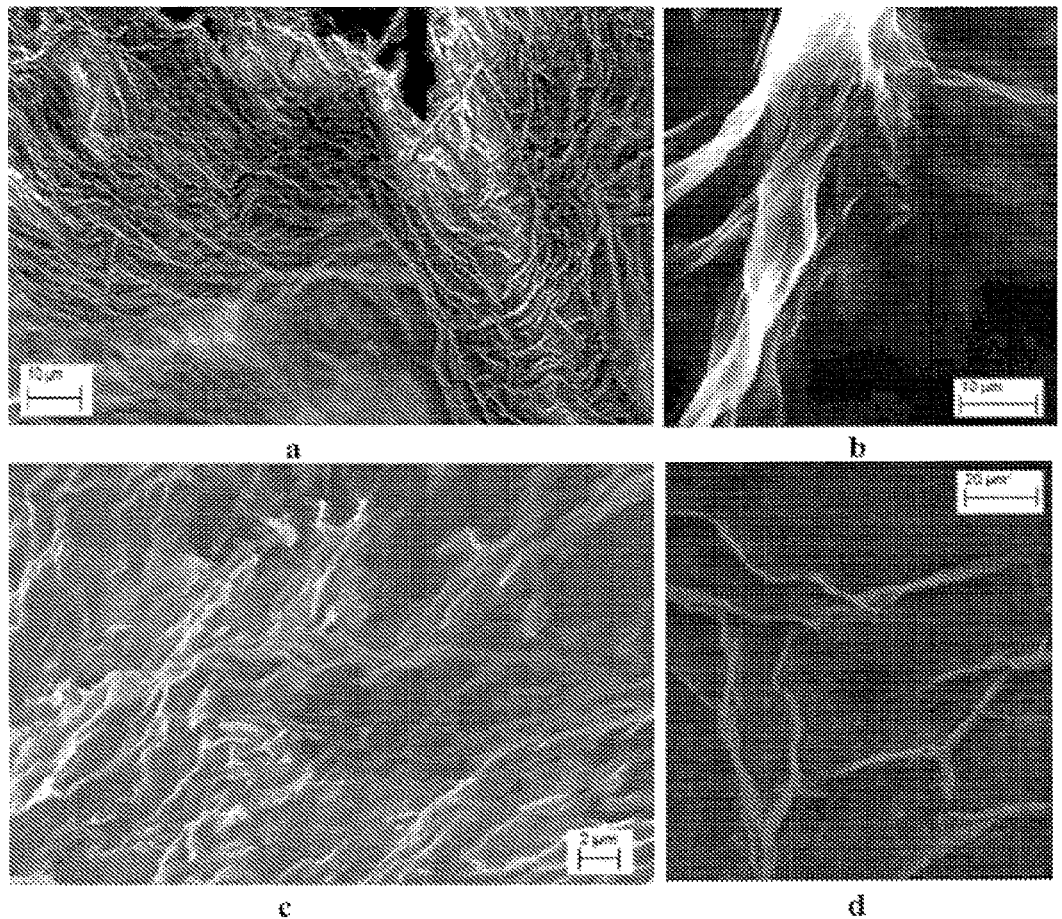
FIG. 25 SEM images of xerogels prepared from (a) 2.0 wt % 1 in CCl$_4$, (b) 0.5 wt % 1 in CCl$_4$, (c) 2.0 wt % 1 in chlorobenzene, and (d) 0.5 wt % 1 in chlorobenzene. Scale bars are 10, 10, 2, and 20 μm in a-d, respectively.

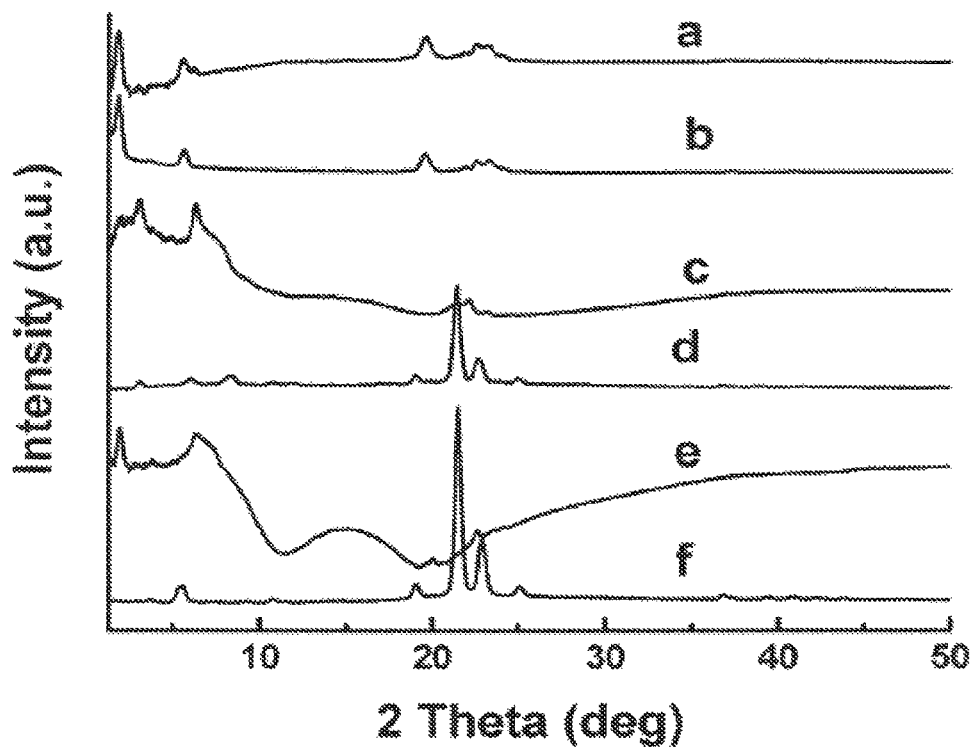
FIG. 26 Vertically offset XRD patterns at 24 °C: (a) 4.8 wt % *1* in silicone oil gel after solvent subtraction; (b) neat *1*; (c) 5.2 wt % *4* in silicone oil gel after solvent subtraction; (d) neat *4*; (e) 5.0 wt % *6* in silicone oil gel after solvent subtraction; and (f) neat *6*.

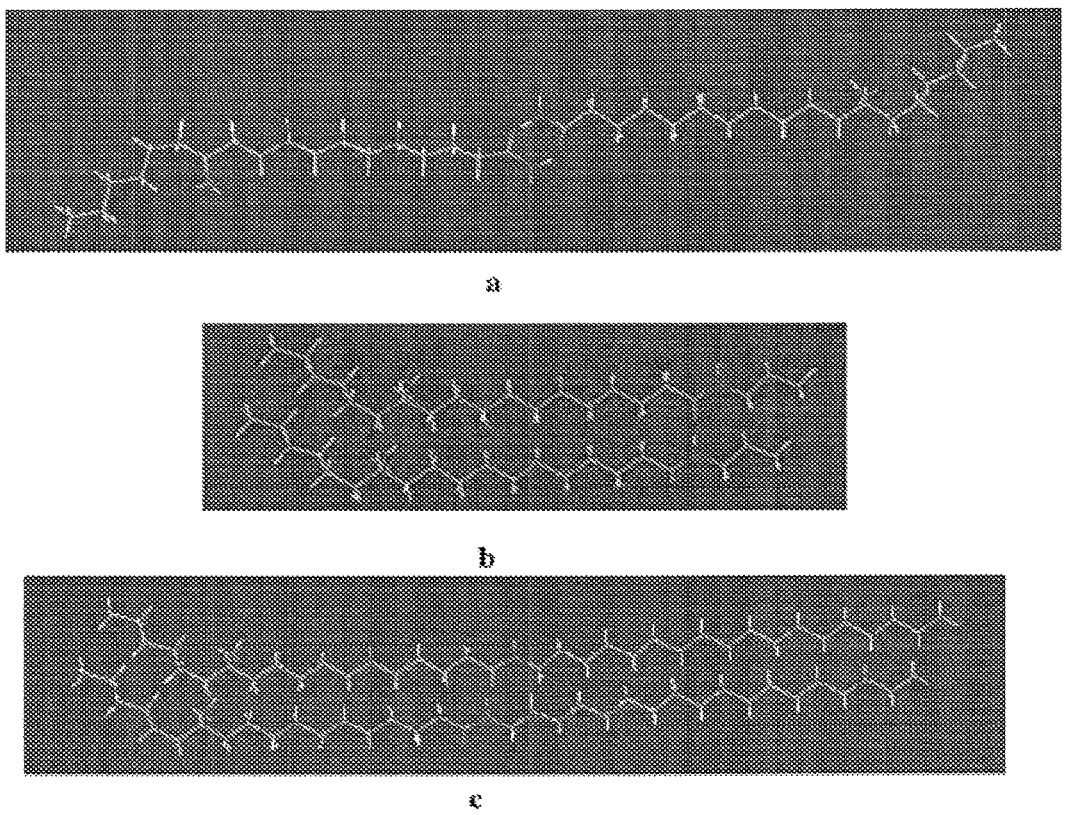
FIG. 27 Proposed packing arrangements of gelator molecules in gel aggregates: (a) *1* (calculated molecular length of dimeric unit = 52.8 Å), (b) *4* (calculated molecular length = 31.1 Å), and (c) *6* (calculated molecular length = 50.3 Å) from molecular mechanics (MM2) calculations.

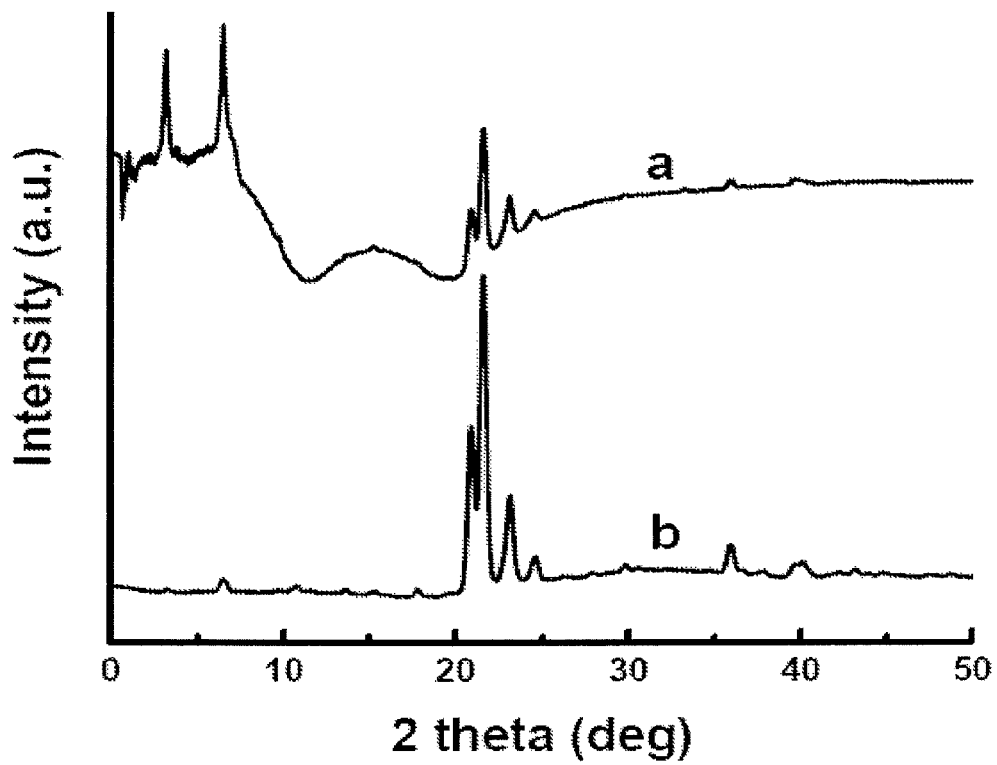
FIG. 28 X-ray diffractograms of 1-(propylamino)octadecan-12-ol (*10*) at 24 °C: (a) 4.8 wt % gel in silicone oil (after subtracting from neat silicone oil diffractogram), (b) neat powder.

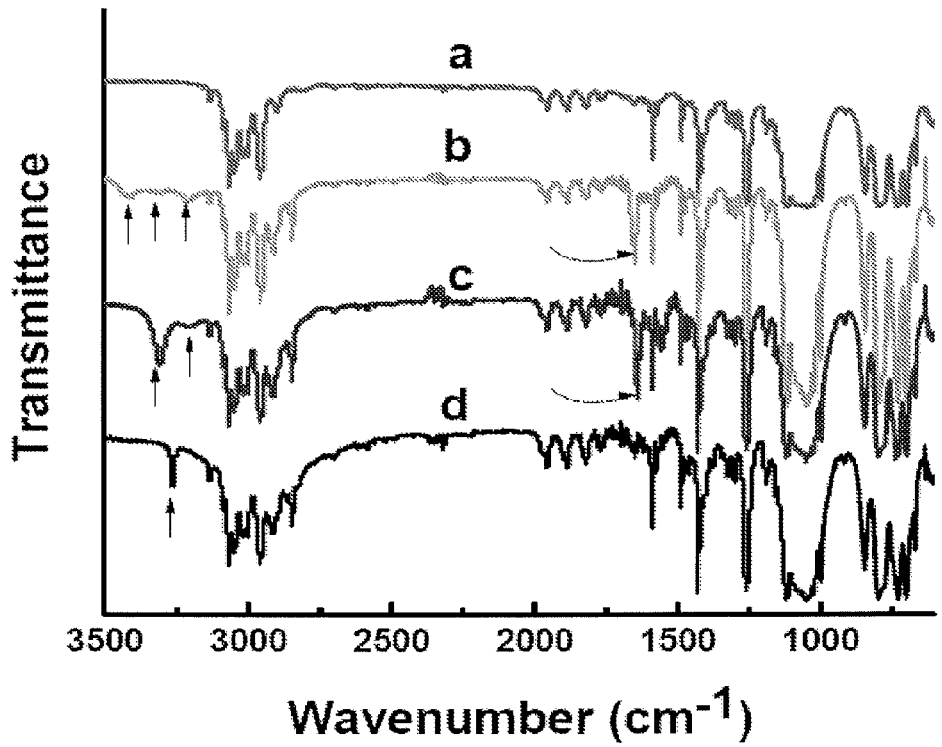

FIG. 29 IR spectra of (a) neat silicone oil, (b) a 5 wt % *1* in silicone oil gel (arrows indicate peaks at 3412 (NH stretching), 3302 (OH stretching), 3209 (NH stretching), and 1650 cm-1 (CO stretching)), (c) a 5 wt % 4 in silicone oil gel (arrows indicate peaks at 3309 (NH stretching), 3203 (OH stretching) and 1642 cm-1 (CO stretching)), (d) a 5 wt % 6 in silicone oil gel (arrow indicates peak at 3264 cm-1 (NH stretching)). Intensities of peaks in gel spectra are magnified 3X long the Y-axis. NH and OH stretching peaks of 1 and 4 were assigned based on comparisons with the IR spectra of stearamide (14) and N-ethyl acetamide from the data base, SDBSWeb: http://riodb01.ibase.aist.go.jp/sdbs/ (National Institute of Advanced Industrial Science and Technology, date of access April 18, 2008).

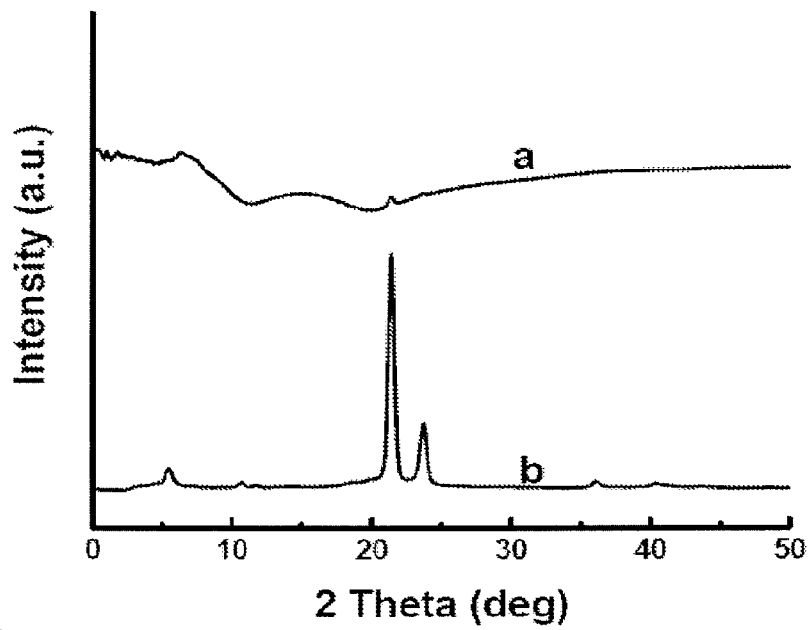
FIG. 30 X-ray diffraction patterns of 1-octadecylaminooctadecan-12-ol (12) at 24°C: (a) 5.0 wt % gel in silicone oil (after subtracting from neat silicone oil diffractogram), (b) neat powder.
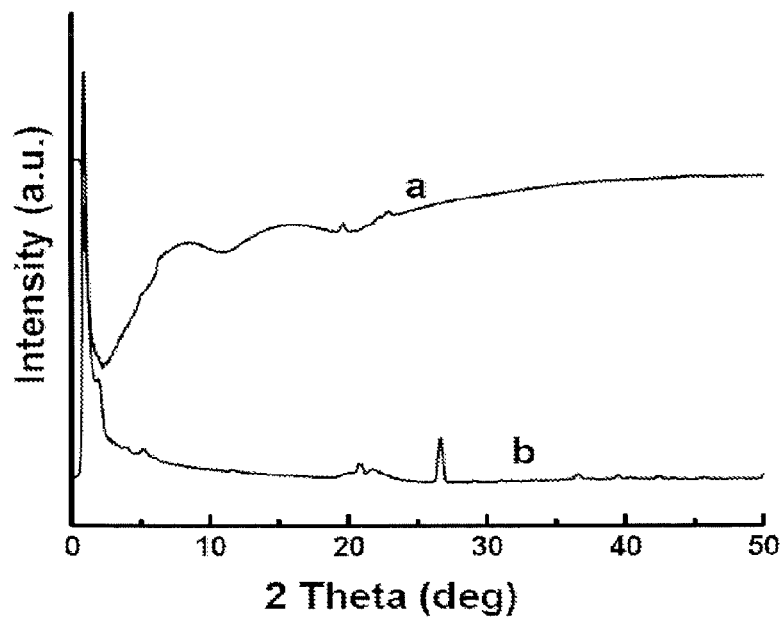
FIG. 31 X-ray diffraction patterns of 1-aminooctadecan-12-ol (7) at 24°C: (a) 5.0 wt % gel in silicone oil (after subtracting from neat silicone oil diffractogram), (b) neat powder.

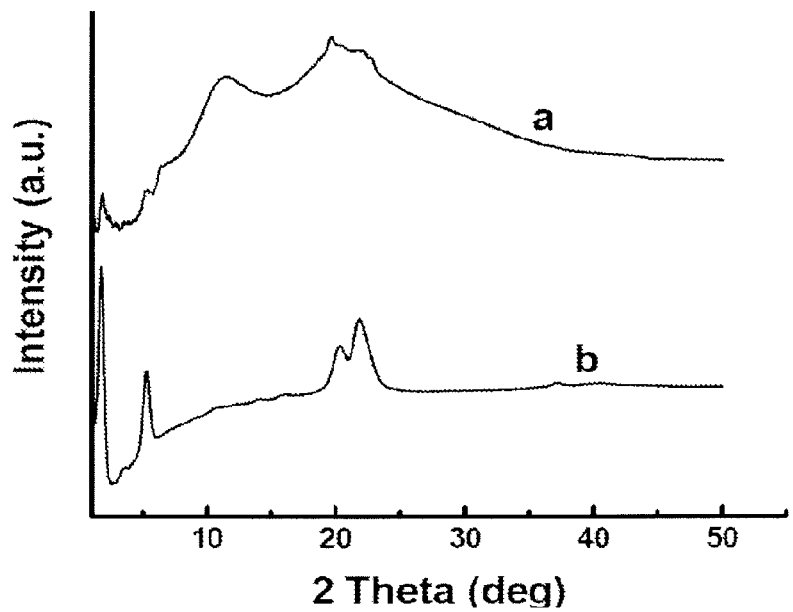
FIG. 32 X-ray diffraction patterns of ammonium carbamate salt of 1-aminooctadecan-12-ol (13) at 24 °C: (a) 4.9 wt % gel in silicone oil (after subtracting from neat silicone oil diffractogram), (b) neat powder.
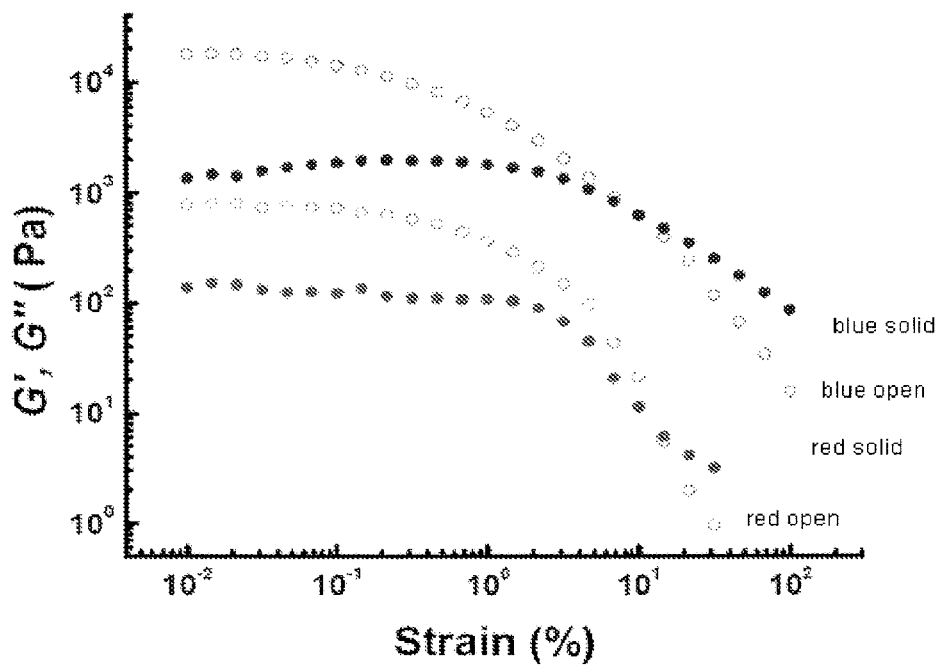
FIG. 33 Log-log strain sweep (1.0 rad/sec) for a 2.0 wt % 1 in silicone oil gel at 25 (blue) and 80 °C (red): G', open circles; G", closed circles.

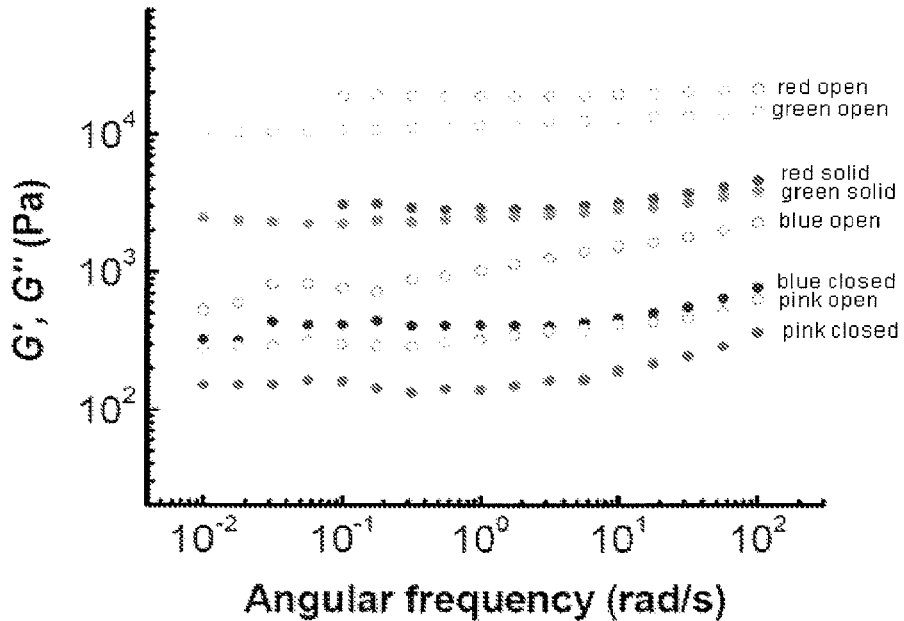
FIG. 34  Log-log frequency sweeps (0.1% strain) for a 2.0 wt % *1* in silicone oil gel at 25 (red), 40 (green), 60 (blue) and 80 °C ([pink]: G', open circles; G", closed circles.
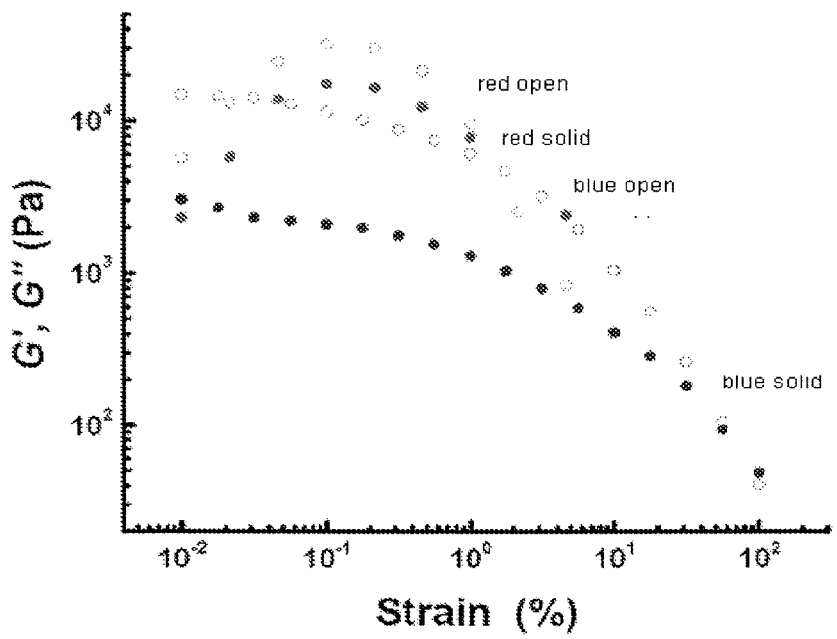
FIG. 35  Log-log strain sweep (1.0 rad/sec) for a 2.0 wt % *4* in silicone oil gel at 25 (blue) and 75 oC (red): G', open circles; G", closed circles.

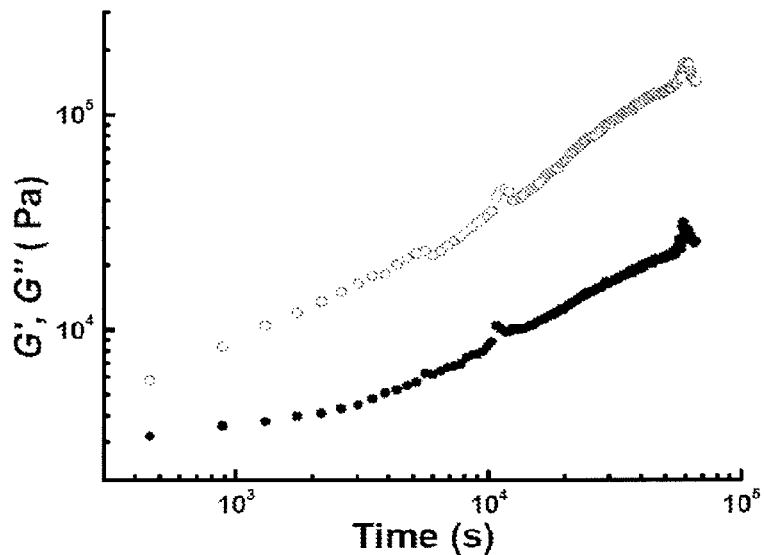
FIG. 36  Time sweep (0.1 % strain and 0.05 rad/s) at 45 oC for a 2.0 wt % 12-hydroxy-N-propyloctadecanamide (4) in silicone oil gel. G', open circles; G", closed circles.
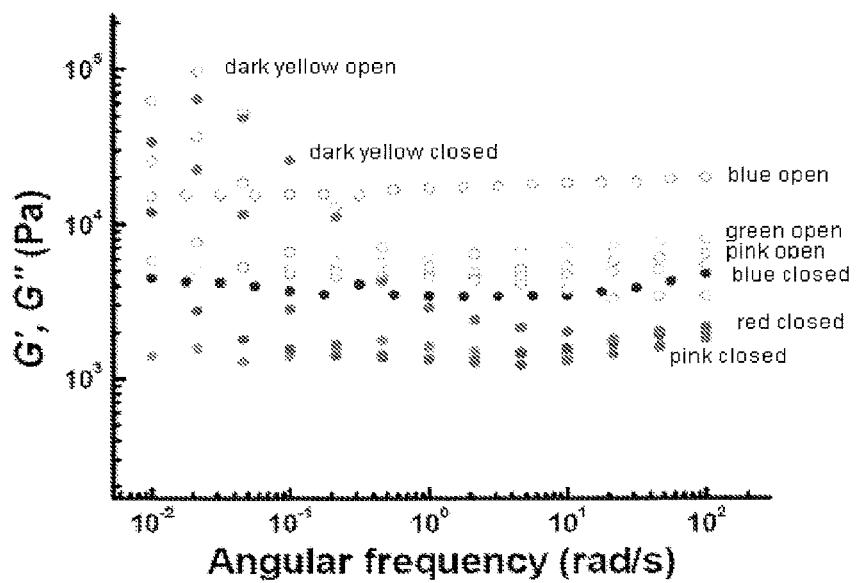
FIG. 37  Log-log frequency sweep (0.1 % strain) for a 2.0 wt % 12-hydroxy-N-propyloctadecanamide (4) in silicone oil gel at 25 (blue), 35 (green), 45 (red), 55 (pink), and 65 °C (dark yellow). G', open circles; G", closed circles.

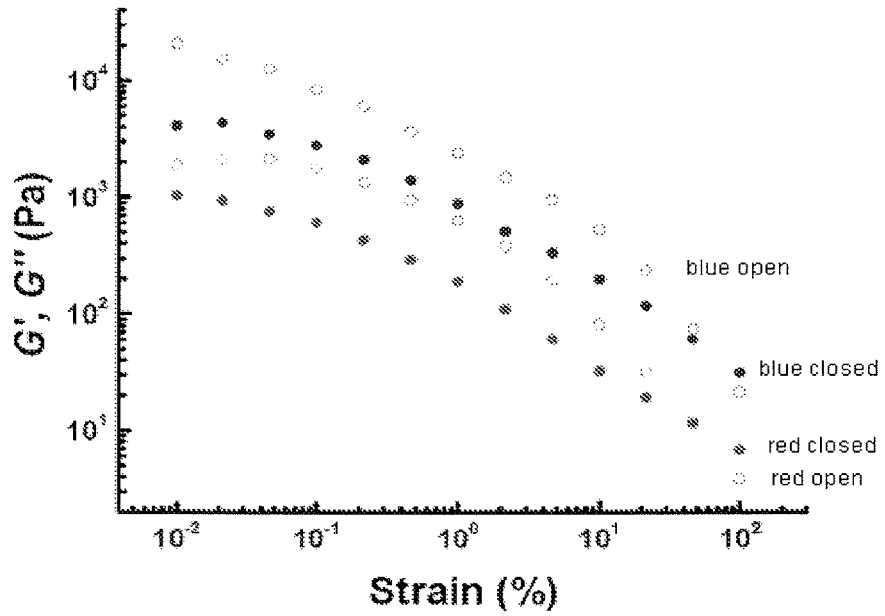
FIG. 38  Log-log strain sweep (1.0 rad/s) at 25 (blue) and 50 °C (red) for a 2.0 wt % 1-propylaminooctadecan-12-ol (*10*) in silicone oil gel. G', open circles; G'', closed circles.
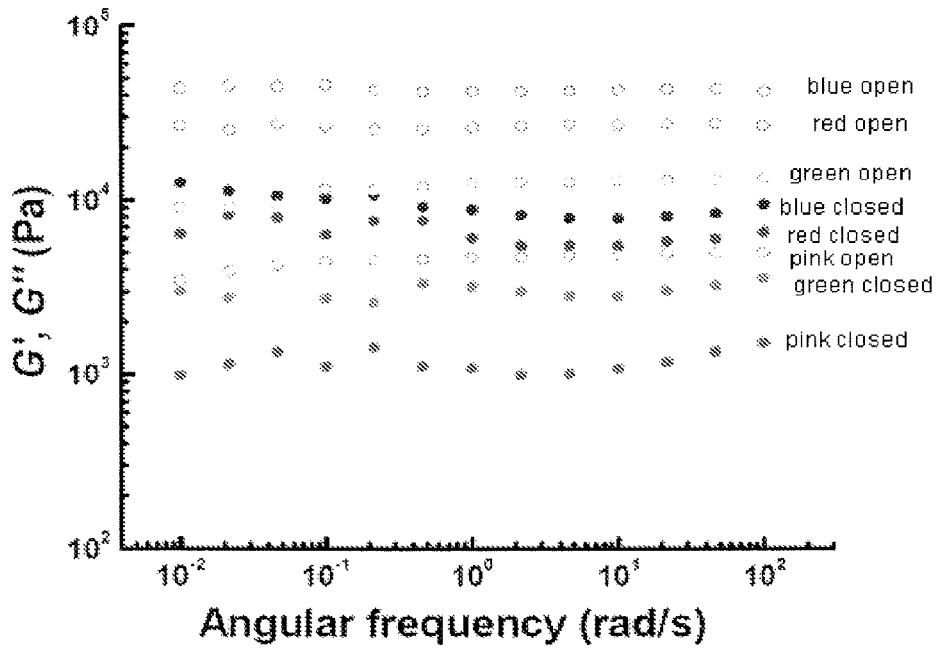
FIG. 39  Log-log frequency sweep (0.05 % strain) for a 2.0 wt % 1-propylaminooctadecan-12-ol (10) in silicone oil gel at 25 (blue), 35 (red), 45 (green) and 50 °C (pink). G', open circles; G'', closed circles.

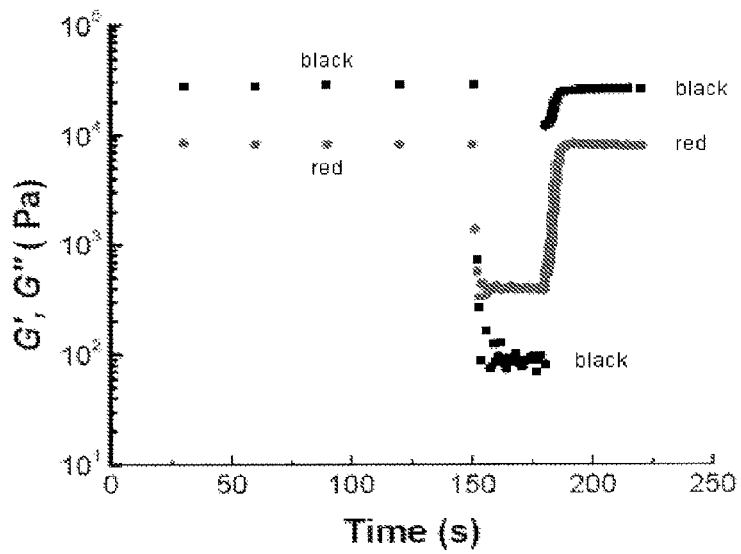

FIG. 40  $G'$ (black square) and $G''$ (red circle) as a function of time and application of different strains and frequencies to a 2.0 wt % 1 in silicone oil gel at 25°C. For the first 150 s, strain = 0.1 % and angular frequency = 100 rad/s; from 150 to 180 s, strain = 30 % and angular frequency = 1 rad/s; thereafter, strain 0.1 % and angular frequency = 100 rad/s.

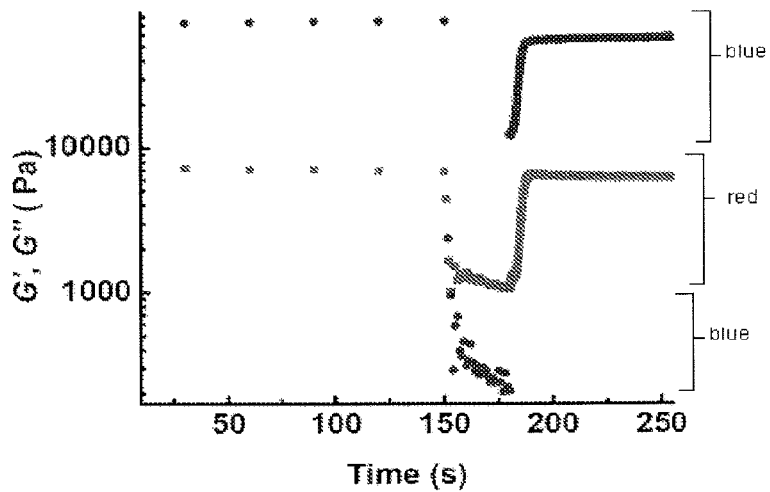

FIG. 41  $G'$ (red square) and $G''$ (blue circle) as a function of time and application of different strains and frequencies to a 2.0 wt % HSA in silicone oil gel at 25°C. For the first 150 s, strain = 0.1 % and angular frequency = 100 rad/s; from 150 to 180 s, strain = 30 % and angular frequency = 1 rad/s; thereafter, strain 0.1 % and angular frequency = 100 rad/s. The rises in G' and G" observed from 180 to 190 s are attributed to an instrumental artifact caused by the inertia of changing from higher strain (30 %) to lower strain (0.1%).

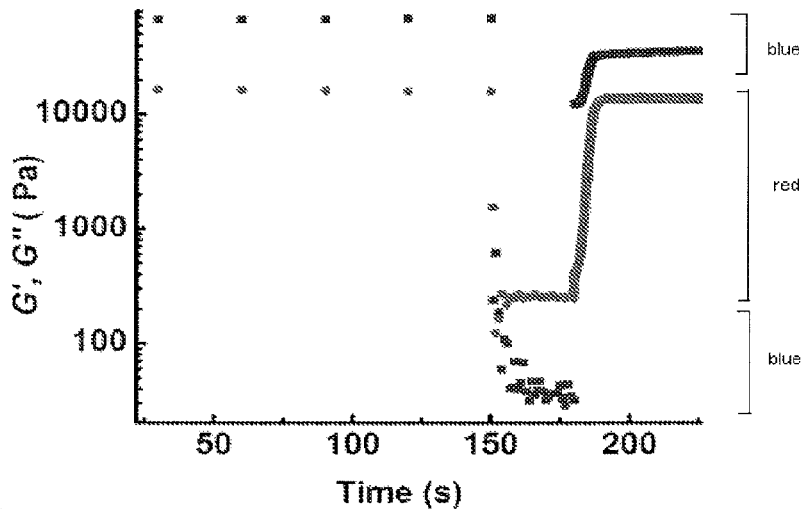

FIG. 42 G' *(blue square)* and G" *(red circle)* as a function of time and application of different strains and frequencies to a 2.0 wt % *2* in silicone oil gel at 25 °C. For the first 150 s, strain = 0.05 % and angular frequency = 100 rad/s; from 150 to 180 s, strain = 30 % and angular frequency = 1 rad/s; thereafter, strain 0.05 % and angular frequency = 100 rad/s.

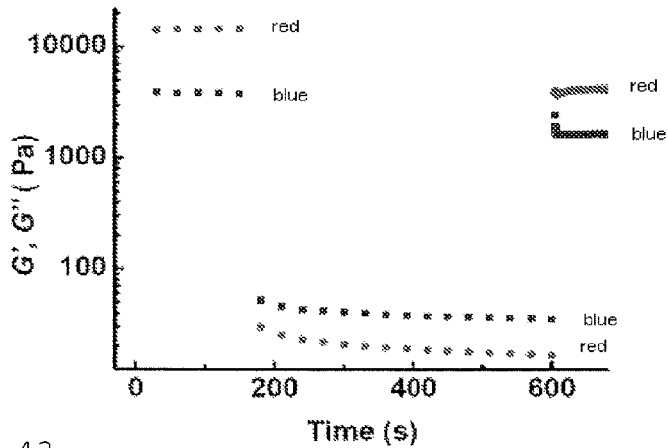

FIG. 43 G' *(blue square)* and G" *(red circle)* as a function of time and application of different strains and frequencies to a 2.1 wt % *4* in silicone oil gel at 25 °C. For the first 150 s, strain = 0.05 % and angular frequency = 100 rad/s; from 150 to 600 s, strain = 100 % and angular frequency = 1 rad/s; from 600 to 604 s, the strain and angular velocity were set effectively to zero; thereafter, strain was set to 0.05 % and angular frequency to 100 rad/s.

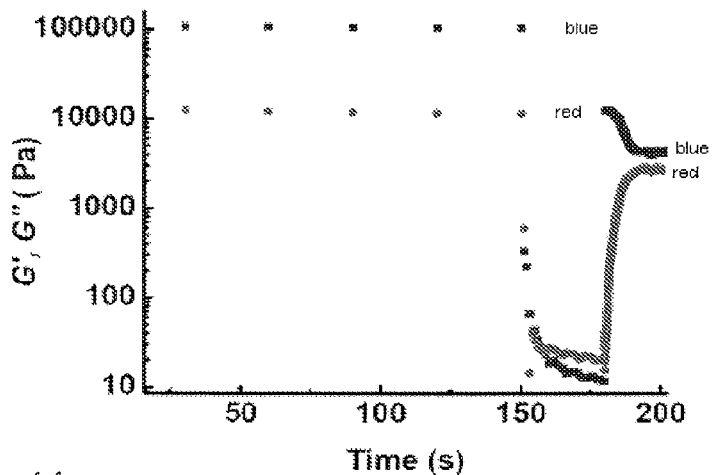

FIG. 44    G' (blue square) and G" (red circle) as a function of time and application of different strains and frequencies to a 2.1 wt % *10* in silicone oil gel at 25 °C. For the first 150 s, strain = 0.05 % and angular frequency = 100 rad/s; from 150 to 180 s, strain = 100 % and angular frequency = 1 rad/s; thereafter, strain 0.05 % and angular frequency = 100 rad/s.

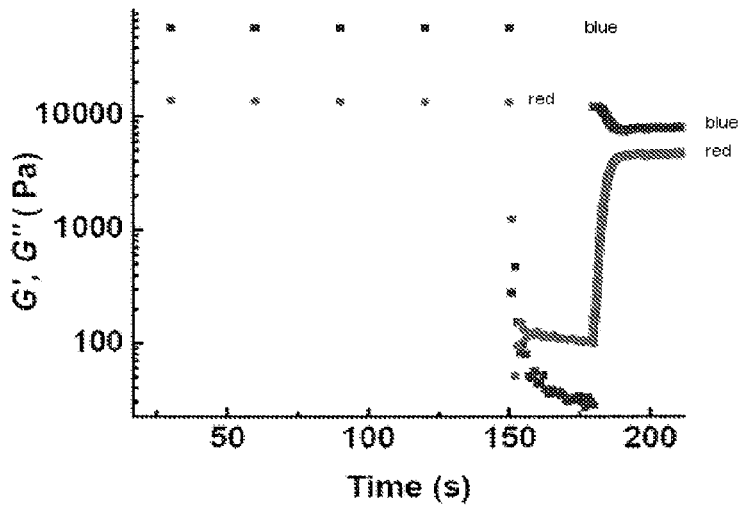

FIG. 45    G' (blue square) and G" (red circle) as a function of time and application of different strains and frequencies to a 2.1 wt % *12* in silicone oil gel at 25 °C. For the first 150 s, strain = 0.05 % and angular frequency = 100 rad/s; from 150 to 180 s, strain = 30 % and angular frequency = 1 rad/s; thereafter, strain 0.05 % and angular frequency = 100 rad/s.

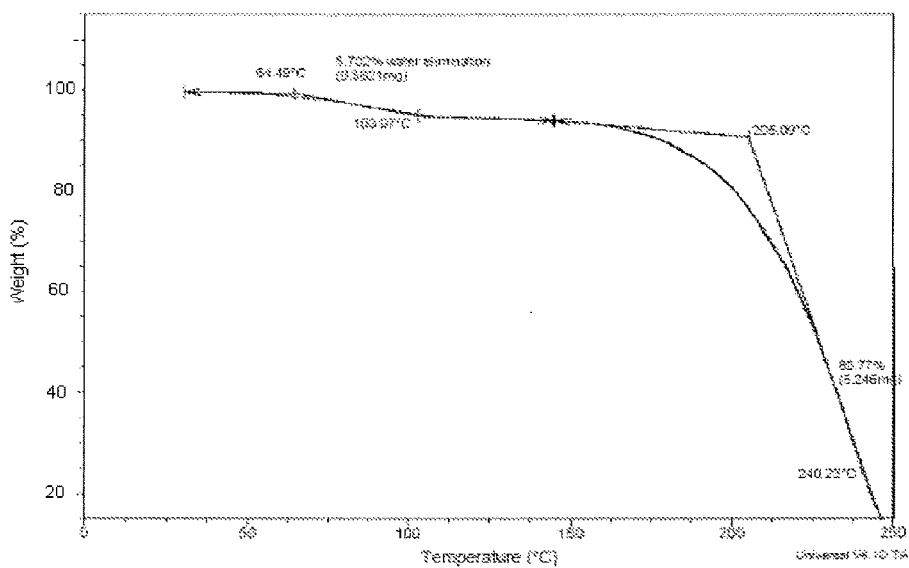
FIG. 46  TGA plot of the weight loss of 1-aminooctadecan-12-ol (*7*) versus temperature.
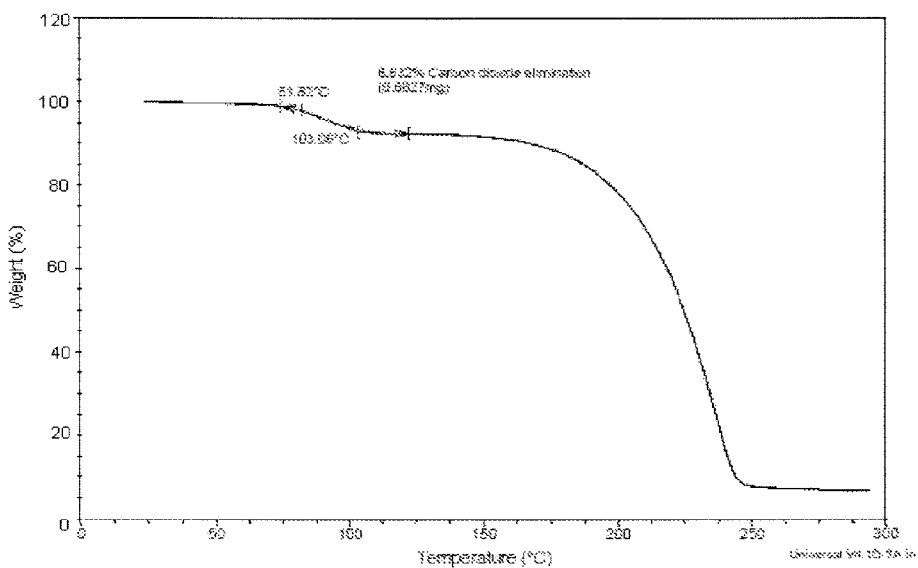
FIG. 47  TGA plot of the weight loss of *13*, the ammonium carbamate of 1-aminooctadecan-12-ol, versus temperature.

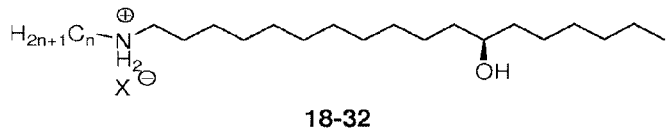

18-32

FIG. 48 Structures of gelators of the formulas: 18 to 24 (n = 0 to 6), 25 ( n = 18) and X = Cl; 26; n = 3, X = Br; 27; n = 3, X = I; 28; n = 3, X = $NO_3$ 29 ; n = 3, X = $BF_4$; 30; n = 3, X = $CH_3CO_2$; 31; n = 3, X = $C_8H_{17}CO_2$ ; 1\32 n = 3, X = $CO_2HCO_2$.

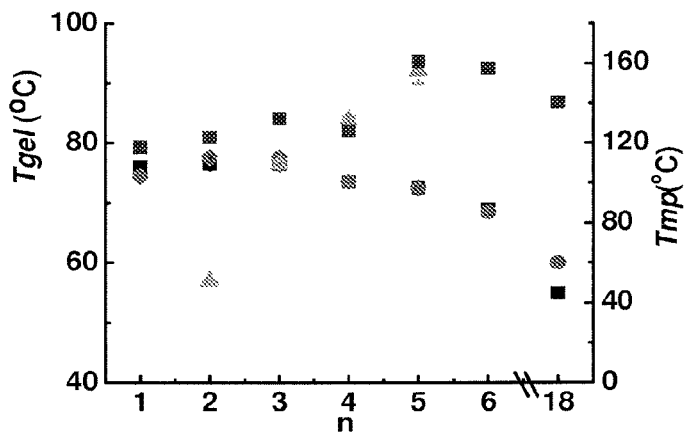

FIG. 49 Plots of the melting points (*Tmp*) of the neat 19-25(∗) or the *Tgel* values of their 2 wt % gels with various liquids versus the number of carbon atoms in their N-alkyl chains: in water (∗), in $CCl_4$ (•), and in toluene (∗).

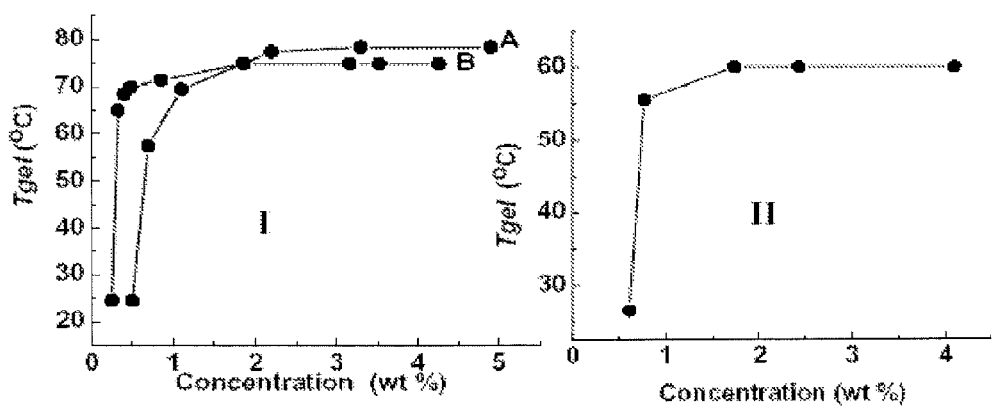

FIG. 50 (I) *Tg* values as a function of concentration of 4 in A) toluene gels and B) hydrogels. (II) *Tg* values as a function of concentration of 8 in toluene gels.

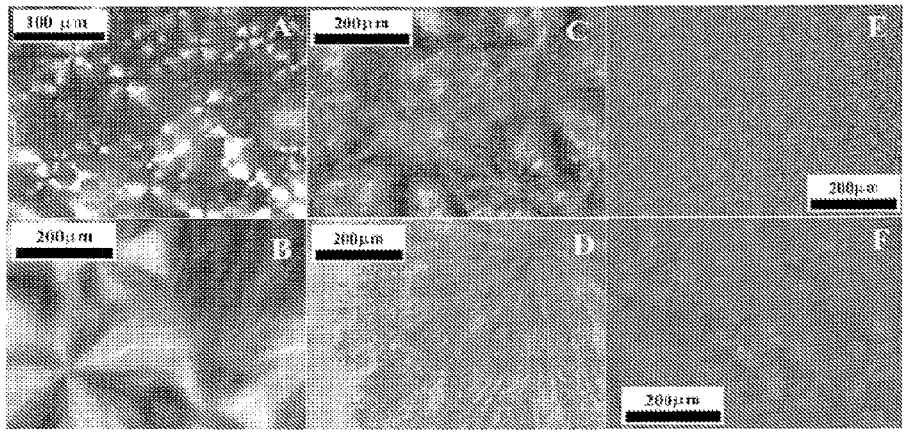

FIG. 51 Polarizing optical micrographs (POM) at 23 °C of 4 in toluene (A, B, 4.9 wt %), 4 in water (C, D, 4.8 wt %) and 8 in octanol (E, F, 1.9 wt %) gels. These gels were prepared using a fast-cooling (A, C and E) or slow-cooling (B, D and F) protocols. The images C, D, E and F were taken with a full-wave plate.

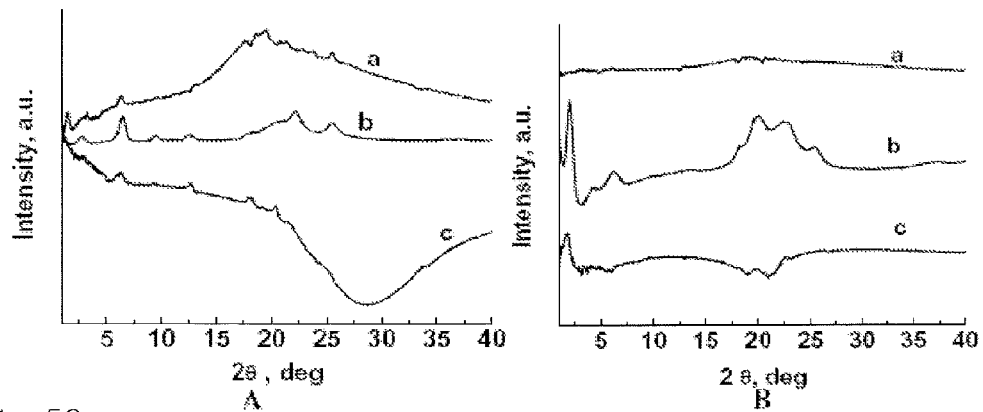

FIG. 52 Vertically offset XRD diffractograms at 22 °C of A) (a) a gel consisting of 5.0 wt % 4 in toluene after empirical subtraction of solvent diffractions, (b) neat 4 and (c) a gel consisting of 5.1 wt % 4 in water after empirical subtraction of solvent diffractions. (B) (a) a gel consisting of 4.9 wt % 8 in toluene after empirical subtraction of solvent diffractions, (b) neat 8 and (c) a gel consisting of 4.9 wt % 8 in octanol after empirical subtraction of solvent diffractions.

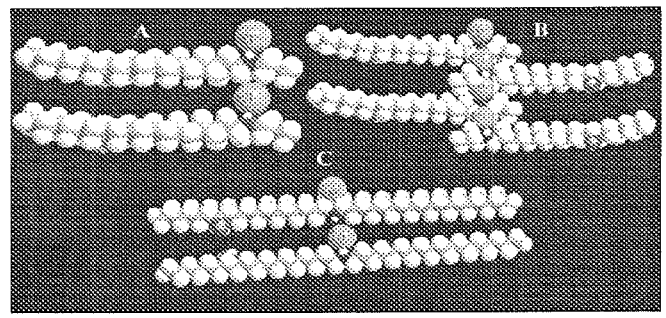
FIG. 53  Proposed packing arrangement of gelator molecules of (A) 4 in hydrogel aggregates, (B) 4 in toluene gel aggregates and (C) 8 in octanol gel aggregates from molecular mechanics 2 (MM2) calculations.
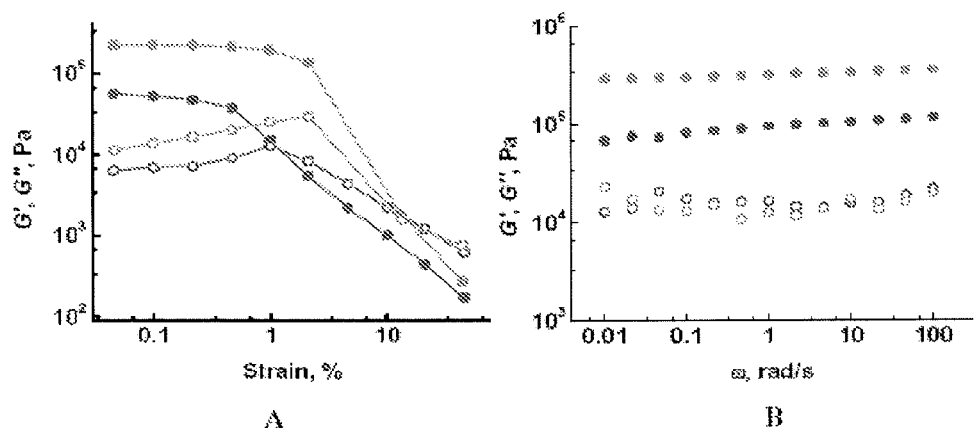
FIG. 54  Log-log strain sweep (1.0 rad/sec, (A)) and log-log frequency sweep (0.1 % strain, (B)) for a 2.1 wt % hydrogel (green) and a 2.1 wt % toluene gel (red) of 4 at 25°C: $G'$, closed circles; $G''$, open circles.

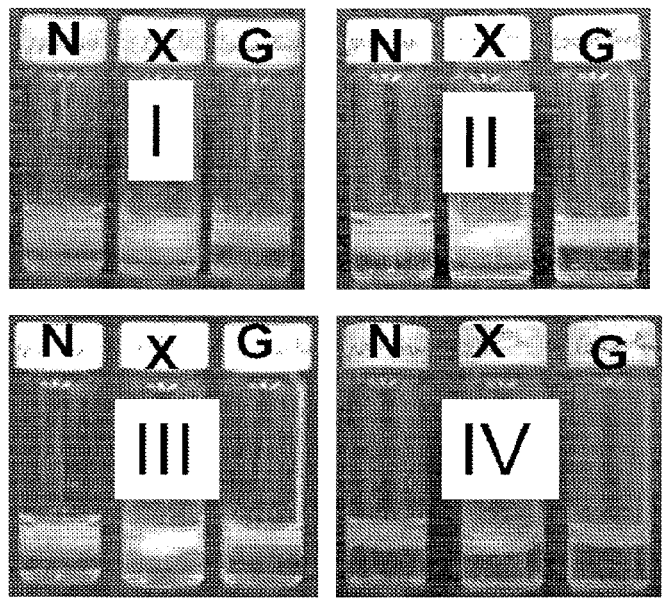
FIG. 55  Naptha (N), xylol (X) and gasoline (G) in the presence of the gelator/methanol solution: I) 0 min, II) 1h, III) 20 h and IV) 40 h. Note that 12HSA3Cl is not a liquid which is gelled by 12HSA3Cl.
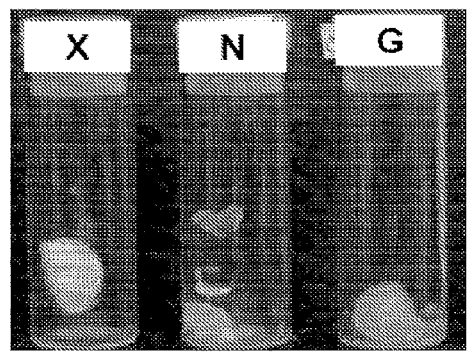
FIG. 56  Visual images of the isolated gels of 12HSA3Cl with xylol (X), Naptha (N) and gasoline (G).

FAST RECOVERY OF THIXOTROPY BY ORGANOGELS WITH LOW MOLECULAR WEIGHT GELATORS

CROSS REFERENCE TO PRIORITY APPLICATION

This application claims priority of provisional application Nos. 61/282,609, filed Mar. 8, 2010 and 61/346,388, filed May 19, 2010, said applications being incorporated by reference herein in their entireties and relied upon.

TECHNICAL FIELD

Low molecular weight gelators, methods of making such gelators, organogels comprising such gelators and methods of using such organogels are described. In exemplary methods, the gelators can be used in a variety of applications including the delivery of pharmaceutical active pharmaceutical ingredients, in food, cosmetics and consumer products, and in containing the unexpected release of chemical that occur for example in spills.

BACKGROUND

Low molecular weight gelators, methods of making such gelators, organogels comprising such gelators and methods of using such organogels are described. Low molecular weight gelators which are capable of gelling hydrogels and organogels, methods of making such gelators, organogels comprising such gelators and methods of using such organogels are described. For at least the reasons provided below, conventional low molecular weight gelators and gels formed using the gelators are not optimal.

SUMMARY

This application relates to low molecular weight gelators which can be used to produce organogels, methods of making such gelators, organogels comprising such gelators and methods of using such organogels. Such materials and methods are described. This application also relates to low molecular weight gelators which are capable of gelling hydrogels and organogels, methods of making such gelators, organogels comprising such gelators and methods of using such organogels. Such materials and methods are described.

In an embodiment, a gelling agent is a compound of formula (I):

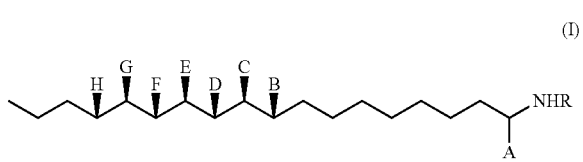

wherein, R is hydrogen or an alkyl group having from 1 to 36 carbon atoms, A is a hydrogen or a carbonyl, and at least one of B, C, D, E, F, G and H is a hydroxyl group and the others are hydrogen, and salts thereof, wherein the compound is in the (R) form and is a gelator that can be used to form organogels.

In an embodiment, a gelling agent is a compound of formula (II):

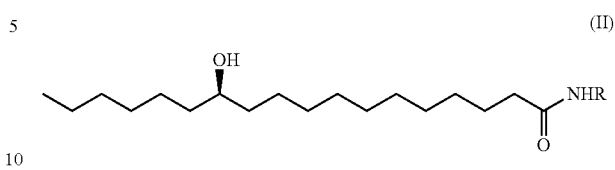

wherein R is hydrogen or an alkyl group having from 1 to 18 carbon atoms, and salts thereof, wherein the compound is in the (R) form and is a gelator that can be used to form organogels.

In an embodiment, a gelling agent is compound of formula (III):

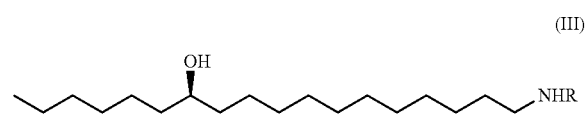

wherein R is hydrogen or an alkyl group having from 1 to 18 carbon atoms, and salts thereof, wherein the compound is in the (R) form and is a gelator that can be used to form organogels.

In an embodiment, a thixotropic gel comprises an organic solvent and a compound of formula (I):

(I)

H—G—F—E—D—C—B—NHR
      A wherein R is hydrogen or an alkyl group having from 1 to 36 carbon atoms, A is a hydrogen or a carbonyl, and at least one of B, C, D, E, F, G and H is a hydroxyl group and the others are hydrogen, and salts thereof, and the compound is in the (R) form.

In an embodiment, a thixotropic gel comprises an organic solvent and a compound of formula (II) or formula (III):

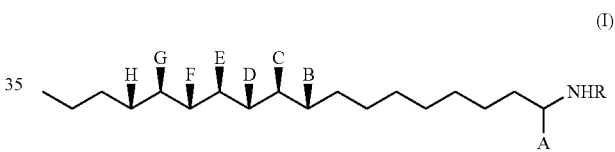

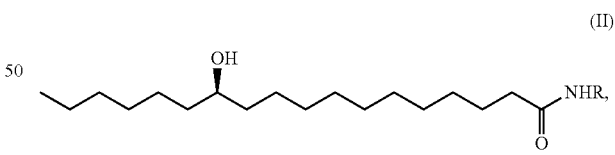

wherein R is hydrogen or an alkyl group having from 1 to 18 carbon atoms, and salts thereof, and the compound of formula (II) or formula (III) is in the (R) form.

In an embodiment, a method of manufacturing 12-hydroxy-N-alkyloctadecanamides comprises: (a) adding a solution of 12-hydroxystearamide and triethylamine in a non-reactive solvent to a cooled solution of ethyl chloroformate in a non-reactive solvent, and (b) adding an alkyl amine to the solution of step (a).

In an embodiment, a method of manufacturing 1-(alkylamino) octadecan-12-ols comprises the step of adding LAH to a suspension of suspension of a 12-hydroxy-N-alkyloctadecanamide in dry THF under a nitrogen atmosphere.

In an embodiment, a pharmaceutical composition comprises an active pharmaceutical ingredient and a compound of formula (I):

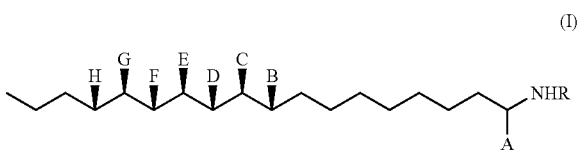

(I)

wherein R is hydrogen or an alkyl group having from 1 to 36 carbon atoms, A is a hydrogen or a carbonyl, and at least one of B, C, D, E, F, G and H is a hydroxyl group and the others are hydrogen, and salts thereof, wherein the compound is in the (R) form, and a pharmaceutically acceptable carrier.

In an embodiment, a food composition comprises a mixture of a food and a compound of formula (I):

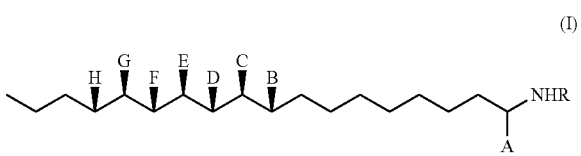

(I)

wherein R is hydrogen or an alkyl group having from 1 to 36 carbon atoms, A is a hydrogen or a carbonyl, and at least one of B, C, D, E, F, G and H is a hydroxyl group and the others are hydrogen, and salts thereof, wherein the compound is in the (R) form.

In an embodiment, a cosmetic composition comprises at least one cosmetically acceptable ingredient and a compound of formula (I):

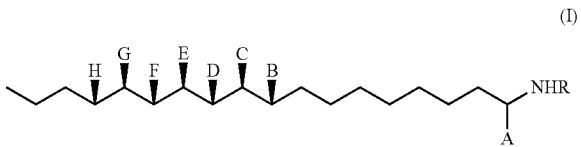

(I)

wherein R is hydrogen or an alkyl group having from 1 to 36 carbon atoms, A is a hydrogen or a carbonyl, and at least one of B, C, D, E, F, G and H is a hydroxyl group and the others are hydrogen, and salts thereof, wherein the compound is in the (R) form, and a pharmaceutically acceptable carrier.

In an embodiment, a consumer product comprises a compound of formula (I):

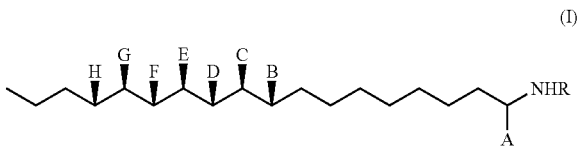

(I)

wherein R is hydrogen or an alkyl group having from 1 to 36 carbon atoms, A is a hydrogen or a carbonyl, and at least one of B, C, D, E, F, G and H is a hydroxyl group and the others are hydrogen, and salts thereof, wherein the compound is in the (R) form, and an acceptable medium.

In an embodiment, a method for containing an unintentional chemical release, comprises forming a gel a compound of formula (I):

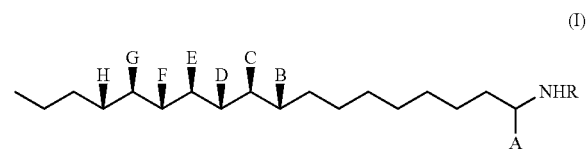

(I)

wherein R is hydrogen or an alkyl group having from 1 to 36 carbon atoms, A is a hydrogen or a carbonyl, and at least one of B, C, D, E, F, G and H is a hydroxyl group and the others are hydrogen, and salts thereof, wherein the compound is in the (R) form with the chemical that was unintentionally released.

In an embodiment, a gelling agent is a compound of formula (IV):

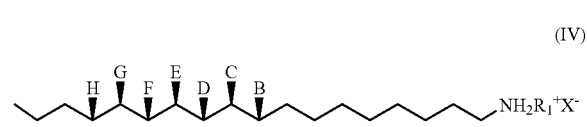

(IV)

wherein $R_1$ is an alkyl group of the formula $C_nH_{2n+1}$ or an aryl group, n is an integer from 0 to 6, X is an anion, and at least one of B, C, D, E, F, G and H is a hydroxyl group and the others are hydrogen, and the compound is in the (R) form. In an embodiment, E is a hydroxyl group. The gelling agent of formula (IV) is a gelator that can be used to form an organogel or a hydrogel.

In an embodiment, a thixotropic gel comprises an organic solvent and a compound of formula (IV):

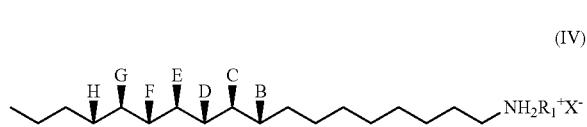

(IV)

wherein $R_1$ is an alkyl group of the formula $C_nH_{2n+1}$ or an aryl group, n is an integer from 0 to 6, X is an anion, and at least one of B, C, D, E, F, G and H is a hydroxy and the others are hydrogen, and the compound is in the (R) form. In another embodiment, E is a hydroxyl group.

In an embodiment, a pharmaceutical composition comprises an active pharmaceutical ingredient and a compound of formula (IV):

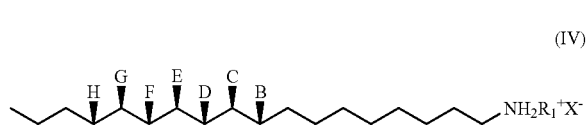

(IV)

wherein $R_1$ is an alkyl group of the formula $C_nH_{2n+1}$ or an aryl group, n is an integer from 0 to 6, X is an anion, and at least one of B, C, D, E, F, G and H is a hydroxy and the others are hydrogen, and the compound is in the (R) form, and a pharmaceutically acceptable carrier. In another embodiment, E is a hydroxyl group.

In an embodiment, a processed food composition comprises a food and a compound of formula (IV):

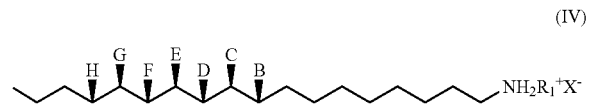
(IV)

Wherein $R_1$ is an alkyl group of the formula $C_nH_{2n+1}$ or an aryl group, n is an integer from 0 to 6, X is an anion, and at least one of B, C, D, E, F, G and H is a hydroxy and the others are hydrogen, and the compound is in the (R) form, wherein the compound is in the (R) form. In another embodiment, E is a hydroxyl group.

In an embodiment, a cosmetic composition comprises at least one cosmetically acceptable ingredient and a compound of formula (IV):

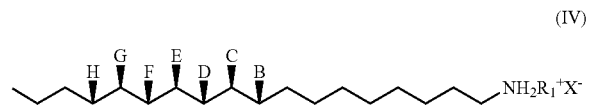
(IV)

wherein $R_1$ is an alkyl group of the formula $C_nH_{2n+1}$ or an aryl group, n is an integer from 0 to 6, X is an anion, and at least one of B, C, D, E, F, G and H is a hydroxy and the others are hydrogen, and the compound is in the (R) form, wherein the compound is in the (R) form, and a cosmetically acceptable carrier. In another embodiment, E is a hydroxyl group.

In an embodiment, a consumer product comprises a compound of formula (IV):

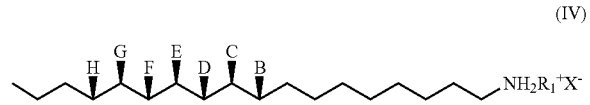
(IV)

wherein $R_1$ is an alkyl group of the formula $C_nH_{2n+1}$ or an aryl group, n is an integer from 0 to 6, X is an anion, and at least one of B, C, D, E, F, G and H is a hydroxy and the others are hydrogen, and the compound is in the (R) form, wherein the compound is in the (R) form, and an acceptable medium. In another embodiment, E is a hydroxyl group.

In an embodiment, a method for containing an unintentional chemical release, comprises forming a gel a compound of formula (IV):

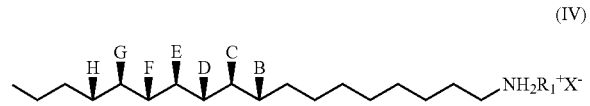
(IV)

wherein $R_1$ is an alkyl group of the formula $C_nH_{2n+1}$ or an aryl group, n is an integer from 0 to 6, X is an anion, and at least one of B, C, D, E, F, G and H is a hydroxy and the others are hydrogen, and the compound is in the (R) form, wherein the compound is in the (R) form, with the chemical that was unintentionally released. In another embodiment, E is a hydroxyl group.

The group $R^1$ in the compounds of formula (IV) can be covalently attached to the nitrogen atom or can be present as the counterion of the positively charged portion of the salt.

The applicability of the present teachings to other areas will become apparent from the detailed description provided hereinafter. It should be understood that the detailed description and specific examples, while indicating certain embodiments of the present teachings, are intended for purposes of illustration only and are not intended to limit the scope of the invention.

BRIEF DESCRIPTION OF THE DRAWINGS

FIG. 1 shows a representation of the design of LMOGs with increasing complexity.

FIG. 2 shows the chemical structures of exemplary gelators and analogous compounds without the hydroxyl group of exemplary gelators.

FIG. 3 shows the chemical structures of exemplary gelators of formulas 1-12.

FIG. 4 is a plot of the melting points ($T_{mp}$) of the neat amide gelators (1-6) (0) or the Tg values of their gels with various liquids versus n, the number of carbon atoms in their N-alkyl chains.

FIG. 5 is a plot of the melting points ($T_{mp}$) of the neat amine gelators (7-12) or the Tg values of their gels with various liquids versus n, the number of carbon atoms in their N-alkyl chains.

FIG. 6 is a plot of Tg values of silicone oil gels as a function of concentration of exemplary gelling agents.

FIG. 7 is a plot of Tg values of toluene gels as a function of concentration of exemplary agents.

FIG. 8 shows polarizing optical micrographs at 24° C. of 2 wt % 1 in (a, b) silicone oil and (c, d) toluene gels prepared by (a, c) fast-cooling and (b, d) slow-cooling protocols.

FIG. 9 shows polarizing optical micrographs at 24° C. of gels of 2 wt % 4 in decane prepared by (a) fast-cooling and (b) slow-cooling protocols.

FIG. 10 shows polarizing optical micrographs at 24° C. of gels of 2 wt % 4 in $CCl_4$ prepared by (a) fast-cooling and (b) slow-cooling protocols.

FIG. 11 shows polarizing optical micrographs (24° C.) of gels of 2 wt % 4 in DMSO prepared by (a) fast-cooling and (b) slow-cooling protocols.

FIG. 12 shows polarizing optical micrographs (24° C.) of gels of 2 wt % 4 in toluene prepared by (a) fast-cooling and (b) slow-cooling protocols.

FIG. 13 shows polarizing optical micrographs (24° C.) of gels of 2 wt % 4 in silicone oil prepared by (a) fast-cooling and (b) slow-cooling protocols.

FIG. 14 shows polarizing optical micrographs (24° C.) of gels of 2 wt % 6 in decane prepared by (a) fast-cooling and (b) slow-cooling protocols.

FIG. 15 shows polarizing optical micrographs (24° C.) of gels of 2 wt % 6 in $CCl_4$ prepared by (a) fast-cooling and (b) slow-cooling protocols.

FIG. 16 shows polarizing optical micrographs (24° C.) of gels of 2 wt % 6 in DMSO prepared by (a) fast-cooling and (b) slow-cooling protocols.

FIG. 17 shows polarizing optical micrographs (24° C.) of gels of 2 wt % 6 in silicone oil prepared by (a) fast-cooling and (b) slow-cooling protocols.

FIG. 18 shows polarizing optical micrographs (24° C.) of gels of 2 wt % 10 in $CCl_4$ prepared by (a) fast-cooling and (b) slow-cooling protocols.

FIG. 19 shows polarizing optical micrographs (24° C.) of gels of 2 wt % 10 in decane prepared by (a) fast-cooling and (b) slow-cooling protocols.

FIG. 20 shows polarizing optical micrographs (24° C.) of gels of 2 wt % 10 in DMSO prepared by (a) fast-cooling and (b) slow-cooling protocols.

FIG. 21 shows polarizing optical micrographs (24° C.) of gels of 2 wt % 10 in toluene prepared by (a) fast-cooling and (b) slow-cooling protocols.

FIG. 22 shows polarizing optical micrographs (24° C.) of gels of 2 wt % 10 in silicone oil prepared by (a) fast-cooling and (b) slow-cooling.

FIG. 23 shows polarizing optical micrographs (24° C.) of gels of 2 wt % 12 in silicone oil prepared by (a) fast-cooling and (b) slow-cooling protocols.

FIG. 24 shows polarizing optical micrographs at 24° C. of gels of 0.42 wt % 6 in silicone oil prepared by (a) fast-cooling and (b) slow-cooling protocols.

FIG. 25 is SEM images of xerogels prepared from (a) 2.0 wt % 1 in $CCl_4$, (b) 0.5 wt % 1 in $CCl_4$, (c) 2.0 wt % 1 in chlorobenzene, and (d) 0.5 wt % 1 in chlorobenzene.

FIG. 26 shows XRD patterns at 24° C. of: (a) 4.8 wt % 1 in silicone oil gel after solvent subtraction; (b) neat 1; (c) 5.2 wt % 4 in silicone oil gel after solvent subtraction; (d) neat 4; (e) 5.0 wt % 6 in silicone oil gel after solvent subtraction; and (f) neat 6.

FIG. 27 shows proposed packing arrangements of gelator molecules in gel aggregates.

FIG. 28 shows X-ray diffractograms of 1-(propylamino)octadecan-12-ol (10) at 24° C.: (a) 4.8 wt % gel in silicone oil (after subtracting from neat silicone oil diffractogram), (b) neat powder.

FIG. 29 shows IR spectra of (a) neat silicone oil, (b) a 5 wt % 1 in silicone oil gel.

FIG. 30 shows X-ray diffraction patterns of 1-octadecylaminooctadecan-12-ol (12) at 24° C.: (a) 5.0 wt % gel in silicone oil, and (b) neat powder.

FIG. 31 shows X-ray diffraction patterns of 1-aminooctadecan-12-ol (7) at 24° C.: (a) 5.0 wt % gel in silicone oil, and (b) neat powder.

FIG. 32 shows X-ray diffraction patterns of ammonium carbamate salt of 1-aminooctadecan-12-ol (13) at 24° C.: (a) 4.9 wt % gel in silicone oil, and (b) neat powder.

FIG. 33 shows Log-log strain sweep for a 2.0 wt % 1 in silicone oil gel at 25 and 80° C.

FIG. 34 shows Log-log frequency sweeps (0.1% strain) for a 2.0 wt % 1 in silicone oil gel at 25, 40, 60 and 80° C.

FIG. 35 shows Log-log strain sweep (1.0 rad/sec) for a 2.0 wt % 4 in silicone oil gel at 25 and 75° C.

FIG. 36 shows Time sweep (0.1% strain and 0.05 rad/s) at 45° C. for a 2.0 wt % 12-hydroxy-N-propyloctadecanamide (4) in silicone oil gel.

FIG. 37 shows log-log frequency sweep (0.1% strain) for a 2.0 wt % 12-hydroxy-N-propyloctadecanamide (4) in silicone oil gel at 2, 35, 45, 55, and 65° C.

FIG. 38 shows log-log strain sweep (1.0 rad/s) at 25 (blue) and 50° C. (red) for a 2.0 wt % 1-propylaminooctadecan-12-ol (10) in silicone oil gel.

FIG. 39 shows log-log frequency sweep (0.05% strain) for a 2.0 wt % 1-propylaminooctadecan-12-ol (10) in silicone oil gel at 25, 35, 45 and 50° C.

FIG. 40 shows. G' and G" as a function of time and application of different strains and frequencies to a 2.0 wt % 1 in silicone oil gel at 25° C.

FIG. 41 shows. G' and G" as a function of time and application of different strains and frequencies to a 2.0 wt % HSA in silicone oil gel at 25° C.

FIG. 42 shows. G' and G" as a function of time and application of different strains and frequencies to a 2.0 wt % 2 in silicone oil gel at 25° C.

FIG. 43 shows. G' and G" as a function of time and application of different strains and frequencies to a 2.1 wt % 4 in silicone oil gel at 25° C.

FIG. 44 shows. G' and G" as a function of time and application of different strains and frequencies to a 2.1 wt % 10 in silicone oil gel at 25° C.

FIG. 45 shows. G' and G" as a function of time and application of different strains and frequencies to a 2.1 wt % 12 in silicone oil gel at 25° C.

FIG. 46 shows a TGA plot of the weight loss of 1-aminooctadecan-12-ol (7) versus temperature.

FIG. 47 shows a TGA plot of the weight loss of 13, the ammonium carbamate of 1-aminooctadecan-12-ol, versus temperature.

FIG. 48 shows the chemical structures of exemplary gelators of formulas 18-24.

FIG. 49 shows plots of the melting points ($T_{mp}$) of the neat 2-8 or the Tgel values of their 2 wt % gels with various liquids versus the number of carbon atoms in their N-alkyl chains: in water, in $CCl_4$, and in toluene.

FIG. 50 shows (I) Tg values as a function of concentration of 4 in A) toluene gels and B) hydrogels. (II) Tg values as a function of concentration of 8 in toluene gels.

FIG. 51 shows polarizing optical micrographs (POM) at 23° C. of 4 in toluene (A, B, 4.9 wt %), 4 in water (C, D, 4.8 wt %) and 8 in octanol (E, F, 1.9 wt %) gels.

FIG. 52 shows offset XRD diffractograms at 22° C. of A) (a) a gel consisting of 5.0 wt % 4 in toluene after empirical subtraction of solvent diffractions, (b) neat 4 and (c) a gel consisting of 5.1 wt % 4 in water after empirical subtraction of solvent diffractions. (B) (a) a gel consisting of 4.9 wt 8 in toluene after empirical subtraction of solvent diffractions, (b) neat 8 and (c) a gel consisting of 4.9 wt % 8 in octanol after empirical subtraction of solvent diffractions.

FIG. 53 shows proposed packing arrangement of gelator molecules of (A) 4 in hydrogel aggregates, (B) 4 in toluene gel aggregates and (C) 8 in octanol gel aggregates from molecular mechanics 2 (MM2) calculations.

FIG. 54 shows log-log strain sweep (1.0 rad/sec, (A)) and log-log frequency sweep (0.1% strain, (B)) for a 2.1 wt % hydrogel and a 2.1 wt % toluene gel of 4 at 25° C.

FIG. 55 shows visual images of naptha, xylol and gasoline in the presence of the gelator/methanol solution at various times.

FIG. 56 shows visual images of isolated gels of 12HSA3Cl with xylol, naptha and gasoline.

DETAILED DESCRIPTION

Low molecular weight gelators which from organogels, methods of making such gelators, organogels comprising such gelators and methods of using such organogels. Such materials and methods are described. This application also relates to low molecular weight gelators which are capable of gelling hydrogels and organogels, methods of making such gelators, organogels comprising such gelators and methods of using such organogels. Such materials and methods are described.

It is to be understood that this application is not limited to particular embodiments described. It is also to be understood that the terminology used herein is for the purpose of describing particular embodiments only, and is not intended to be limiting, since the scope of the present application will be limited only by the appended claims.

Unless defined otherwise, all technical and scientific terms used herein have the same meaning as commonly understood by one of ordinary skill in the art. Although any methods and materials similar or equivalent to those described herein can also be used in the practice or testing of exemplary embodiments, specific preferred methods and materials are now described.

As used herein, the recitation of a numerical range for a variable is intended to convey that the variable can be equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Definitions

The following definitions are provided for specific terms which are used in the following written description.

As used herein, the singular form "a", "an" and "the" include plural references unless the context clearly dictates otherwise. For example, the term "a cell" includes a plurality of cells, including mixtures thereof.

As used herein, the term "about" means approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 20%.

As used herein, the term "aryl" refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, .alpha.s-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthuene, rubicene, triphenylene, trinaphthalene and the like. Preferably, an aryl group comprises from 6 to 20 carbon atoms ($C_6$-$C_{20}$ aryl), more preferably from 6 to 15 carbon atoms ($C_6$-$C_{15}$ aryl) and even more preferably from 6 to 10 carbon atoms ($C_6$-$C_{10}$ aryl). More preferably the aryl group is a naphthyl group or an anthranyl group. Even more preferably, the aryl group is a napthyl group bound at the 1- or 2-position or an anthranyl group bound at the 1-, 2- or 9-position.

The aryl group may be substituted with one or more of the following substituents, which may be identical or different: a halogen atom, a hydroxy group, a nitro group, a cyano group, an amino group, a formyl group, a carbamoyl group, an aminosulfonyl group, a lower alkyl group, a lower alkylamino group, a hydroxy-lower alkylamino group, a di-lower alkylamino group, an imino group, a lower alkylsulfonyl group, a lower alkylsulfonylamino group, a lower alkoxy group, which may be substituted with 1 to 3 halogen atom(s), a lower alkoxycarbonyl group, a lower alkoxycarbonylamino group, a lower alkanoyl group which may be substituted with 1 to 3 halogen atom(s), a carboxyl group, a hydroxyiminomethyl group, a methoxyiminomethyl group, and a lower alkylthio group.

The term "lower alkyl group" refers to a straight-chained or branched alkyl group having 1 to 6 carbon atom(s), and examples thereof include a methyl group, an ethyl group, a propyl group, an isopropyl group, a butyl group, an isobutyl group, a sec-butyl group, a tert-butyl group, a pentyl group, a hexyl group, and the like.

The term "halogen atom" refers to a fluorine atom, a chlorine atom, a bromine atom, an iodine atom.

The term "lower alkylamino group" refers to a substituent formed by N-substitution of the above "lower alkyl group" to an amino group, and examples thereof include an N-methylamino group, an N-ethylamino group, an N-propylamino group, an N-isopropylamino group, an N-butylamino group, an N-isobutylamino group, an N-tert-butylamino group, an N-pentylamino group, an N-hexylamino group, and the like.

The term "hydroxy-lower alkylamino group" refers to a substituent formed by substitution of one or more of hydroxy group(s) to the above "lower alkyl amino group", and examples thereof include an N-hydroxyethylamino group, an N-hydroxypropylamino group, an N-hydroxyisopropylamino group, an N-hydroxybutylamino group, an N-hydroxyisobutylamino group, an N-hydroxy-tert-butylamino group, an N-hydroxypentylamino group, an N-hydroxyhexylamino group, and the like.

The term "di-lower alkylamino group" refers to a substituent formed by N,N-disubstitution of the above "lower alkyl group" to an amino group, and examples thereof include an N,N-dimethylamino group, an N,N-diethylamino group, an N,N-dipropylamino group, an N,N-diisopropylamino group, an N,N-dibutylamino group, an N,N-diisobutylamino group, an N,N-ditert-butylamino group, an N,N-dipentylamino group, an N,N-dihexylamino group, an N-ethyl-N-methylamino group, an N-methyl-N-propylamino group, and the like.

The term "lower alkylsulfonyl group" refers to a substituent formed by the bonding of the above "lower alkyl group" to a sulfur atom in a sulfonyl group, and examples thereof include a methylsulfonyl group, an ethylsulfonyl group, a butylsulfonyl group, and the like.

The term "lower alkylsulfonylamino group" refers to a substituent formed by N-substitution of the above "lower alkylsulfonyl group" to an amino group, and examples thereof include a methylsulfonylamino group, an ethylsulfonylamino group, a butylsulfonylamino group, and the like.

The term "lower alkoxy group" refers to a group formed by the bonding of the "lower alkyl group" to an oxygen atom, and examples thereof include a methoxy group, an ethoxy group, a propoxy group, an isopropoxy group, a butoxy group, an isobutoxy group, a sec-butoxy group, a tert-butoxy group, a pentyloxy group, a neopentyloxy group, a hexyloxy group, an isohexyloxy group, and the like.

The term "lower alkoxycarbonyl group" refers to a group formed by the bonding of the "lower alkoxy group" to a carbonyl group, and specific examples thereof include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, a neopentyloxycarbonyl group, a hexyloxycarbonyl group, an isohexyloxycarbonyl group, and the like.

The term "lower alkoxycarbonylamino group" refers to a group formed by N-substitution of the "lower alkoxycarbonyl group" to an amino group, and specific examples thereof include a methoxycarbonylamino group, an ethoxycarbonylamino group, a propoxycarbonylamino group, an isopropoxycarbonylamino group, a butoxycarbonylamino group, an isobutoxycarbonylamino group, a sec-butoxycarbonylamino group, a tert-butoxycarbonylamino group, a pentyloxycarbonylamino group, a neopentyloxycarbonylamino group, a hexyloxycarbonylamino group, an isohexyloxycarbonylamino group, and the like.

The term "lower alkanoyl group" refers to a group formed by the bonding of the "lower alkyl group" to a carbonyl group, and is preferably a group in which the alkyl group having 1 to 5 carbon atom(s) is bonded to a carbonyl group. For example, an acetyl group, a propionyl group, a butyryl group, an isobutyryl group, a valeryl group, an isovaleryl group, a pivaloyl group, a pentanoyl group, and the like can be included.

The term "lower alkanoyloxy group" refers to a group formed by bonding of the "lower alkanoyl group" to an oxygen atom, and examples thereof include an acetyloxy group, a propionyloxy group, a butyryloxy group, an isobutyryloxy group, a valeryloxy group, an isovaleryloxy group, a pivaloyloxy group, a pentanoyloxy group, and the like.

The term "lower alkylthio group" refers to a substituent formed by the bonding of the "lower alkyl" to a sulfur atom, and examples thereof include a methylthio group, an ethylthio group, a butylthio group, and the like.

As used herein, the term LMOG means a low molecular-mass organic gelator.

As used herein, the term HAS refers to (R)-12-hydroxyoctadecanoic acid.

As used herein, the term SA refers to stearic acid, also known as octadecanoic acid.

As used herein, the term SAFIN refers to self-assembled fibrillar networks.

As used herein, the term critical gelator concentration (CGC) refers to the lowest concentration of LMOG at which a gel is formed at room temperature.

As used herein, the term thixotropy refers to the property of certain gels that are thick (viscous) under normal conditions, but flow (become thin, less viscous) over time when shaken, agitated, or otherwise stressed.

As used herein, the term storage and loss modulus represents the stored energy, representing the elastic portion, and the energy dissipated as heat, representing the viscous portion measured in gels.

As used herein, the term ambidextrous means that the gelator can form hydrogels as well as organogels.

As a result of their potential applications and fundamental importance, gels made with low molecular-mass organic gelators (LMOGs) have experienced increasing interest in recent years.[1] The LMOGs self-assemble primarily by 1D growth modes[2] to form fibers, strands, or tapes via relatively weak physical molecular interactions such as van der Waals forces, intermolecular H bonding, electrostatic forces, π-π stacking, or even London dispersion forces. How these weak physical interactions affect the formation, strength, and stability of a gel must be understood in order to design organogels with the desired properties.

The range of structures known to be LMOGs is extremely broad. It includes molecules as simple as n-alkanes[3-5] (a in FIG. 1) and as complex as substituted steroids or salts made by the addition of two components.[1,6] Thus, London dispersion forces must play a dominant stabilizing role in networks made by the LMOG, n-hexatriacontane (C36),[4] because it lacks the functional groups that are necessary for the other favorable intermolecular interactions. Carboxylic acids with long alkyl chains (e.g., b in FIG. 1), such as stearic acid (SA; i.e., octadecanoic acid), offer the possibility of additional intermolecular interactions (N.B., H bonding) within the LMOG assemblies. In that regard, when cooled below a characteristic temperature (Tg), solutions of relatively high concentrations of long-chained saturated fatty acids and their salts are known to form gelatinous materials with fibrous substructures.[7]

Structure c in FIG. 1 represents LMOGs with two different functional groups attached to an n-alkane. Interesting examples of such LMOGs with secondary amide groups are 11-(butylamido)undecanoic acid,[8] the odium salt of N-octadecyl maleamic acid (a hydrogelator),[9] and N-3-hydroxypropyldodecanamide[10] as well as a naturally occurring carboxylic acid (available from castor oil[11]), 12-hydroxystearic acid (HSA; i.e., 12-hydroxyoctadecanoic acid (FIG. 1)),[12] which is easily obtained as its (R) enantiomer. Enantiopure HSA exhibits circular dichroic signals that are attributed to helical arrangements of the molecules in their fibrillar networks.[12d,12e] Previous reports showed that alkali metal salts of HSA have twisted fibrous networks in their gel state.[12f-12i]

The link between the molecular structure of a gelator and either its efficiency in constructing the self-assembled fibrillar networks (SAFINs) of gels or the nature of those SAFINs is not obvious.[13] Many LMOGs are polymorphous, and it is known that small changes in molecular structure can lead to large changes in crystal packing. For example, primary amides generally form tapelike structures whereas secondary amides form chainlike structures;[14] urea is able to form clathrates in the presence of long n-alkanes, but N,N'-dialkylureas as small as N,N'-dimethylurea organize into fibers and SAFINs, leading to gels.[15] Thus, it is important to investigate the relationship between molecular structure and gelation properties in a series of molecules that differ structurally in a rational way.

Such an investigation is presented here for molecules of the c- and d-types in Scheme 1 using HSA as the base structure. Also, comparisons are made with gels containing LMOGs derived from SA (i.e., b- and e-type molecules that are analogs of HSA in which the 12-hydroxyl group has been removed). The affect of modifying the terminal functional group of HSA on the gelating properties was evaluated by systematically modifying the structure by introducing nitrogen-containing moieties. This data, and the complementary information from the SA analogs, were used to identify the factors that appear to be most important in generating very efficient LMOGs of molecules with long alkyl chains as their primary structural unit. Exemplary derivatives of HSA are amides 1-6 and amines 7-12 and the ammonium carbamate salt of 7, compound 13. The underlying concepts behind the choice of these molecules are that H bonding between amides can be stronger than between amines and that the N-alkyl groups and charged centers at the head groups of 13 can modify the molecular packing of the LMOGs within their fibrillar aggregates. The availability of gelation data from the parent molecule, HSA, and from several nitrogen-containing derivatives of the corresponding acid without a hydroxyl moiety, SA (b- and e-type gelators in FIG. 1), allowed structure-gelation correlations to be derived.

The data demonstrate that the introduction of a 12-hydroxyl group and the presence of a primary amide group increase the efficiency of the gelators. This assessment is based upon gelation temperatures, temporal stabilities (the time between when gels were prepared in sealed containers at ~24° C. and when they undergo visual phase separation or flowed when inverted), critical gelator concentrations (CGCs; the lowest concentrations of LMOG at which a gel is formed at room temperature), and ranges of liquids gelated. The stabilities of the gels are then correlated with the structures of the LMOGs and their SAFINs. Furthermore, some of the gels exhibit exceedingly fast and high degrees of recovery of their viscoelastic properties after their shear-induced destruction; they are thixotropic. Although fast recovery of viscoelasticity has been found in hydrogels where the SAFIN is composed of amorphous objects,[16] we are not aware of other examples in which the fibrillar objects are crystalline and the liquids are organic, as they are here.

Embodiments of various compounds useful as gelling agents, thixotropic gels formed using such gelling agents, products in which such gelling agents can be employed, and methods of using such gelling agents are described below.

In an embodiment, a gelling agent is a compound of formula (I):

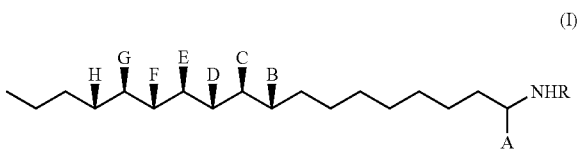

(I)

wherein R is hydrogen or an alkyl group having from 1 to 36 carbon atoms, A is a hydrogen or a carbonyl, and at least one of B, C, D, E, F, G and H is a hydroxy and the others are hydrogen, and salts thereof, wherein the compound is in the (R) form. In another embodiment, R is hydrogen or an alkyl group having from 1 to 18 carbon atoms. In another embodiment, in the compound of formula (I), R is hydrogen or an alkyl group having 1, 2, 3, 4 or 18 carbon atoms. In still another embodiment, only one of B, C, D, E, F, G and H is a hydroxy group and the others are hydrogen.

In another embodiment, a gelling agent is a compound of formula (II):

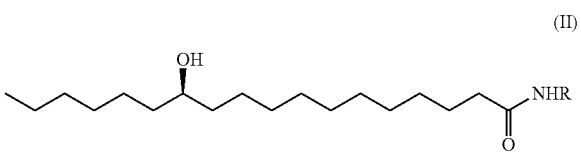

(II)

wherein R is hydrogen or an alkyl group having from 1 to 18 carbon atoms, and salts thereof, wherein the compound is in the (R) form. In yet another embodiment, in the compound of formula (II), R is hydrogen or an alkyl group having 1, 2, 3, 4 or 18 carbon atoms. In still another embodiment, only one of B, C, D, E, F, G and H is a hydroxy group and the others are hydrogen.

In another embodiment, a gelling agent is a compound of formula (III):

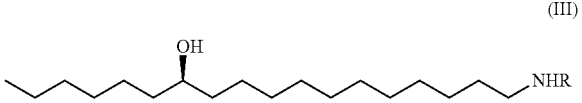

(III)

wherein R is hydrogen or an alkyl group having from 1 to 18 carbon atoms, and salts thereof, wherein the compound is in the (R) form. In still another embodiment, in the compound of formula (III), R is hydrogen or an alkyl group having 1, 2, 3, 4 or 18 carbon atoms. In still another embodiment, only one of B, C, D, E, F, G and H is a hydroxy group and the others are hydrogen.

In an embodiment, a thixotropic gel comprises an organic solvent and a compound of formula (I):

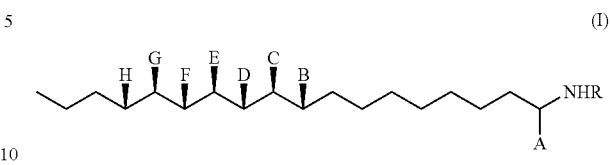

(I)

wherein R is hydrogen or an alkyl group having from 1 to 36 carbon atoms, A is a hydrogen or a carbonyl, and at least one of B, C, D, E, F, G and H is a hydroxy and the others are hydrogen, and salts thereof, wherein the compound is in the (R) form. In another embodiment, R is hydrogen or an alkyl group having from 1 to 18 carbon atoms. In another embodiment, in the compound of formula (I), R is hydrogen or an alkyl group having 1, 2, 3, 4 or 18 carbon atoms. In still another embodiment, only one of B, C, D, E, F, G and H is a hydroxy group and the others are hydrogen. In an embodiment, the gel is formed from at least one solvent is selected from the group consisting of n-hexane, n-octane, n-decane, silicone oil, methanol, 1-butanol, 1-octanol, benzyl alcohol, chlorobenzene, chloroform, carbon tetrachloride, benzene, toluene, dimethylsulfoxide, acetonitrile and combinations thereof.

In an embodiment, in the above gel, the compound of formula (I) is present at a concentration of about 20% or less, on a weight/weight basis. In another embodiment, the compound of formula (I) is present at a concentration of about 10%, on a weight/weight basis, in the above gel. In yet another embodiment, the compound of formula (I) is present at a concentration of about 5% or less, n a weight/weight basis, in the above gel. In another embodiment, the compound of formula (I) is present at a concentration of about 2%, on a weight/weight basis, in the above gel. In yet another embodiment, the compound of formula (I) is present at a concentration of about 2% or less, on a weight/weight basis, in the above gel. In another embodiment, the compound of formula (I) is present at a concentration of about 0.5%, on a weight/weight basis, in the above gel. In yet another embodiment, the compound of formula (I) is present at a concentration of about 0.2% or less, n a weight/weight basis, in the above gel.

In yet another embodiment, the above gel recovers at least about 80% of its viscoelasticity within less than about one minute, preferably within less than about 30 seconds, and more preferably within less than about 15 seconds after exposure to destructive shear. In still another embodiment, the gel recovers at least about 90% of its viscoelasticity within less than about one minute, preferably within less than about 30 seconds, and more preferably within less than about 15 seconds after exposure to destructive shear. In a further embodiment, the gel recovers at least about 95% of its viscoelasticity within less than about one minute, preferably within less than about 30 seconds, and more preferably within less than about 15 seconds after exposure to destructive shear.

In a still further embodiment, the gel recovers at least about 98% of its viscoelasticity within less than about one minute, preferably within less than about 30 seconds, and more preferably within less than about 15 seconds after exposure to destructive shear.

In an embodiment, a thixotropic gel comprises at least one solvent and a compound of formula (II) or formula (III):

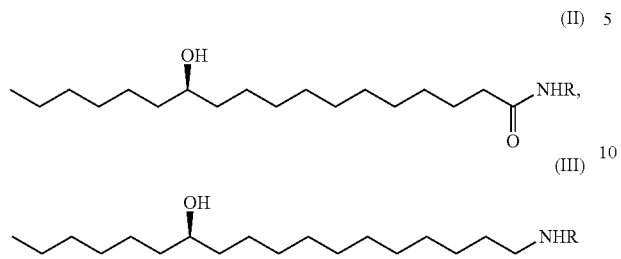

wherein R is hydrogen or an alkyl group having from 1 to 18 carbon atoms, and salts thereof, wherein the compound is in the (R) form. In an embodiment, the gel is formed from at least one solvent is selected from the group consisting of n-hexane, n-octane, n-decane, silicone oil, methanol, 1-butanol, 1-octanol, benzyl alcohol, chlorobenzene, chloroform, carbon tetrachloride, benzene, toluene, dimethylsulfoxide, acetonitrile and combinations thereof.

In an embodiment, in the above gel, the compound of formula (II) or (III) is present at a concentration of about 20% or less, on a weight/weight basis. In another embodiment, the compound of formula (II) or (III) is present at a concentration of about 10%, on a weight/weight basis, in the above gel. In yet another embodiment, the compound of formula (II) or (III) is present at a concentration of about 5% or less, n a weight/weight basis, in the above gel. In another embodiment, the compound of formula (II) or (III) is present at a concentration of about 2%, on a weight/weight basis, in the above gel. In yet another embodiment, the compound of formula (II) or (III) is present at a concentration of about 2% or less, on a weight/weight basis, in the above gel. In another embodiment, the compound of formula (II) or (III) is present at a concentration of about 0.5%, on a weight/weight basis, in the above gel. In yet another embodiment, the compound of formula (II) or (III) is present at a concentration of about 0.2% or less, n a weight/weight basis, in the above gel.

In yet another embodiment, the above gel recovers at least about 80% of its viscoelasticity within less than about one minute, preferably within less than about 30 seconds, and more preferably within less than about 15 seconds after exposure to destructive shear. In still another embodiment, the gel recovers at least about 90% of its viscoelasticity within less than about one minute, preferably within less than about 30 seconds, and more preferably within less than about 15 seconds after exposure to destructive shear. In a further embodiment, the gel recovers at least about 95% of its viscoelasticity within less than about one minute, preferably within less than about 30 seconds, and more preferably within less than about 15 seconds after exposure to destructive shear.

In a still further embodiment, the gel recovers at least about 98% of its viscoelasticity within less than about one minute, preferably within less than about 30 seconds, and more preferably within less than about 15 seconds after exposure to destructive shear.

In an embodiment, 12-hydroxy-N-alkyloctadecanamides are manufactured by (a) adding a solution of 12-hydroxystearamide and triethylamine in a dry non-reactive solvent to a solution of ethyl chloroformate in a dry non-reactive solvent while maintaining the temperature at about 0° C.; and (b) adding an alkyl amine to the solution obtained in step (a).

In another embodiment, 1-(alkylamino)octadecan-12-ols are manufactured by adding LAH to a suspension of suspension of a 12-hydroxy-N-alkyloctadecanamide in a dry non-reactive solvent under an inert atmosphere.

In an embodiment, a pharmaceutical composition comprises an active pharmaceutical ingredient and a compound of formula (I)

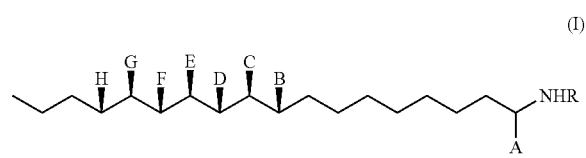

wherein R is hydrogen or an alkyl group having from 1 to 36 carbon atoms, A is a hydrogen or a carbonyl, and at least one of B, C, D, E, F, G and H is a hydroxy group and the others are hydrogen, and salts thereof, wherein the compound is in the (R) form, and a pharmaceutically acceptable carrier. In another embodiment, R is hydrogen or an alkyl group having from 1 to 18 carbon atoms. In another embodiment, in the compound of formula (I), R is hydrogen or an alkyl group having 1, 2, 3, 4 or 18 carbon atoms. In still another embodiment, only one of B, C, D, E, F, G and H is a hydroxy group and the others are hydrogen.

In another embodiment, a processed food composition comprises a food and a compound of formula (I):

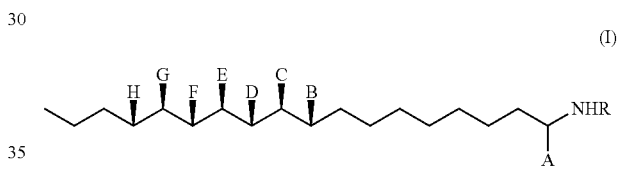

wherein R is hydrogen or an alkyl group having from 1 to 36 carbon atoms, A is a hydrogen or a carbonyl, and at least one of B, C, D, E, F, G and H is a hydroxy and the others are hydrogen, and salts thereof, wherein the compound is in the (R) form. In another embodiment, R is hydrogen or an alkyl group having from 1 to 18 carbon atoms. In another embodiment, in the compound of formula (I), R is hydrogen or an alkyl group having 1, 2, 3, 4 or 18 carbon atoms. In still another embodiment, only one of B, C, D, E, F, G and H is a hydroxy group and the others are hydrogen.

In another embodiment, a cosmetic composition comprising at least one cosmetically acceptable ingredient and a compound of formula (I):

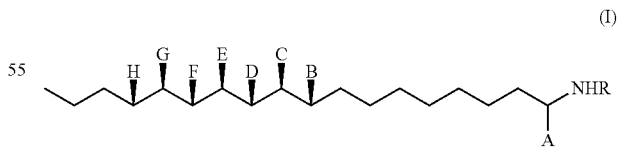

wherein R is hydrogen or an alkyl group having from 1 to 36 carbon atoms, A is a hydrogen or a carbonyl, and at least one of B, C, D, E, F, G and H is a hydroxy and the others are hydrogen, and salts thereof, wherein the compound is in the (R) form, and a cosmetically acceptable carrier. In another embodiment, R is hydrogen or an alkyl group having from 1 to 18 carbon atoms. In another embodiment, in the compound of formula (I), R is hydrogen or an alkyl group having 1, 2, 3, 4 or 18 carbon atoms. In still another embodiment, only one of B, C, D, E, F, G and H is a hydroxy group and the others are hydrogen.

In an embodiment, a consumer product comprises a compound of formula (I):

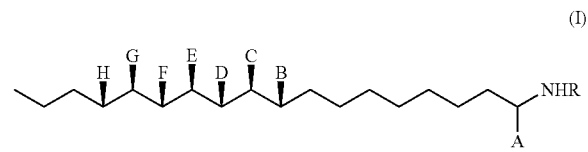

wherein R is hydrogen or an alkyl group having from 1 to 36 carbon atoms, A is a hydrogen or a carbonyl, and at least one of B, C, D, E, F, G and H is a hydroxy and the others are hydrogen, and salts thereof, wherein the compound is in the (R) form, and an acceptable medium. In another embodiment, R is hydrogen or an alkyl group having from 1 to 18 carbon atoms. In another embodiment, in the compound of formula (I), R is hydrogen or an alkyl group having 1, 2, 3, 4 or 18 carbon atoms. In still another embodiment, only one of B, C, D, E, F, G and H is a hydroxy group and the others are hydrogen.

In an embodiment, a method for containing an unintentional chemical release, comprises forming a gel a compound of formula (I):

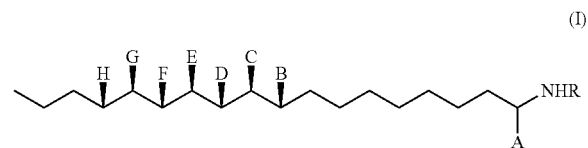

wherein R is hydrogen or an alkyl group having from 1 to 36 carbon atoms, A is a hydrogen or a carbonyl, and at least one of B, C, D, E, F, G and H is a hydroxy and the others are hydrogen, and salts thereof, wherein the compound is in the (R) form with the chemical that was unintentionally released. In another embodiment, R is hydrogen or an alkyl group having from 1 to 18 carbon atoms. In another embodiment, in the compound of formula (I), R is hydrogen or an alkyl group having 1, 2, 3, 4 or 18 carbon atoms. In still another embodiment, only one of B, C, D, E, F, G and H is a hydroxy group and the others are hydrogen.

In another embodiment, at least one compound of formula (II) or (III) is used as the compound of formula (I) in any of the above embodiments.

In an embodiment, a gelling agent is a compound of formula (IV):

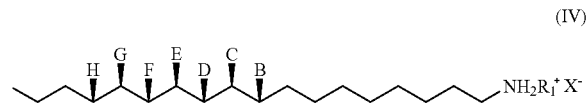

wherein n is an integer from 0 to 6, X is an anion, A is a hydrogen or a carbonyl, and at least one of B, C, D, E, F, G and H is a hydroxy and the others are hydrogen, and the compound is in the (R) form, wherein the compound forms an organogel or a hydrogel upon mixing with an organic solvent or an aqueous solution. In another embodiment, the anion is selected from the group consisting of chlorine, bromine, iodine, nitrate, boron trifluoride, acetate, nonanoate and oxalate.

In an embodiment, a thixotropic gel comprises an organic solvent and a compound of formula (IV):

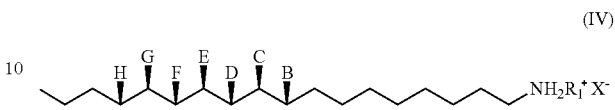

wherein n is an integer from 0 to 6, X is an anion, A is a hydrogen or a carbonyl, and at least one of B, C, D, E, F, G and H is a hydroxy and the others are hydrogen, and the compound is in the (R) form. In another embodiment, only one of B, C, D, E, F, G and H is a hydroxy group and the others are hydrogen. In an embodiment, the anion is selected from the group consisting of chlorine, bromine, iodine, nitrate, boron trifluoride, acetate, nonanoate and oxalate. In another embodiment, the at least one solvent is selected from the group consisting of n-hexane, n-octane, n-decane, silicone oil, methanol, 1-butanol, 1-octanol, benzyl alcohol, chlorobenzene, chloroform, carbon tetrachloride, n-perfluorooctane, benzene, toluene, dimethylsulfoxide, acetonitrile and water.

In an embodiment, in the above gel, the compound of formula (IV) is present at a concentration of about 20% or less, on a weight/weight basis. In another embodiment, the compound of formula (IV) is present at a concentration of about 10%, on a weight/weight basis, in the above gel. In yet another embodiment, the compound of formula (IV) is present at a concentration of about 5% or less, n a weight/weight basis, in the above gel. In another embodiment, the compound of formula (IV) is present at a concentration of about 2%, on a weight/weight basis, in the above gel. In yet another embodiment, the compound of formula (IV) is present at a concentration of about 2% or less, on a weight/weight basis, in the above gel. In another embodiment, the compound of formula (IV) is present at a concentration of about 0.5%, on a weight/weight basis, in the above gel. In yet another embodiment, the compound of formula (IV) is present at a concentration of about 0.2% or less, n a weight/weight basis, in the above gel.

In yet another embodiment, the gel recovers at least about 80% of its viscoelasticity within less than about one minute, preferably within less than about 30 seconds, and more preferably within less than about 15 seconds after exposure to destructive shear. In still another embodiment, the gel recovers at least about 90% of its viscoelasticity within less than about one minute, preferably within less than about 30 seconds, and more preferably within less than about 15 seconds after exposure to destructive shear. In a further embodiment, the gel recovers at least about 95% of its viscoelasticity within less than about one minute, preferably within less than about 30 seconds, and more preferably within less than about 15 seconds after exposure to destructive shear.

In a still further embodiment, the gel recovers at least about 98% of its viscoelasticity within less than about one minute, preferably within less than about 30 seconds, and more preferably within less than about 15 seconds after exposure to destructive shear.

In an embodiment, a pharmaceutical composition comprises an active pharmaceutical ingredient and a compound of formula (IV):

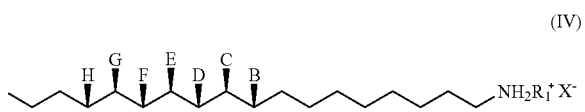

(IV)

wherein n is an integer from 0 to 6, X is an anion, A is a hydrogen or a carbonyl, and at least one of B, C, D, E, F, G and H is a hydroxy anal the others are hydrogen, and the compound is in the (R) form, and a pharmaceutically acceptable carrier. In another embodiment, only one of B, C, D, E, F, G and H is a hydroxy group and the others are hydrogen.

In an embodiment, a processed food composition comprises a food and a compound of formula (IV):

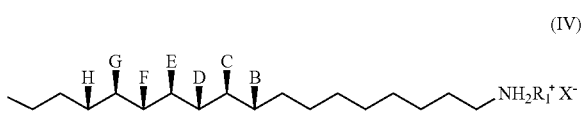

(IV)

wherein n is an integer from 0 to 6, X is an anion, A is a hydrogen or a carbonyl, and at least one of B, C, D, E, F, G and H is a hydroxy and the others are hydrogen, and the compound is in the (R) form, wherein the compound is in the (R) form. In still another embodiment, only one of B, C, D, E, F, G and H is a hydroxy group and the others are hydrogen.

In an embodiment, a cosmetic composition comprises at least one cosmetically acceptable ingredient and a compound of formula (IV):

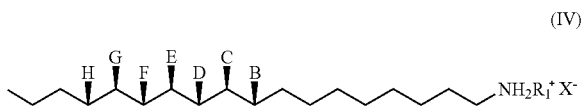

(IV)

wherein n is an integer from 0 to 6, X is an anion, A is a hydrogen or a carbonyl, and at least one of B, C, D, E, F, G and H is a hydroxy and the others are hydrogen, and the compound is in the (R) form, wherein the compound is in the (R) form, and a cosmetically acceptable carrier. In still another embodiment, only one of B, C, D, E, F, G and H is a hydroxy group and the others are hydrogen.

In an embodiment, a consumer product comprises a compound of formula (IV):

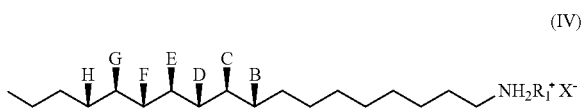

(IV)

wherein n is an integer from 0 to 6, X is an anion, A is a hydrogen or a carbonyl, and at least one of B, C, D, E, F, G and H is a hydroxy and the others are hydrogen, and the compound is in the (R) form, wherein the compound is in the (R) form, and an acceptable medium. In still another embodiment, only one of B, C, D, E, F, G and H is a hydroxy group and the others are hydrogen.

In an embodiment, a method for containing an unintentional chemical release, comprises forming a gel a compound of formula (IV):

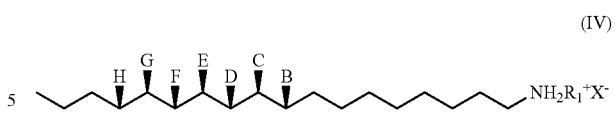

(IV)

wherein n is an integer from 0 to 6, X is an anion, A is a hydrogen or a carbonyl, and at least one of B, C, D, E, F, G and H is a hydroxy and the others are hydrogen, and the compound is in the (R) form, wherein the compound is in the (R) form, with the chemical that was unintentionally released. In still another embodiment, only one of B, C, D, E, F, G and H is a hydroxy group and the others are hydrogen.

The group $R^1$ in the compounds of formula (IV) can be covalently attached to the nitrogen atom or can be present as the counterion of the positively charged portion of the salt.

The present disclosure will be further understood with reference to the following non-limiting examples.

EXAMPLES

Instrumentation and Procedures $^1$H-NMR spectra were recorded on a Varian 300 MHz spectrometer interfaced to a Sparc UNIX computer using Mercury software. Chemical shifts were referenced to an internal standard, tetramethylsilane (TMS). IR spectra were obtained on a Perkin-Elmer Spectrum One FTIR spectrometer interfaced to a personal computer. Elemental analyses were performed on a Perkin-Elmer 2400 CHN elemental analyzer using acetanilide as a calibration standard. Melting points and optical micrographs (POMs) were recorded on a Leitz 585 SM-LUX-POL microscope equipped with crossed polars, a Leitz 350 heating stage, a Photometrics CCD camera interfaced to a computer, and an Omega HH503 microprocessor thermometer connected to a J-K-T thermocouple. The samples for POM were flame sealed in 0.4 or 0.5 mm pathlength, flattened Pyrex capillary tubes (VitroCom) heated to their liquid phase in a boiling water bath and cooled according to protocols described below.

Powder X-ray diffraction (XRD) patterns of samples were obtained on a Rigaku R-AXIS image plate system with Cu Ka X-rays (A=1.54 A) generated by a Rigaku generator operating at 46 kV and 40 mA with the collimator at 0.5 mm (to obtain 0.5-mm-diameter beams of X-rays17). Data processing and analyses were performed using Materials Data JADE (version 5.0.35) XRD pattern processing software. Samples were sealed in 0.5 mm glass capillaries (W. Müller, Schönwalde, Germany), and diffraction data were collected for 2 hours (neat powders) or 10 hours (gels).

Differential scanning calorimetry (DSC) and thermogravimetric analyses (TGA) were performed on a TA 2910 differential scanning calorimeter interfaced to a TA Thermal Analyst 3100 controller under a slow stream of nitrogen flowing through the cell. Samples were in closed aluminum pans for DSC and in open ones for TGA measurements. Transition temperatures from DSC ($T_m$) are reported at the onsets of endotherms (on heating) and exotherms (on cooling). Heating rates were 5° C./min; cooling rates were variable and depended on the difference between the cell block and ambient temperature.

Rheological measurements were obtained on an Anton Paar Physica MCR 301 rheometer using Peltier controlled parallel plates (25 mm diameter). The gap between the parallel plates was 0.5 mm unless indicated otherwise, and the data were collected using Rheoplus/32 Service V3.10 software. Before data were recorded, each sample was placed between the shearing plates of the rheometer and heated to 120° C. to ensure that a solution/sol was present. It was cooled to 10° C. (at ~20° C. min$^{-1}$), the temperature was increased to 25° C., and the sample was incubated there for 15 min to reform the gel and remove any shear-induced alignment of the fibers of SAFIN.

Scanning electron microscopy (SEM) images were recorded with 2-30 kV electron beam energies on a Zeiss Supra 55 VP electron scanning microscope. Samples for SEM were prepared by placing the gel sample on an Al mount (1/200 slotted head, 1/800 pin, Ted Pella, Inc.) and allowing the solvent to evaporate at 24° C. for 24 h. No metal coating was applied.

Example 1

Preparation of Gelling Agents

Materials. Silicone oil (tetramethyltetraphenylsiloxane, Dow silicone oil 704 from Dow Chemical Company, Midland, Mich.) was used as received. Solvents for syntheses and other liquids for gelation studies were reagent grade or better (Aldrich). Anhydrous THF (Acros Chemicals), LiAlH$_4$ (LAH, 95%, Aldrich), triethylamine (99.5%, Aldrich), NH$_4$OH (ACS reagent, Fisher), and stearic acid (Aldrich, 99%) were used as received. Thionyl chloride (>99%, Aldrich) was distilled immediately before use. Dry CO$_2$ was prepared by passing gas formed from dry ice through an anhydrous calcium sulfate (Drierite) tube. Methylamine (2 M solution in THF, Aldrich), ethylamine (2 M solution in THF, Aldrich) and butylamine (99.5%, Aldrich) were used as received. 1-Octadecylamine (Aldrich) was purified by collecting a center fraction from two distillations under reduced pressure at 160-165° C. (1 torr) and was stored under a nitrogen atmosphere at 5-6° C.

Purification of HSA. Commercial HSA (25 g; mp: 58.6-80.3° C., Arizona Chemicals) was dissolved in 300 mL of a warm 1:19 (v:v) mixture of ethyl acetate:hexane. The solution was then allowed to cool very slowly while being stirred vigorously to avoid gelation. This procedure was repeated twice more to yield 17 g of HSA, mp 80.2-82.1° C. (lit$^1$ 80.5-81.0° C.).

$^1$H-NMR (CDCl$_3$, 300 (MHz): δ 0.91 (t, 3H, CH$_3$, J=6.2 Hz), 1.3-1.45 (m, 26H, —CH$_2$) 1.68 (m, 2H, —CH$_2$), 2.37 (t, 2H, CH$_2$—CO$_2$H, J=7.2 Hz), 3.6 (m, 1H, CH—OH); elemental analysis; calcd for C$_{18}$H$_{36}$O$_3$; C, 71.95; H, 12.08. Found C, 72.22; H, 12.14. [α]$^D$-0.49° (0.141 g/mL, pyridine).$^2$ (lit$^1$ [α]$^D$-0.41° (0.168 g/mL, pyridine)

Stearamide (8). The amide was prepared by a common recipe. Thionyl chloride (0.6 g, 6 mmol) was slowly added to stearic acid (1.0 g, 3.5 mmol) and the mixture was heated at 55° C. for 2 h under a dry atmosphere. Excess thionyl chloride was removed by distillation and the remaining liquid (stearoyl chloride) was slowly added to 15 mL of an aqueous 30% ammonia solution at 0° C. The precipitate that formed was collected by vacuum filtration and was recrystallized from ethyl acetate to yield 0.7 g (70%) of product, mp 108.6-109.0° C. (lit$^4$ 108.4° C.).

12-Hydroxystearamide (1). The preparation of 1 was performed according to a literature procedure. Ethyl chloroformate (18.0 g, 166 mmol) was added slowly to cooled (<0° C.); dry THF (100 mL) stirred under a nitrogen atmosphere. The mixture was stirred for 20 more min followed by slow addition of HSA (10.0 g, 33 mmol) and triethylamine (2.3 g, 33 mmol) in dry THF (50 mL) while maintaining the temperature below 0° C. The contents were stirred for another 30 min and a stream of anhydrous ammonia gas (prepared from an NH$_4$OH solution (50 mL) in a hot (ca 60° C.) water bath; the gas was passed through a 50×2 cm column filled with anhydrous Drierite and ca 20 g of activated CaO powder (prepared by heating CaCO$_3$ to ca 500° C. for 30 min and cooling in a desiccator under a nitrogen atmosphere) was bubbled rapidly through the solution for 10 min. The mixture was kept for 12 h without stirring, during which time the temperature slowly rose to room temperature. The solvent was removed by distillation and the residue, after being dissolved in ethyl acetate (200 mL), was washed successively with 3 N aq HCl (3×15 mL), aqueous 1 M Na$_2$CO$_3$ (3×15 mL), and brine (3×10 mL). During these washings, the amide in the organic phase formed a gel which was destroyed by warming the outer surface of the separatory funnel. The organic part was collected, dried with anhydrous sodium sulfate, decanted while hot, and then slowly cooled to 0° C. with vigorous stirring. The precipitate that formed was collected by filtration. This process was repeated once and the solid was dried in vacuo at 55-60° C. for 12 h to yield 9.3 g (94%), mp 113.1-113.7° C. (lit$^6$ 111-112° C.).

IR (neat): 3412, 3302, 3209 (NH and OH), 2913, 2848 (CH), 1650 (CO) cm$^{-1}$; $^1$H-NMR (CDCl$_3$, 300 (MHz): δ 0.92 (t, 3H, CH$_3$, J=6.1 Hz), 1.3-1.6 (m, 30 H, CH$_2$), 2.2 (2H, t, CH$_2$—CO, J=7.1 Hz), 3.61 (1H, m, CH—OH), 5.4 (2H, br, CONH$_2$); elemental analysis; calcd for C$_{18}$H$_{37}$NO$_2$; C, 72.19; H, 12.45; N, 4.68; O, 10.68. Found C, 72.55; H, 12.57; N, 4.97.

1-Aminooctadecan-12-ol (7) and its ammonium carbamate salt (13). LAH (5.0 g, 130 mmol) was slowly added to a stirred suspension of 1 (5.0 g, 17 mmol) in dry THF (250 mL) under a nitrogen atmosphere. Then, the mixture was heated to reflux and the gel that formed was broken with a spatula. Refluxing was continued overnight, excess LAH was destroyed by successively adding (very slowly; Caution: exothermic reaction.) 6 mL of water, 6 mL of aq 15% NaOH, and 12 mL of water. The mixture was filtered, and the filtrate was concentrated and dissolved in 30 mL of ethyl acetate. A precipitate that formed as the ethyl acetate solution was cooled to 0° C. was separated by filtration and recrystallized from ethyl acetate to afford 4.5 g (94%) of amine-7, mp 60.0-61.5° C. IR (neat): 3303, 3209 (NH and OH), 2955, 2913, 2848 (CH) cm$^{-1}$; $^1$H-NMR (CDCl$_3$, 300 (MHz): δ 0.91 (t, 3H, CH$_3$, J=6.2 Hz), 1.3-1.5 (32 H, m, CH$_2$), 2.7 (2H, t, CH$_2$—NH$_2$, J=6.9 Hz), 3.63 (1H, m, CH—OH). Elemental analysis; calcd for 12-hydroxystearamine monohydrate; C, 71.28; H, 13.53; N, 4.62. Found C, 71.78; H, 13.40; N, 4.64. Thermal gravimetric analysis (TGA) showed a weight loss between room temperature and 103° C. of 5.7% (FIG. 46); 5.9% calculated for loss of one molecule of water.

The ammonium carbamate salt (13) was prepared by bubbling CO$_2$ gas through a chloroform solution of the amine 13 for 20 min. The salt precipitated quantitatively and was collected by filtration: mp 77.7-80.0° C. on first heating; 59.2-61.2° C. on second heating (corresponding to regeneration of 7). TGA of 13 showed a weight loss of 6.6% between room temperature and 103° C. (FIG. 47); 6.7% is the calculated weight loss for one molecule of carbon dioxide.

Preparation of 12-Hydroxy-N-alkyloctadecanamides

12-Hydroxy-N-alkyloctadecanamides were prepared by the following procedure. To a cooled (at 0° C.) and vigorously stirred solution of ethyl chloroformate (18.0 g, 166 mmol) in dry THF (50 mL) was added slowly a solution of HSA (10.0 g, 33 mmol) and triethylamine (2.3 g, 33 mmol) in dry THF (50 mL) while maintaining the temperature at 0° C. The mixture was stirred for an additional 20 min. An alkyl amine (33 mmol) in 50 mL dry THF was added to the solution at 0° C., and the reaction mixture was kept at room temperature for 24 h. The solvent was removed under vacuum and the residue was dissolved in ethyl acetate (50 mL), washed successively with 3N HCl (3×15 mL), aqueous 1M $Na_2CO_3$ (3×15 mL), and water (50 mL). The organic layer was dried over sodium sulfate and the residue, after evaporation, was recrystallized from ethyl acetate.

12-Hydroxy-N-methyloctadecanamide (2): 49% yield; mp 108.2-108.8° C.; 1H-NMR ($CDCl_3$, 300 (MHz): δ 0.91 (t, 3H, $CH_3$, J=6.8 Hz), 1.2-1.6 (m, 28 H, —$CH_2$), 2.15 (t, 2H, —$CH_2$—CO—, J=7.6 Hz), 2.81 (d, 3H, $CH_3$, J=4.8 Hz), 3.58 (m, 1H, —CH—OH), 5.4 (br, 1H, —NH—); elemental analysis calcd for $C_{19}H_{39}NO_2$; C, 72.79; H, 12.34; N, 4.38; O, 10.21. Found C, 72.63; H, 12.34; N, 4.38.

12-Hydroxy-N-ethyloctadecanamide (3): 93% yield; mp 111.0-111.3° C.; 1H-NMR ($CDCl_3$, 300 (MHz): δ 0.91 (t, 3H, $CH_3$, J=6.8 Hz), 1.13 (t, 3H, J=7.2 Hz) 1.2-1.6 (m, 26H, —$CH_2$), 2.17 (t, 2H, —$CH_2$—CO—, J=7.5 Hz), 3.21-3.28 (q, 2H, —CH—NH, J=7.2 Hz) 3.58 (m, 1H, —CH—OH), 5.3 (br, 1H, —NH—), elemental analysis calcd for $C_{20}H_{41}NO_2$; C, 73.34; H, 12.62; N, 4.28; O, 9.77. Found C, 73.33; H, 12.48; N, 4.29.

12-Hydroxy-N-propyloctadecanamide (4): 93% yield; mp 107.3-107.4° C.; 1H-NMR ($CDCl_3$, 300 (MHz): δ 0.91 (m 6H, $CH_3$) 1.2-1.6 (m, 28H, —$CH_2$), 2.17 (t, 2H, —$CH_2$—CO—, J=7.5 Hz), 3.21-3.28 (q, 2H, —CH—NH, J=7.2 Hz) 3.59 (m, 1 H, —CH—OH), 5.3 (br, 1H, —NH—); elemental analysis calcd for $C_{21}H_{43}NO_2$; C, 73.84; H, 12.69; N, 4.10; O, 9.37. Found C, 74.16; H, 12.95; N, 4.33.

12-Hydroxy-N-butyloctadecanamide (5): 94% yield; mp 104.1-104.6° C.; 1H-NMR ($CDCl_3$, 300 (MHz): δ 0.92 (m, 6H, $CH_3$), 1.2-1.6 (m, 30H, —$CH_2$), 2.17 (t, 2H, —$CH_2$—CO—, J=7.4 Hz), 3.21-3.27 (q, 2H, —CH—NH, J=7.2 Hz), 3.59 (m, 1 H, —CH—OH), 5.3 (br, 1H, —NH—). elemental analysis calcd for $C_{19}H_{39}NO_2$; C, 74.31; H, 12.76; N, 3.94; O, 9.00. Found C, 73.85; H, 12.61; N, 3.92.

12-Hydroxy-N-octadecyloctadecanamide (6): 47% yield; mp 106.9-107.3° C.; 1H-NMR ($CDCl_3$, 300 (MHz): δ 0.92 (m, 6H, $CH_3$), 1.2-1.6 (m, 60H, —CH2), 2.17 (t, 2H, —$CH_2$—CO—, J=7.4 Hz), 3.21-3.27 (q, 2H, —CH—NH, J=7.2 Hz), 3.59 (m, 1 H, —CH—OH), 5.3 (br, 1H, —NH—); elemental analysis calcd for $C_{36}H_{73}NO_2$; C, 78.33; H, 13.33; N, 2.54; O, 5.80. Found C, 78.88; H, 13.65; N, 2.76.

Preparation of 1-(Alkylamino)octadecan-12-ols 1-(Alkylamino)octadecan-12-ols were prepared by the following procedure. LAH (3.0 g, 79 mmol) was added slowly to a stirred suspension of a 12-hydroxy-N-alkyloctadecanamide (15 mmol) in dry THF (200 mL) under a nitrogen atmosphere. Then, the mixture was refluxed overnight, excess LAH was destroyed by successively adding very slowly a total of 3 mL of water in small amounts, 15% aq NaOH solution (a total of 3 mL), and 3 mL of water. The mixture was filtered and the filter pad was washed with THF. The combined liquids were concentrated on a rotary evaporator and dissolved in ethyl acetate (30 mL). The amine that precipitated upon cooling the ethyl acetate solution to 0° C. was recrystallized from ethyl acetate and hexane mixture (1:4).

1-(Methylamino)octadecan-12-ol (8). 91% yield; mp 88.0-88.5° C.; 1H-NMR ($CDCl_3$, 300 (MHz): δ 0.89 (t, 3H, $CH_3$, J=6.0*Hz), 1.2-1.6 (m, 30H, —$CH_2$), 2.4, (s, 3H, $CH_3$), 2.55 (t, 2H, —$CH_2$—NH—, J=6.8 Hz), 3.6 (m, 1H, —CH—OH). elemental analysis calcd for $C_{19}H_{41}NO$; C, 76.19; H, 13.80; N, 4.68; O, 5.34. Found C, 76.27; H, 13.80; N, 4.52.

1-(Ethylamino)octadecan-12-ol (9). 92% yield; mp 84.3-84.8° C.; 1H-NMR ($CDCl_3$, 300 (MHz): δ 0.9 (t, 3H, CH3, J=6.0 Hz), 1.1 (t, 3H, $CH_3$, J=6.8 Hz) 1.2-1.6 (m, 30 H, —$CH_2$), 2.6 (m, 4H, —$CH_2$—NH—), 3.6 (m, 1H, —CH—OH). elemental analysis calcd for $C_{20}H_{43}$ NO; C, 76.61; H, 13.82; N, 4.47; O, 5.10. Found C, 76.78; H, 13.85; N, 4.46.

1-(Propylamino)octadecan-12-ol (10). 92% yield; mp 87.6-88.0° C.; 1H-NMR ($CDCl_3$, 300 (MHz): δ 0.93 (m, 6H, $CH_3$), 1.2-1.6 (m, 32 H, —$CH_2$), 2.6 (m, 4H, —$CH_2$—NH—), 3.6 (m, 1H, —CH—OH); elemental analysis calcd for $C_{21}H_{45}NO$; C, 76.99; H, 13.85; N, 4.28; O, 4.88. Found C, 77.51; H, 14.41; N, 4.52.

1-(Butylamino)octadecan-12-ol (11). Yield 65%; mp 89.3-89.8° C.; 1H-NMR ($CDCl_3$, 300 (MHz): δ 0.92 (m, 6H, $CH_3$), 1.2-1.6 (m, 34 H, —$CH_2$), 2.6 (m, 4H, —$CH_2$—NH—), 3.59 (m, 1H, —CH—OH). elemental analysis calcd for $C_{22}H_{47}NO$; C, 77.35; H, 13.87; N, 4.10; O, 4.68. Found C, 77.45; H, 13.95; N, 4.12.

1-(Octadecylamino)octadecan-12-ol (12). Yield 96%; mp 92.8-93.4° C.; 1H-NMR ($CDCl_3$, 300 (MHz): δ 0.92 (m, 6H, CH3), 1.2-1.6 (m, 64 H, —$CH_2$), 2.6 (m, 4H, —$CH_2$—NH—), 3.59 (m, 1H, —CH—OH); elemental analysis calcd for $C_{36}H_{75}NO$; C, 80.37; H, 14.05; N, 2.60; O, 2.97. Found C, 79.69; H, 14.51; N, 2.82.

Example 2

Fast and Slow Cooling Procedures for the Preparation of Gels from Sols and Analyses of Gels Fast-cooled gels were prepared by placing weighed amounts of a liquid and gelator into a glass tube (5 mm i.d.) that was then flame-sealed. The mixture was heated to ca. 80° C. in a water bath (or to 110° C. in an oil bath with 1) until a solution/sol was obtained and was then placed directly into an ice-water bath for 10 min. After the sample was warmed to room temperature for 1 h, its appearance was noted. Slow-cooled gels were prepared using the protocol above except that the hot solutions/sols were kept in the water or oil bath while they returned slowly to room temperature.

Example 3

Temperatures of Gelation and Critical Gelation Concentrations (CGC)

Gelation temperatures (Tg) were determined by the inverse flow method[18] (i.e., the temperature ranges over which a gel fell under the influence of gravity when inverted in a sealed glass tube that was placed in a water bath that was heated from room temperature at ca. 1.5° C. $min^{-1}$). CGCs were determined from a series of fast-cooled gels with different LMOG concentrations; the concentration of the one with the lowest gelator concentration that did not fall when inverted at 24° C. is reported.

The gelation properties of 2 wt % HSA and compounds 1-13 in a wide range of liquids are summarized in Tables 1 and 2.

SAFIN (self-assembled fibrillar networks) structures of HSA organogels have been studied extensively and head-to-head contacts between carboxylic acid groups have been shown to promote the formation of multiple hydrogen-bonded sequences and aid fiber stability. The Tg values of 2 wt % HSA and an n-alkane with an even number of carbon atoms are slightly higher than those with odd-numbered n-alkane liquids, but all were opaque in appearance. The dependence of the SAFINs of the HSA gels on the liquid component is apparent when silicone oil and n-alkanes are compared: at one LMOG concentration, the silicone oil gel has a higher Tg than the n-alkane gels. Also, the sodium salt of HSA has been found to gelate n-dodecane at 4 wt %, and as little as 0.5 wt % was able to gelate chloroform and carbon tetrachloride.[20]

Intermolecular H-bonding interactions between primary or secondary amide functional groups can be stronger than between two carboxylic acid groups.[21] Thus, the Tg of n-alkane or silicone oil gels is higher when the LMOG was one of the amides, 1-6, than when it was HSA. Removal of the 12-hydroxyl group from 1 yields octadecanamide (14), which, in contrast to SA, is an excellent gelator. However, whereas 2 wt % 1 is a better gelator of lower-polarity liquids and forms solutions with low molecular-mass alcohols, the same concentration of 14 is a more efficient LMOG of higher-polarity liquids and precipitates from n-alkanes.

TABLE 1

Appearances,[a] $T_g$ Values (° C.), and Periods of Stability[b] (in Parentheses) of Gels Containing 2 wt % HSA and Its Amide Derivatives (1-6) in Various Liquids

| liquid | HSA | 1 | 2 | 3 | 4 | 5 | 6 |
|---|---|---|---|---|---|---|---|
| n-hexane | OG (59-60, 2 m) | OG (syn, 91-92,[c] 4 m) | OG (syn, 82-83, >3 w) | OG (syn, 81,[c] >1 m) | OG (syn, 82,[c] 2 m) | OG (syn, 74-75,[c] >1 m) | OG (syn, 78,[c] 2 m) |
| n-octane | OG (60-62, >9 m[d]) | OG (94-95,[c] 4 m) | OG (84-85,[c] >3 w) | OG (84,[c] >1 m) | OG (syn, >90,[c] 5 m) | OG (74,[c] >1 m) | OG (syn, 81,[c] 2 m) |
| n-decane | OG (64-65, >9 m) | OG (95-96,[c] >1 y) | OG (>87,[c] >3 w) | OG (89-90,[c] >1 m) | OG (syn, >90,[c] >1 y) | P | OG (syn, 83,[c] >1 y) |
| silicone oil | OG (73-74, >9 m) | OG (98-100, >1 y) | OG (90-91, >3 w) | OG (86-87, >1 m) | OG (83-85, >1 y) | OG (82-84, >1 m) | OG (83-84, >1 y) |
| methanol | soln | soln | P | soln | soln | soln | P |
| 1-butanol | soln | soln | soln | soln | soln | P | visc soln |
| 1-octanol | soln | OG (syn, 27-34, >1 y) | P | P | soln | P | visc soln |
| benzyl alcohol | soln | soln | soln | soln | soln | soln | visc soln |
| chlorobenzene | CG (46-48, >9 m) | CG (63-64, >1 y) | OG (56-57, >3 w) | OG (49-50, >1 m) | OG (52, >1 y) | OG (46, >1 m) | OG (55-57, >1 yr)[e] |
| chloroform | OG (21-22) | OG (syn, 38, 4 m) | P | soln | soln | soln | P |
| CCl$_4$- | CG (syn, 41, >9 m) | OG (syn, 63,[c] 4 m) | OG (syn, 68-69, >3 w) | OG (syn, 64-66, >1 m) | OG (syn, 58-60, 2 d) | OG (syn, 59-60, >1 m) | OG + visc soln |
| n-perfluorooctane | I | I | I | I | I | I | I |
| benzene | CG (49-50, 5 m) | CG (64-65, 7 m[d]) | OG (58-60, >3 w) | OG (57-61, >1 m) | OG (54-55, 2 m) | OG (47, >1 m) | P |
| toluene | CG (44-45, 9 m[d]) | CG (65-67, >1 y[e]) | OG (61-62, >3 w) | OG (57-58, >1 m) | OG (55-58, >1 y[e]) | OG (syn, 51, >1 m) | OG (syn, 58, 5 m) |
| DMSO | soln | soln | OG (45-47, >3 w) | OG (44-47, >1 m) | OG (52, >1 y) | OG (55-56, >1 m) | OG (syn, 74-75, 2 d) |
| acetonitrile | OG (45-48, 2 m) | OG (53-54, 2 m) | OG (59-60,[c] >3 w) | OG (56,[c] >1 m) | OG (62, 2 m) | OG (55,[c] >1 m) | P |
| water | I | I | I | I | I | I | I |

[a]OG—opaque gel, syn—syneresis, soln—solution, visc—viscous, P—precipitate, I—insoluble, CG—clear gel, y—year, m—month, d—day, w—week.
[b]The periods of stability were measured as the time between when gels were prepared in sealed containers at ~24° C. and when they underwent phase separation that could be detected visually; temporal stabilities of gels with $T_g$ below 24° C. were not measured.
[c]Phase separation: liquid fell upon heating; some or all solid did not.
[d]Syneresis after 2 months.
[e]Syneresis after 8 months.

TABLE 2

Appearances,[a] $T_g$ Values (° C.), and Periods of Stability[b] (in Parentheses) of Gels Containing 2 wt % Amine Derivatives of HSA (7-12) and the Ammonium Carbamate Salt of 7 (13) in Various Liquids

| liquid | 7 | 8 | 9 | 10 | 11 | 12 | 13 |
|---|---|---|---|---|---|---|---|
| n-hexane | P | P | P | OG (syn, 40-41, 2 d) | P | P | P |
| n-octane | P | P | P | OG (syn, 46, 1 w) | P | P | P |
| n-decane | P | P | P | OG (49, 1 m) | P | P | P |
| silicone oil | OG (21-22) | OG (57-58, >3 w) | OG (55-56, >1 m) | OG (62-63, >1 y) | OG (62-64, >1 m) | OG (67-69, >1 y) | OG (0-2) |
| methanol | soln | soln | soln | P | soln | P | P |
| 1-butanol | soln | soln | soln | soln | soln | visc soln | P |
| 1-octanol | soln | P | soln | soln | soln | visc soln | visc soln |
| benzyl alcohol | soln | soln | soln | soln | soln | soln + P | P |
| chlorobenzene | soln | soln | visc soln | visc soln | soln | P | OG (54-55, 5 m) |
| chloroform | CG (syn, 34-35, 4 m) | soln | soln | soln | soln | visc soln | OG (syn, 39-40, >1 y) |
| CCl$_4$- | visc soln | TG | OG (69-70,[c] >1 m) | OG (74-75,[c] >1 y) | TG (72-74, >1 m) | visc soln | soln |
| n-perfluoro-octane | I | I | I | I | I | I | I |
| benzene | soln | soln | soln | P | soln | P | P |

TABLE 2-continued

Appearances,[a] $T_g$ Values (° C.), and Periods of Stability[b] (in Parentheses) of Gels Containing 2 wt % Amine
Derivatives of HSA (7-12) and the Ammonium Carbamate Salt of 7 (13) in Various Liquids

| liquid | 7 | 8 | 9 | 10 | 11 | 12 | 13 |
|---|---|---|---|---|---|---|---|
| toluene | visc soln | soln | soln | OG (syn, 33-35, 1 h) | soln | P | soln |
| DMSO | visc soln | OG (36-42, >3 w) | OG (syn, 33-36, >1 m) | OG (59-60, 2 m) | OG (55-56, >2 m) | OG (63-83, >2 m) | soln |
| acetonitrile | P | P | P | P | P | P | P |
| water | I | I | I | I | I | I | I |

[a]OG—opaque gel, syn—syneresis, soln—solution, visc—viscous, P—precipitate, I—insoluble, TG—translucent gel, CG—clear gel, y—year, m—month, d—day, w—week.
[b]The periods of stability were measured as the time between when gels were prepared in sealed containers at ~24° C. and when they underwent phase separation that could be detected visually; temporal stabilities of gels with $T_g$ below 24° C. were not measured.
[c]Transformed to a CG at 35° C.[19]

For example, the Tg values for 2 wt % 14 gels are lower than those of 1 in silicone oil, benzene, and toluene but are higher in acetonitrile; in DMSO, 1 is dissolved whereas 14 forms a stable gel. This contrasting behavior, caused by the presence or absence of a 12-hydroxyl group along the long alkyl chain, can be traced to the relative solubilities of the two LMOGs: 14 is more soluble in less-polar liquids, and 1 is more soluble in more polar liquids.

The addition of an alkyl group to the amide group of 1 has two effects on its ability to gelate liquids: (1) the amides lose some of their potential to create H-bonding networks because one of the H atoms is replaced; (2) the amide group is moved from a molecular terminus to an interior position. The general trend in Table 1 toward lower Tg values in liquids such as silicone oil, $CCl_4$, chlorobenzene, benzene, and toluene as the amide functional group of the LMOG is moved farther from a terminus (i.e., Tg(1)>Tg(2)>Tg(3)) must be interpreted with caution; at constant amide wt %, the molar concentrations decrease as the length of the alkyl group increases and the number of possible H-bonding and London dispersive interactions decreases and increases, respectively. Possible changes in the molecular packing arrangements within a fiber (vide infra) add other complications. In addition, because the CGCs differ in each liquid, the total amount of an LMOG participating in the SAFIN of a gel will also differ, and the variation will not be constant from gelator to gelator.

FIG. 4 shows the Tg values versus alkyl chain length for the gels of 1-6 in different liquids. Except for DMSO gels, the Tg values for the primary amide (1) were higher than those of the secondary amides with N-methyl or N-ethyl groups (2 or 3), but further increases in the N-alkyl chain length do not appreciably alter the Tg values. DMSO gels of 1-6 behaved differently: Tg(6)>Tg(5)>Tg(4) and 2 wt % 1 remained soluble in DMSO at room temperature. Again, this trend appears to be related to the solubilities of the amides in DMSO, and there is a precedent for such behavior in other gel systems.[22]

H-bonding between amine groups is generally weaker than between amides, and as mentioned above, the differences between amino-amino and amido-amido aggregation modes may lead to changes in the overall packing arrangements of the gelator molecules in their fibers.[1] The importance of the stronger amide-amide interactions in the stabilization of the SAFINs is evident when the gels employing the amides (1-6) and the analogous amines (7-12) are compared. For example, the primary amine (7) is a much less efficient gelator than its primary amide analogue, 1; it gelates fewer of the investigated liquids, and its gels exhibit lower Tg values. Interestingly, 7 is also a much less efficient gelator than the secondary amine, 8, in which a methyl group replaces one of the H atoms on nitrogen (and thereby eliminates one potential H-bonding interaction). FIG. 5 presents a comparison of Tg values of the gels of 7-12 in DMSO and silicone oil. The trends in the silicone oil gels correlate with the melting temperatures of the neat gelators. This correlation and the very small temperature ranges for the gels indicate that the thermodynamic driving force for supersaturated solutions/sols in silicone oil is very large and that the gelator molecules are able to aggregate and nucleate rapidly below Tg. Whereas 2 wt % 7 is a viscous solution in DMSO at room temperature, 2 wt % 8 forms an opaque gel. The highest Tg value of the amine LMOGs investigated was found for the N-butyl derivative (11), and 2 wt % 12 in DMSO formed a precipitate when cooled from its sol phase.

1-Octadecylamine (15), the analogue of 7 lacking a 12-hydroxy group, is known to gelate silicone oil and DMSO at 5 wt %, and di-n-octadecyl amine (18), the corresponding analogue of secondary amine 12, forms gels with alkanes and alcohols (among other liquids), albeit with low Tg values. (Table 3) Thus, the removal of the hydroxyl group (and its H-bonding interactions) from 7 or 12 reduces the gelating abilities further.

TABLE 3

Appearances (AP)[a] and Tg values (° C.) of gels formed from compounds 14-17 (wt % in parenthesis) in various liquids.

| | 14(~2) | | 15[7,8](~2) | | 16[7](~3) | | 17[8](~2) | |
|---|---|---|---|---|---|---|---|---|
| Liquid | AP | Tg | AP | Tg | AP | Tg | AP | Tg |
| n-hexane | P | | | | | | P | |
| n-Octane | P | | | | | | P | |
| n-Decane | P | | | | | | | |
| Cyclohexane | | | P | | TG | 31 | | |
| Silicone Oil | OG | 72-74 | TG | 25 | | | TG | 59-60 |
| Methanol | OG | 30-34[b] | | | | | | |
| 1-Butanol | OG | 29-30 | P | | TG | 45 | P | |
| 1-Octanol | OG | 29-30 | P | | TG | 39 | P | |
| Benzyl alcohol | OG | 32-33 | S | | | | TG | 44 |
| Chlorobenzene | Visc Soln | | | | | | | |
| Chloroform | Visc Soln | | | | | | | |
| $CCl_4$ | OG | 28-30 | P | | | | P | |
| n-Perfluorooctane | I | | | | | | | |
| Benzene | OG | 34-35 | P | | TG | 30-33 | | |
| Toluene | CG | 34-36 | P | | TG | 34 | TG | 47-48 |
| DMSO | OG | 38-40 | TG | 50-52 | | | TG | 74-76 |
| Acetonitrile | OG | 59[b] | | | | | | |
| Water | I | | | | | | | |

[a]OG—opaque gel, TG—turbid gel, Visc Soln—viscous solution, P—precipitate, I—insoluble, CG—clear gel
[b]phase separation: liquid fell upon heating; some or all did not.

Ammonium carbamate (13), prepared by the addition of $CO_2$ to 1-aminooctadecan-12-ol (7),[6a] is a less-efficient LMOG than any of 1-12 or HSA. For example, the Tg values of silicone oil gels with 2 wt % gelator increase in the order 13 (0-2° C.)<7<HSA. To effect self-assembly, molecules of 13 must rely principally upon electrostatic interactions of the head groups and H-bonding among 12-hydroxyl groups; London dispersion forces among methylene units along the chains contribute as well. 1c, 1g. Thus, it is somewhat surprising, given the comparisons of the gelating abilities of 7 and 12 and their nonhydroxylated analogues (15 and 16), that 13 is a less efficient gelator than even the ammonium carbamate (17), which gelates silicone oil, benzyl alcohol, toluene, and DMSO (Table 3).[24] However, we note that the Tg of the gel from 2 wt % 13 in chlorobenzene is higher than that from even HSA, and 7 yielded no gel. Clearly, any correlation between LMOG structure and gelator efficiency must take into consideration some very complicated bulk and molecular aspects of interactions with the liquid components.

Example 4

Dependence of Gel Properties on LMOG Concentration

The data in FIG. 6 show that <1 wt % of each of the LMOGs included, except 7 and 13, is able to gelate silicone oil at room temperature. A clear gel was formed at room temperature even at 0.06 wt % 1, and the Tg values of these gels in the "plateau" concentration region (ca. 2-5 wt %, where the 3D SAFINs become more intricate but their basic structures and interactions are not changed appreciably[1,f]) are very high, near 100° C. At room temperature, the gels remained clear to concentrations 50.5 wt % and became increasingly opaque thereafter up to 5 wt %.

Silicone oil gels of the N-propyl amide (4) and N-octadecyl amide (6) are opaque throughout the concentration ranges explored. Although both are exceedingly effective gelators, their CGCs are slightly higher (0.2 and 0.4 wt %, respectively) than that of 1. The consequences of weaker H-bonding between amino groups of amine gelators 7, 10, and 12 are evident in both their CGC and Tg values; the CGC values are higher and the Tg values are lower than for the corresponding amides.

Table 4 summarizes the CGCs, appearances, and stability periods of silicone oil and toluene gels of 1, 4, 6, 7, 10, and 12 at room temperature.

TABLE 4

CGCs (wt %), Appearances (AP),[a] and Periods of Stability (PS)[b] for Silicone Oil and Toluene Gels with LMOGs 1, 4, 6, 7, 10 and 12 Prepared Using the Fast-Cooling Procedure

|  | silicone oil | | | toluene | | |
|---|---|---|---|---|---|---|
|  | CGC | AP | PS | CGC | AP | PS |
| 1 | 0.1 | CG | 4 d | 0.3 | CG | 2 m[c] |
| 4 | 0.2 | CG | 2 m[d] | 0.3 | CG | 2 m[c] |
| 6 | 0.4 | OG | 16 h[c] | 2.0 | OG | 5 m |
| 7 | 2.0[e] | OG |  | no gel | | |
| 10 | 0.2 | OG | 2 w | 2.0 | OG | 1 h |
| 12 | 0.5 | OG | 18 h | no gel | | |

[a]OG—opaque gel, CG—clear gel, syn—syneresis
[b]Periods at ~24 °C. in sealed containers between when gels were prepares and when visible phase separation was noted; m-month, d-day, w-week
[c]Syneresis after 1 h
[d]Syneresis after 2 weeks.
[e]Tg = 21-22 C.; temporal stabilities of gels with Tg below 24° C. were not measured.

These data consistently show that less LMOG is necessary to form a gel in silicone oil than in toluene because the LMOGs are more soluble in the latter, but there is no clear trend in the dependence of the liquid on periods of stability. The concentration dependence of 1 and 4 on the gelation properties in toluene has also been examined (FIG. 7): gels using 0.2-2.0 wt % 1 were clear, and 3-5 wt % gels were opaque in appearance; gels with 0.3-5.0 wt % 4 were transparent.

In some systems, including those in which N,N'-dialkyl ureas are the LMOGs,[15] the cooling protocol can lead to very different SAFINs with different Tg values.[23,25,26] That does not appear to be the case here. The gelation temperatures of the HSA derivatives in silicone oil were compared when their gels (at low and high LMOG concentrations) were prepared from their sols by fast- and slow-cooling protocols.

TABLE 5

Appearances and Tg values (° C., in parenthesis) of gels of HSA derivatives in silicone oil prepared by fast- and slow-cooling procedures.

| Gelator | Wt % | Fast-cooling | Wt % | Slow-cooling |
|---|---|---|---|---|
| 1 | 0.1 | CG (63-64) | 0.1 | CG (63-65) |
| 1 | 5 | OG (100-101) | 4.7 | OG (100) |
| 4 | 0.21 | OG (42-45) | 0.24 | OG (51-54) |
| 4 | 5 | OG (90-92) | 4.9 | OG (90-92) |
| 6 | 0.42 | OG (18-21) | 0.42 | OG (73-74) |
| 6 | 5 | OG (88 -90) | 4.9 | OG (89-90) |
| 10 | 0.21 | OG (20-26) | 0.19 | OG (30-32) |
| 10 | 5.0 | OG (67-68) | 5.1 | OG (67-68) |
| 12 | 0.5 | OG (35-37) | 0.5 | OG (35-38) |
| 12 | 4.2 | OG (72-73) | 4.8 | OG (74-76) |

[a]OG = opaque gel, CG = clear gel

The Tg values were not sensitive to the cooling protocol except for the gel with 0.42 wt % 6, where Tg=21-23 and 73-74° C. for gels made by the fast- and slow-cooling protocols, respectively. The reason for this large change appears to be related to a change in the morphology of its SAFIN (vide infra).

The mean temperature at which a SAFIN melts, Tm, and the heat associated with that transition have been measured by DSC for silicone oil gels at relatively high LMOG concentrations (in order to observe the endothermic and exothermic peaks easily in the thermograms). The normalized enthalpies (per gram of LMOG; see Table 6) as well as the entropies ($\Delta S = \Delta H / T_m$) of the reversible transitions were calculated using the averages of the absolute magnitudes of $\Delta H$ and the onset temperatures from the first heating and cooling thermograms of the silicone oil gels and neat solids. As expected, the Tm values of the SAFINs are always lower than the melting temperatures of the neat LMOGs; the silicone oil liquid aids SAFIN melting by dissolving the molecules in the fibers over a temperature range that precedes the loss of viscoelasticity.

TABLE 6

Comparison of $T_m$, $\Delta H^a$, and $\Delta S$ of Silicone Oil Gels and Neat Solids of 1, 4, 6, 8, and 12 during Their First Heating and Cooling, from DSC Thermograms, and $T_g$ Values from the Falling Drop Method

| gelator | conc | heating | | cooling | | | |
|---|---|---|---|---|---|---|---|
|  |  | $T_m$ (° C.) | $\Delta H$ (kJ mol$^{-1}$) | $T_m$ (° C.) | $-\Delta H$ (kJ mol$^{-1}$) | $T_g$ (° C.) | $\Delta S$ (J mol$^{-1}$K$^{-1}$) |
| 1 | 4.6 wt % | 100.1 | 51.8[b] | 104.6 | 48.5[b] | 100 | 134 |
|  | neat | 113.4 | 49.4 | 111.2 | 48.8 |  | 127 |
| 4 | 5.2 wt % | 94.3 | 49.5[c] | 90.0 | 47.5[c] | 90-92 | 133 |
|  | neat | 107.5 | 55.0 | 101.5 | 53.6 |  | 144 |
| 6 | 5.0 wt % | 91.7 | 86.1[d] | 91.7 | 71.2[d] | 89-90 | 216 |
|  | neat | 106.8 | 94.4 | 104.0 | 81.1 |  | 232 |
| 8 | 4.8 wt % | 59.1 | 50.7[e] | 60.7 | 43.9[e] | 67-68 | 142 |
|  | neat | 87.6 | 67.4 | 83.8 | 65.5 |  | 185 |

TABLE 6-continued

Comparison of $T_m$, $\Delta H^a$, and $\Delta S$ of Silicone Oil Gels and Neat Solids of 1, 4, 6, 8, and 12 during Their First Heating and Cooling, from DSC Thermograms, and $T_g$ Values from the Falling Drop Method

| gel-ator | cone | heating | | cooling | | | |
|---|---|---|---|---|---|---|---|
| | | $T_m$ (° C.) | $\Delta H$ (kJ mol$^{-1}$) | $T_m$ (° C.) | $-\Delta H$ (kJ mol$^{-1}$) | $T_g$ (° C.) | $\Delta S$ (J mol$^{-1}$K$^{-1}$) |
| 12 | 4.8 wt % | 73.1 | 83.4[c] | 70.9 | 70.5[e] | 74-76 | 223 |
| | neat | 93.1 | 95.8 | 87.8 | 95.8 | | 263 |

[a]$\Delta H$ values from the gels are normalized to 100% concentrations of the LMOG component by dividing the observed heats by the quantities listed in footnotes b-c.
[b]0.046.
[c]0.052.
[d]0.05.
[e]0.048.

Thus, the normalized heats of the gel transitions are generally lower than those of the associated neat LMOG. Only with the most efficient LMOG (1) do the normalized heats of the gels approach the heats found for the neat solid. In all other cases, the enthalpy and entropy values indicate that the dissolution of the LMOGs as their SAFINs melt is aided somewhat by silicone oil. In addition, the similarity between the Tm and Tg values in Table 6 indicates that the loss of the viscoelastic properties of these gels occurs as the bulk of the LMOG molecules melt, rather than at an earlier possible stage (e.g., when the junction zones between the fibers of SAFIN are severed).[1a,13]

SAFIN Structural Information from Polarizing Optical Microscopy and Scanning Electron Microscopy:

As has been found in many other systems, the spherulites of gels from the HSA derivatives are larger when prepared by the slow-cooling protocol; see, for example, the POMs in FIG. 8. Generally, more supersaturation results in smaller and more numerous crystals,[27] and the driving force for the phase separation of a sol, leading to nucleation, fiber growth, and SAFIN formation, increases with increasing supersaturation (i.e., as the reduced gelation temperature, Tg-T, for sol incubation increases)[2] whereas the sizes of the basic SAFIN units (fibers or spherulites) decrease and become more numerous or the morphology of the LMOG objects changes.[25,29]

The spherulitic objects of slow-cooled gels of 2 wt % 4 in n-decane, CCl4, DMSO, or silicone oil are larger than from the fast-cooled ones (FIGS. 9-13). The fast-cooled gels of 4 in toluene and the 2 wt % gels of 6, 10, and 12 show spherulitic textures similar to those of 1 in FIG. 8c (FIGS. 14-23). The much higher Tg of the slow-cooled rather than fast-cooled gel of 0.42 wt % 6 in silicone oil is consistent with its larger spherulites (FIG. 24). However, the magnitude of the Tg difference for this gel, ca. 50° C., is difficult to rationalize on the basis of the sizes of the SAFIN objects alone. XRD data presented later indicate that the molecular packing within the objects of a fast-cooled gel with 5.0 wt % 6 in silicone oil differs from that of neat 6. Unfortunately, the XRD method is not sufficiently sensitive to produce useful information on slow- and fast-cooled gels at 0.42 wt %. Also, for reasons that remain unclear, the gels of 1 in toluene prepared by the fast-cooling protocol exhibit a spherulitic texture (FIG. 8c) whereas the SAFIN substructure in the slow-cooled gel is too small (≤2 um) to be seen by our optical microscope (FIG. 8d).

SEM images of xerogels prepared from representative gels were recorded (FIG. 25). The micrographs from opaque gels of 2.0 and 0.5 wt % 1 in CCl$_4$ show fibrous structures, and that from 0.5 wt % 1 indicates that the fibers are helical (FIG. 25b). Micrographs from transparent gels of 2.0 and 0.5 wt % 1 in chlorobenzene also show fibrous structures, including evidence of twisting in the more dilute sample (FIG. 25 c,d).

Molecular Packing within SAFIN Objects from X-Ray Diffraction Data:

XRD diffractograms of neat powders and fast-cooled silicone oil gels with 5 wt % 1, 4, 6, 7, 10, 12, and 13 have been compared. The diffraction peaks of the gels were identified by subtracting the amorphous scattering of the silicone oil from the total gel diffractogram.[30] The same morphology is present in the SAFINs of the gels and in the neat powders if the peaks in their diffractograms are found at the same values of 2θ, as is the case for 1 (FIG. 26 a,b). However, the correspondence is less clear for 4 and 6 (FIGS. 26 c-f). The lattice spacings (d, Å) of the HSA derivatives in their crystalline and silicone oil gels have been calculated from the Bragg relationship and are summarized in Table 7. In all cases, attempts to index the diffraction peaks in Table 6 for 1, 4, 6, 7, 10, 12, and 13[31] and thereby to identify the gross natures of their cell packing were unsuccessful.

TABLE 7

Comparison of Lattice Spacings (d, A) of 1, 4, 6, 7, 10, 12 and 13 in the Neat Powders and Gels[a] (from XRD data at 24° C.) and Calculated Extended Molecular Lengths (L, Å)

| | L[32] | d (powder state) | d (gel state) |
|---|---|---|---|
| 1 | 26.4 | 48.5, 15.7, 4.5, 3.9, 3.8 | 48.5, 15.7, 4.5, 3.9, 3.8 |
| 4 | 31.1 | 28.5, 14.3, 10.8, 8.2, 4.7, 4.1, 3.9, 3.6 | 28.5, 14.3, 4.2, 4.0, 3.8 |
| 6 | 50.3 | 23.8, 16.0, 12.2, 9.5, 8.8, 4.6, 4.1, 3.9, 3.5 | 46.5, 23.0, 14.0, 4.4, 3.9, 3.8, 3.7 |
| 7 | 27.2 | 47.1, 22.6, 17.2, 7.6, 7.3, 4.5, 4.2, 3.4, 3.1 | 17.4, 4.5, 4.1, 3.9 |
| 10 | 31.0 | 26.7, 13.6, 8.2, 6.5, 5.8, 5.0, 4.3, 4.1, 3.9, 3.6, 2.5, 2.4, 2.3 | 26.7, 13.6, 4.3, 4.1, 3.9, 3.6, 2.5, 2.3 |
| 12 | 50.2 | 16.0, 8.3, 7.5, 4.1, 3.7 | 47.7, 14.1, 4.1, 3.8 |
| 13 | 49.9 | 49.0, 16.9, 4.5, 4.1 | 49.0, 16.9, 4.5, 4.1 |

[a]Gels prepare in silicone oil (~5 wt %) using the fast-cooling protocol.

The Bragg distances of the low-angle peaks, indicative of lamellar packing, represent the thicknesses of the layers. For 1, they are slightly less than twice the calculated extended molecular length[3] (Table 6), suggesting a packing arrangement like that in FIG. 27a. The positions of the diffraction peaks of the silicone oil gel of 4 correspond to that of the neat powder, but the relative intensities within the two diffractograms differ as would be expected if the fibers of the SAFINs of 4 are oriented with respect to the capillary walls.[24] (FIG. 26c and Table 7). Consistent with a monolayer arrangement like that shown in FIG. 27b, the distances corresponding to the lowest-angle peaks in the diffractograms are approximately the same as the calculated extended length of one molecule of 4. Diffraction peaks of the silicone oil gel of the corresponding N-propyl amine, 10 (FIG. 28), correlate with those of the neat powder as well.

Additional evidence for the same morphology of the LMOGs being present in the SAFINs and neat solid phases has been obtained from IR studies. The NH, OH, and CO stretching band frequencies of silicone oil gels with 5 wt % amide (1 or 4) are almost the same as those of the neat gelator (FIG. 29). The NH stretching frequencies of the neat powder of amine 10 and its 5 wt % gel in silicone oil are also virtually the same. In addition, the sharpness of these IR peaks is consistent with specific H-bonding networks in the SAFIN fibers.

However, different diffraction peaks are found for the silicone oil gel and neat powder of both of the N-octadecyl LMOGs, 6 (FIG. 26 e,f) and 12 (FIG. 30). For both gels, the lowest-angle peak in the XRD pattern corresponds approximately to the calculated extended length of one molecule and is consistent with a monolayer packing arrangement in the SAFINs (FIG. 27c). The lowest-angle peaks observed correspond to distances that are less than one-half of the calculated molecular lengths. Thus, the data in hand are not consistent with a lamellar packing arrangement that is like any of the models in FIG. 27. However, the diffractograms of the powders of 6 and 12 may be missing key peaks at angles lower than our diffractometer can record.

The diffraction pattern of the aggregates of 7 in its silicone oil gel (FIG. 31) does not coincide with that of the neat powder. In the gel state, the low-angle peaks were very small even after exposure of the sample to X-rays for a period much longer than required to obtain good signal-to-noise ratios after solvent subtraction in the other gels at the same LMOG concentration. The layer spacing calculated from the analysis of the neat powder of 7 is slightly less than twice the calculated extended molecular length, suggesting a bilayer packing arrangement. Finally, the X-ray diffractograms of the neat solid and silicone oil gel of the ammonium carbamate (13) indicate the same packing arrangement, probably stacked layers in which one ammonium and one carbamate are end-on (Table 6 and FIG. 32).

Rheological Properties:

The upper limit of the linear viscoelastic regime of a gel consisting of 2 wt % 1 in silicone oil was strain amplitude $\gamma \approx 0.1\%$ at angular frequency $\omega=1$ rad s$^{-1}$ at both 25 and 80° C. (FIG. 33). Within this regime, the storage modulus (d) is 1 order of magnitude larger than the loss modulus (G")—the gel is very stiff—and the G' and G" values are independent of the applied frequency over a range of at least $\omega=0.01$-$1.0$ rad s$^{-1}$ from 25 to 80° C. (FIG. 34). G" and G' indicate that the gel becomes weaker with increasing temperature, perhaps as a result of more 1 being dissolved (FIG. 6).

Strain sweep tests from $\gamma=0.01$ to $100\%$ at $\omega=1$ rad s-1 were also performed for a 2 wt % 4 in silicone oil gel at 25° C. The G' and G" values remained approximately independent of applied strain up to 0.1%. Surprisingly, as the applied strain was increased at 45 or 75° C., both G' and G" increased initially (FIGS. 35 and 36). These observations are attributed to slow phase separation because the sample was visually a mixture of solid and liquid after the experiment. A similar frequency sweep experiment on a 2 wt % 4 in silicone oil gel showed that G' and G" are independent of the applied frequency at 25 and 35° C. but phase separation occurs at higher temperatures (FIG. 37).

The G' and G" values of a 2 wt % 10 in silicone oil gel decreased initially upon increasing strain at 25 and 50° C. ($\omega=1.0$ rad s$^{-1}$; FIG. 38); the 10/silicone oil gels are mechanically less stable than the corresponding 1 and 4 gels. At $\gamma=0.05\%$ strain, G' and G" of the 2 wt % 10 in silicone oil gel were independent of the applied frequency at different temperatures (FIG. 39), thus confirming the viscoelasticity of the gel.

Thixotropic Properties:

Usually, organogels from LMOGs, especially those in which the SAFINs are crystalline (as is the case here), are mechanically weak and are easily destroyed when subjected to external mechanical strain. Moreover, they are only weakly thixotropic, and after the cessation of severe mechanical strain, they can be reconstructed only by heating the mixture to its sol/solution state and cooling to below Tg. Several recent reports have attempted to explain the thixotropic behavior of LMOG-based organogels with crystalline SAFINs.[33] In all of these cases,[33a] the restoration of the gel viscoelasticity, indicating at least some reestablishment of the SAFIN after mechanical disruption, required minutes to hours. Surprisingly, the recovery times of the gels in this work are much faster than previously reported in similar materials.

The linear viscoelastic moduli, G' and G", was measured for a 2 wt 1 in silicone oil gel at 25° C. by performing oscillatory rheological measurements in a parallel plate geometry. At a strain amplitude of $\gamma=0.1\%$ and angular frequency of $\omega=100$ rad s$^{-1}$, the gel is in the linear regime. Under these conditions, we measured the gel response for 150 s and saw no evolution of the moduli. Then, $\gamma$ was increased to 30% while keeping co fixed, resulting in a loss of elasticity (FIG. 33). These conditions were applied for 30 s. FIG. 40 shows the evolution of G' and G" after $\gamma$ is returned to the original conditions while maintaining $\gamma=100$ rad s$^{-1}$. The kinetics of recovery were too rapid to be measured by the rheometer; ca. 90% of the original G' value (28 000—25 000 Pa) and ca. 96% of the original G" value (8500—8100 Pa) were recovered in less than 10 s. The rises in G' and G" observed from 180 to 190 s are attributed to an instrumental artifact caused by the inertia of changing from higher strain (30%) to lower strain (0.1%). Experiments with similar strain profiles, $\gamma=(50, 70, 90,$ and $120)$ % and $\omega=1$ rad s$^{-1}$ held for 30 s, demonstrate very similar results—the recovery of ca. 88% of the initial G' value in less than 10 s. Although the actual times and events responsible for this recovery may be partially due to instrumental factors and tool slip (i.e., a loss of contact between the sample and the metal plates of the rheometer), the rapid recovery does not appear to be an artifact of the measurement. To demonstrate this, a bulk sample of this gel was severely disturbed mechanically by moving a glass rod through it rapidly for more than 1 min. On all observable time scales, the material remained a gel without any qualitatively discernible change in its appearance or viscoelasticity.

Similar rheological measurements on silicone oil gels containing 2.0 wt % HSA, 2, 4, 10, and 12 resulted in equally fast but somewhat lower recoveries of the original G' values (Table 8 and FIGS. 41-45). The degrees of recovery correlate at least qualitatively with the potential strength of hydrogen-bonding interactions among the LMOGs: 1° amide (1)>acid (HSA)>2° amides (2, 4)>2° amines (10, 12). In FIGS. 41 and 42, the rises in G' and G" observed from 180 to 190 s are attributed to an instrumental artifact caused by the inertia of changing from higher strain (30%) to lower strain (0.1%). In FIG. 43, the rise and decay in G' and rise in G" observed from 600 to 610 s are attributed to an instrumental artifact caused by the inertia of changing from higher strain (100%) to lower strain (0.05%). In FIG. 44, The rise and decay in G' and rise in G" observed from 180 to 190 s are attributed to an instrumental artifact caused by the inertia of changing from higher strain (100%) to lower strain (0.05%). In FIG. 45, the rise and decay in G' and rise in G" observed from 180 to 190 s are attributed to an instrumental artifact caused by the inertia of changing from higher strain (100%) to a lower strain (0.05%).

TABLE 8

Comparison of the Degree of Thixotropy of HAS and Several of Its Derivatives at 2 wt % in Silicone Oil Gels at 25° C.:

| | G' recovery[a,b] |
|---|---|
| HSA | 69.8 ± 3.2 |
| 1 | 90.0 ± 1.0 |
| 2 | 45.0 ± 9.0 |

TABLE 8-continued

Comparison of the Degree of Thixotropy of HAS and Several of Its Derivatives at 2 wt % in Silicone Oil Gels at 25° C.:

| | G' recovery$^{a,b}$ |
|---|---|
| 4 | 42.5 ± 14.2 |
| 10 | 3.8 ± 0.3 |
| 12 | 9.2 ± 4.6 |

$^a$Calculated from the ratio of the G' values after and before applying destructive strain (30% strain amplitude and 1 rad s$^{-1}$ for HAS, 1, 12 and 100% strain amplitude and 1 rad s$^{-1}$ for 4 and 10) for 30 s at 25° C.
$^b$Average of three separate experiments.

As mentioned, a possible mechanism for the remarkably fast recovery times and, in several cases, high degrees of recovery of the viscoelastic properties includes slip or broken contacts between the SAFINs of the gels and the metal plates of the rheometer. To test this, we measured the recovery of G' for a gel that is only moderately thixotropic, 2 wt % 2 in silicone oil, at different plate separations. At all separations investigated (Table 9), the recovery was within the instrumental response time of the rheometer, <10 s. We hypothesize that if slip or surface destruction of the gel were responsible for the rapid recovery, G' should decrease as the gap is increased. However, contrary to our expectations, G' increased as the plate gap decreased. Finally, an experiment with the same gel of 2 in silicone oil was performed using cone-plate geometry in which the strain is constant along the radius of the tool; there is a strain gradient along a radius in the plate-plate geometry. The results from the cone-plate geometry experiment are consistent with those from the 0.1 mm plate-plate gap experiment-ca. 85% recovery of G' in less than 10 s (Table 9).

TABLE 9

Comparison of the Thixotropic Properties of 2 wt % 2 in Silicone Oil Gels at 25° C. at Different Parallel Plate Separations and Cone-Plate Geometry.

| geometry | gap (mm) | % G' recovery$^{a,b}$ |
|---|---|---|
| parallel plate | 1.0 | 19.6 ± 1.6 |
| parallel plate | 0.5 | 45.0 ± 9.0 |
| parallel plate | 0.25 | 68.3 ± 0.9 |
| parallel plate | 0.1 | 83.0 ± 2.1 |
| cone-plate | 0.05$^c$ | 86.7 ± 2.3 |

$^a$Calculated from the ratio of the G' values after and before applying destructive strain (30% strain amplitude and 1 rad s$^{-1}$ angular frequency) for 30 s.
$^b$Average from two separate experiments.
$^c$Closest contact of cone to plate.

Although the results in Table 8 point to the importance of hydrogen-bonding interactions, the mechanism of the recovery of these SAFINs remains unknown. In the sole literature precedent for such behavior in organogels with crystalline SAFINs that we have been able to find,[33a] N-(3-hydroxypropyl) dodecanamide in toluene was transformed by applied strain from a jammed phase (a gel) to an aligned phase (a sol in which the fibers are no longer in an effective 3D network). The rate of recovery of viscoelasticity after cessation of the destructive strain was dependent on the prior history of the sample, but the fastest recovery required a few minutes. The explanation given for these results may be applicable, at least in part, to our systems as well: the fibers of the SAFIN in the gel are joined by H-bonding interactions along their surfaces; the applied strain can break these interactions without destroying the fibers or a large part of their meso structures (N. B., spherulites in our SAFINs); and cessation of the destructive strain allows the aligned fibers (and spherulites) to diffuse rotationally and translationally to reform the SAFIN via renewed contacts. The fibrillar structures detected by optical and electron microscopy for the LMOGs in our study are compatible with such a mechanism, but they do not demand it.

The introduction of a hydroxyl group along the alkyl chain of stearic acid (a b-type molecule in Scheme 1), as in HSA (a c-type molecule), changes the gelating ability of an LMOG enormously. The efficiency of the HSA-derived gelators, has been tuned further by modifying the carboxylic acid functionality of the head group, making it 1 of 13 different nitrogen containing moieties. The efficiencies are improved when the carboxylic acid functionality is transformed into a primary amide (1, a c-type molecule), but efficiency suffers when a primary amine is placed in its stead (7, a different c-type molecule). Further changes of 1 to a secondary amide (2 or 3; molecules intermediate between c- and d-types) lead to decreased overall efficiencies, and increasing the alkyl chain length of the N-alkyl group of the secondary amide (i.e., from methyl in 2 to N-octadecyl in 6, a d-type molecule) decreased the range of the liquids gelated further. Removal of the hydroxyl group in 1 yields stearamide (14, a b-type molecule), a very good LMOG that gelates a somewhat different set of liquids than 1 or HSA. The major differences in the gelated liquids can be understood on the basis of solubility considerations.

The importance of the ability of the head groups to act as both H-bonding donors and acceptors is demonstrated by the higher efficiency of the amides (1-6) than that of their corresponding amines (7-12) and ammonium carbamate 13. Furthermore, the link between the ability to establish a strong H-bonding network along the octadecyl chains[12a] and a robust SAFIN is indicated by comparisons of the gelator efficiencies of the HSA and corresponding SA derivatives. The IR spectral data are consistent with this interpretation because the NH, OH, and CO stretching bands are sharp (FIG. 29), indicative of specific modes of H-bonding. However, our observation that the ammonium carbamate with pendant hydroxy groups (13) is an inferior gelator to the one without hydroxy groups (17) suggests that the pendant group interactions are not always beneficial to gelation. Two possible reasons in the present case are (1) the secondary H-bonding network from the hydroxyl groups is established and imposes restraints on molecular packing that are not conducive to fiber (and SAFIN) formation and (2) the hydroxyl groups interact with the charged centers and lead to nonfibrous packing motifs.[18]

The primary headgroup interactions in the ammonium carbamate 13 are electrostatic in nature and, for that reason, potentially stronger than H-bonding in several of the low polarity liquids gelated. However, 13 is a much less efficient gelator than the amides or amines. We suspect that the density of charges in the proximity of the head-group regions within the SAFIN fibers attenuates cationic-anionic charge stabilization. In other systems where the organization of charged head groups and their counterions within planes are known and the planes are separated by layers of long alkyl chains (as they appear to be here), the degree of stabilization is dependent on how well the opposite charges are able to adopt an alternating pattern.[34] Although we lack the structural information within the fibers of 13 to make a substantive model, we conjecture that such a pattern is not achieved in the fibers of 13, perhaps as a consequence of packing constraints imposed by H-bonding networks of hydroxyl groups along the octadecyl chains.

As indicated by optical microscopy, differential scanning calorimetry, and X-ray diffractometry, the packing within the gel fibers of 1-13 is crystalline. Comparisons between X-ray diffractograms of the SAFINs of silicone oil gels and the neat powders of the LMOGs demonstrate that the same morphology is obtained in all cases except for 6 and 12. Unfortunately, our efforts to grow diffraction-quality single crystals have not been successful thus far, and the exact nature of the packing within fibers is not known.[28] However, the low-angle diffraction peaks indicate that almost all of the LMOGs studied here pack in layers within their gel fibers.

Another interesting observation is that some of these organogels recover their viscoelasticity very rapidly after being destroyed by shear. For example, gels of 2 wt % 1 in silicone oil recovered ca. 90% of their original viscoelasticity within 10 s after the cessation of destructive shear, and several other gels recovered less viscoelasticity but equally fast. The fastest reversibility of which we are aware in other thixotropic organogels with crystalline SAFINs requires at least minutes.

Taken in total, our results suggest that the stabilization afforded by H-bonding in amide networks is the most important factor in determining stabilities within their SAFINs. By limiting the H-bonding networks within a fiber to one donor per molecule, the N-alkyl groups of the secondary amides and amines also affect the shapes of the SAFIN fibers. In addition, the comparisons of gelator efficiency and stability when no, one, and two potentially strong anchoring points are placed along an alkane chain demonstrate that more is not always better! The stabilization gained when two or even several molecules aggregate can be lost when they are forced to pack efficiently in a crystalline matrix. The design of efficient gelators must take into consideration extended matrix effects, as has been done in a few examples thus far.[1b,1d]

As a result of these attributes and the fact that organogels were formed at exceedingly low LMOG concentrations in a variety of liquids, these amides (and perhaps amines) maybe useful as substitutes for HSA in its industrial applications,[35] or they may open the possibility of new applications. Perhaps most importantly is that the comparisons made among HSA and its derivatives 1-13 with SA and its derivatives 14-16, both pairwise and in series, provide a comprehensive picture of the factors leading to the stability of these organogels. However, several unanticipated and challenging questions have arisen from the work presented here: there are general trends that can be extracted from correlations between the structure types in Scheme 1 and the properties of the gels formed, but a priori predictions of which LMOG will gel which liquid and what the properties of the gel will be remain elusive goals. That is the case even within the well-controlled series of simple LMOG structures examined here.

Efficient ambidextrous gelators of water and organic solvents based on n-alkyl-n-(R)-12-hydroxyoctadecyl-ammonium salts were prepared from (R)-12-hydroxystearic acid, a renewable feedstock obtained from castor oil. The structures of the compounds (18-32) are shown in FIG. 48.

Organo/hydro gels are thermo reversible viscoelastic materials consisting of low molecular weight gelators self assembled into complex three-dimensional structures. Different forms of molecular gels are common in everyday life for their applications ranging from personal care products (toothpaste, shampoo), foodstuffs (jellies, puddings), electronic devices, and drug delivery vehicles (gel capsules for vitamin E). Only few gelators have capability to exhibit gelation property in water and organic solvents. Less than 1 wt % of the salts described above are able to gel water and a wide variety of organic liquids with equal efficiency. (FIG. 50).

Gelation properties of the salts 18-25 in different liquids are given in Table 10. Many of the gelators form hydrogels as well as organogels, ie., they are 'ambidextrous'. Tgel values of the 2 wt % hydrogels increase in the order of increasing their N-alkyl chain length (that is 20<21<22<23, FIG. 49). This trend appears to be related to the solubility of gelator molecules in water. Further increasing of N-alkyl chain from N-pentyl to N-hexyl increase in the hydrophobic interactions that consequence in the formation of precipitate. For the similar reason the compound having N-octadecyl chain (8) did not gelate water. All the gelators (19 to 24) except 18 gelate $CCl_4$ and toluene forming translucent and transparent gels respectively. A 2 wt % of 18 form a viscous solution in $CCl_4$ and clear solution was observed in toluene. In $CCl_4$ and toluene Tgel value does not significantly vary for the gelators 19-22. Slightly low Tgel value was observed for the gelators 6 and 8 in $CCl_4$ and toluene compare to the gelators 19-22 under similar condition, which may be because of difference in solubility of the gelators (FIG. 49).

FIG. 3 (I) show concentration versus gel melting temperatures of 4 in toluene and water gels. Concentration dependent studies of 8 in toluene gels were also studied (FIG. 50 (II).

TABLE 10

Appearances,[a] Tgel values (° C.)[b], and periods of stability[c] (in parentheses) of fast-cooled gels containing ~2 wt % of gelator in various liquids.

| Solvent | 18 | 19 | 20 | 21 | 22 | 23 | 24 | 25 |
|---|---|---|---|---|---|---|---|---|
| Water | Visc Soln | Visc Soln | OG (57, >8 m) | OG (76-77, >8 m) | OG (83, >3 m) | OG (94, >2m) | P | P |
| Methanol | Soln | Soln | Soln | Soln | Soln | Soln | Soln | OG (32-34, >8 m) |
| 1-Butanol | Soln | Soln | Soln | Soln | Soln | Soln | Soln | TG (34-35, 1 m) |
| 1-Octanol | Visc Soln | P | P | P | P | TG (29-32, >2 m) | TG (28-29) | TG (40-43, >8 m) |
| Benzyl alcohol | Soln | Soln | Soln | Soln | Soln | Soln | Soln | CG (33-35, 1 m) |
| Acetonitrile | P | P | OG (73-74, >6 m) | OG (76[d], >6 m) | OG (67, >3 m) | OG (78-79, >2 m) | OG (71-72) | P |
| $CCl_4$ | Visc Soln | TG (76, >6 m[f]) | TG (76-77, >6 m[f]) | TG(76-77, >6 m[f]) | TG (73, >3 m) | TG (72, >2 m) | TG (69) | TG[e] (55, >6 m) |
| Toluene | Soln | CG (syn, 74-75 >8 m) | CG (77-78, >8 m) | CG (77-78, >8 m) | CG (74, >3 m) | CG (72-73, >2 m) | CG (68-69) | CG (60, >8 m) |
| n-Hexane | I | I | I | I | I | I | I | OG (83, >2 w) |

TABLE 10-continued

Appearances,[a] Tgel values (° C.)[b], and periods of stability[c] (in parentheses) of fast-cooled gels containing ~2 wt % of gelator in various liquids.

| Solvent | 18 | 19 | 20 | 21 | 22 | 23 | 24 | 25 |
|---|---|---|---|---|---|---|---|---|
| n-Dodecane | P | P | P | I | I | I | P | Visc Soln |
| Cyclohexane | I | P | P | P | P | P | P | OG (70-71, >2 w) |

[a]OG—opaque gel, Syn—syneresis, Soln—solution, Visc—viscous, P—precipitate, TG—translucent gel, CG—clear gel, m—month.
[b]Tgel—gel melting temperature obtained from falling drop method and the temperature ranges indicate when the initial and final portions of an inverted gel sample fell on being heated slowly.
[c]The periods of stability are being measured as the time between when gels were prepared in sealed containers at ~24° C. and when they underwent phase separation that could be detected visually.
[d]phase separation was observed.
[e]Gel was formed after keeping the sol for ~1 w at 22° C.
[f]syneresis after 5 months To study the effect of different counter ions on the gelation properties ammonium salts 9-15 were prepared. Table 10 show gelation properties of 9-15 in various liquids.

gel diffractogram. XRD reflection pattern of the hydrogel of 21 is identical with that of the neat 21 (FIG. 52A, b and FIG. 52A, c) which show that same packing is present in the

TABLE 11

Appearances,[a] Tgel values (° C.)[b], and periods of stability[c] (in parentheses) of fast-cooled gels containing ~2 wt % of gelator in various liquids.

| Solvent | 26, X = Br | 17, X = I | 28, X = NO$_3$ | 29, X = BF$_4$ | 30, X = Acetate | 31, X = Octanoate | 32, X = Oxalate |
|---|---|---|---|---|---|---|---|
| Water | OG (83-84, >1 m) | P | OG (80-81, >1 m) | OG (81, >1 m)[d] | Visc Soln | P | OG (98-99[e], >1 m) |
| Methanol | Soln | Soln | Soln | Soln | Soln | Soln | P |
| 1-Butanol | P | Soln | Soln | P | Soln | Soln | P |
| 1-Octanol | P | P | Soln | P | P | Soln | Visc Soln |
| Benzyl alcohol | Soln | Soln | Soln | Soln | Soln | Soln | Soln |
| Acetonitrile | OG (61-62, >1 m) | P | P | Soln | P | P | I |
| CCl$_4$ | TG (74, >1 m) | Soln | TG (59, >1 m) | Soln | CG (76[e], >1 m) | CG (74-76[e], >1 m) | Soln |
| Toluene | CG (69, >1 m) | Soln | Soln | Soln | Soln | Soln | P |
| Cyclohexane | P | I | P | P | P | P | I |
| n-Dodecane | I | I | P | I | P | P | I |
| n-Hexane | I | I | I | P | P | P | I |

[a]OG—opaque gel, Soln—solution, Visc—viscous, P—precipitate, TG—translucent gel, CG—clear gel, I—insoluble, m—month.
[b]Tgel—gel melting temperature obtained from falling drop method and the temperature ranges indicate when the initial and final portions of an inverted gel sample fell on being heated slowly.
[c]The periods of stability are being measured as the time between when gels were prepared in sealed containers at ~24° C. and when they underwent phase separation that could be detected visually.
[d]5 wt %,
[e]phase separation was observed.

POM images of a 5 wt % fast- and slow-cooled transparent gel of 21 in toluene gel show a spherulitic texture (FIGS. 51A and 4B). This reveals that the network structure present in the gel is crystalline in nature. More super saturation increased the effect in nucleation of crystal growth and produce larger fibers. The size of the objects is apparent comparing the POM image of a gel prepared by a slow-cooled protocol (FIG. 51B) with the gel prepared by fast-cooled protocol (FIG. 51A). Larger spherulitic image is observed in the latter case. An opaque hydrogel obtained from 5 wt % 21 also exhibit spherulites and smaller and larger and spherulitic images were observed for the samples prepared using a fast- and slow-cooled protocol (FIG. 51C and FIG. 51D). FIG. 51E show POM image of a translucent gel of 1.9 wt % of 25 in octanol. A spherulitic image was seen for the slow cooled sample of 1.9 wt % of 25 in octanol.

XRD diffractograms of neat powders and fast-cooled hydrogels with ~5 wt % 21 have been compared. The diffraction peaks of the networks of the gels were identified by subtracting the scattering pattern of the water from the total hydrogel networks and in neat solid gelator. The lattice spacings (d, Å) of the hydrogel of 21 and 21 in powder state have been calculated from the Bragg relationship and are summarized in Table 12.

TABLE 12

Lattice spacings (d, Å) of 20, 21 and 25 in their neat powders and ~5 wt % gels[a] (from XRD data at 22° C.) and calculated extended molecular lengths (L, Å)$^5$:

| Compound | solvent | L | d |
|---|---|---|---|
| 20 | neat solid | 29.3 | 31.5, 13.1, 9.0, 6.9, 5.0, 4.3, 4.0, 3.5 |
| 20 | water | 29.3 | 31.5, 13.1, 6.9, 5.0, 4.3, 4.0 |
| 21 | neat solid | 30.5 | 31.6, 13.5, 9.4, 7.2, 4.9, 4.0, 3.5 |
| 21 | water | 30.5 | 31.6, 13.5, 9.4, 7.2, 4.9, 4.0, 3.5 |
| 21 | toluene | 30.5 | 55.2, 27.5, 13.8, 5.1, 4.5, 3.5 |
| 25 | neat solid | 49.9 | 42.8, 21.4, 14.2, 4.9, 4.4, 3.9, 3.5 |
| 25 | octanol | 49.9 | 49.3, 4.5, 3.9 |

[a]Gels prepared using the fast-cooling protocol.

The distances corresponding to the lowest angle peaks in the diffractograms are approximately the same as the calculated extended length of one molecule for the hydrogel of 21 and neat gelator (Table 12), suggesting a monolayer packing arrangement like that in FIG. 6a. It should be noted here that FIG. 53a is a primary aggregate structure and to stabilize the network structure of 21 in hydrogel hydrophilic ammonium moiety of 21 should face to the solvent, and form interdigitated bilayer structure. This kind of bilayer arrangement structures were reported for amphiphilic molecules in water. X-ray diffraction diagram of a 5.0 wt % gel of 21 in toluene is remarkably different from that obtained in water, with a sharp peak appearing at 55.2 Å in the small-angle region (FIG. 52A, a). Other obtained long spacings (d) of the 21 in toluene gels are 27.5 Å and 13.8 Å, corresponding to the ratio of 1:1/2:1/4. 55.2 Å is smaller than twice that of the extended molecular length of 21, but larger than the length of one molecule. The toluene gel thus, should maintain an inverse bilayer structure with a thickness of 55.2 Å. This value is compatible with an inverse bilayer structure as shown in FIG. 53B. The compound 8 did not form hydrogel because of the increase in hydrophobic character due to octadecyl chain. The fast cooled opaque gel of 25 in octanol exhibit a small angled peak at 49.3 Å (FIG. 53B, c). This d-spacing value matches with the calculated molecular length (49.9 Å) suggesting a packing arrangement like that in FIG. 6c. Other sharp reflection peaks observed at wide angle region (4.5 Å and 3.9 Å, FIG. 52B, c) for the 25-octanol gel support the view that long alkyl chain groups' form highly ordered layer packing as shown in FIG. 6C. The position of the long spacings (d) of the neat powder of 25 are at 42.8 Å, 21.4 Å and 14.2 (FIG. 53B, a), corresponding to the ratio of ratio of 1:1/2:1/3.

The upper limit of the linear viscoelastic regime of a gel consisting of 2.1 wt % 21 in hydrogel was ca. 0.5% strain at 1 rad/s (at 25° C.) and under similar conditions yield strain obtained for the toluene gel was 0.2% (FIG. 54A). This shows that hydrogel of 21 is mechanically stronger compare to its toluene gel. At higher strain % these gels were phase separated. Storage modulus (G') and loss modulus (G") values are independent of the applied frequency over a range of at least 0.01-100 rad/s at 25° C. at 0.1% strain (FIG. 54B) confirming its viscoelastic behavior. Table 13 summarizes comparison of the rheological properties of the hydrogel and toluene gel of 21.

TABLE 13

Comparison of rhelogical properties (storage modulus, loss modulus, yield strain and tanδ) of 2.1 wt % of hydrogel and toluene gel of 21 at 1 rad/s frequency:

| Solvent | G', Pa | G', Pa | Yield strain, % | tan δ |
|---|---|---|---|---|
| Water | $3.2 \times 10^5$ | $7.0 \times 10^4$ | 0.5 | 0.03 |
| Toluene | $9.3 \times 10^4$ | $1.6 \times 10^4$ | 0.2 | 0.17 |

Example 5

Phase Selective Gelation of Gasoline, and Paint Removers (Naptha and Xylol) from Water Using (R)—N-Propyl-12-Hydroxyoctadecylammonium Chloride (12HSA3Cl)

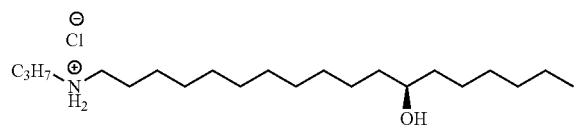

Low Molecular Weight Gelator Designated as 12HSA3Cl

Phase selective gelation in gasoline: Approximately 0.1 g (precise weight plus weight of gelator reported in Table 14) of gasoline was added to 1.8 g of D.C. (District of Columbia) tap water in a glass vial. Then, 60 mg of a solution of 3.6 wt % 12HSA3Cl in methanol (containing 2 mg of 12HSA3Cl) was added to the above gasoline-water mixture at 23° C. and the vial was observed overtime as noted in FIG. 55. After 40 h, the gasoline had been taken up completely in the 12HSA3Cl and formed an easily removable thick aggregate (FIG. 55 (IV G)). The gel was removed from the vial with a spatula and its surface was wiped quickly with a tissue to remove surface water. The weight of the gel (shown in FIG. 2 G) was determined immediately thereafter (Table 14).

Phase selective gelation in xylol: Approximately 0.1 g (precise weight plus weight of gelator reported in Table 1) of xylol (Parks) was added to 1.6 g of D.C. tap water in a glass vial. Then, 60 mg of a solution of 3.6 wt % 12HSA3Cl in methanol (containing 2 mg of 12HSA3Cl) was added to the above gasoline-water mixture at 23° C. and the vial was observed over time as noted in FIG. 55. After 40 h, the xylol had been taken up completely in the 12HSA3Cl and formed an easily removable thick aggregate (FIG. 55 (IV X)). The gel was removed from the vial with a spatula and its surface was wiped quickly with a tissue to remove surface water. The weight of the gel (shown in FIG. 56 X) was determined immediately thereafter (Table 14).

Phase selective gelation in Naptha: Approximately 0.1 g (precise weight plus weight of gelator reported in Table 1) of Naptha (VM-46, VM and P) was added to 1.8 g of D.C. tap water in a glass vial. Then, 65 mg of a solution of 3.6 wt % 12HSA3Cl in methanol (containing 2 mg of 12HSA3Cl) was added to the above gasoline-water mixture at 23° C. and the vial was observed over time as noted in FIG. 55. After 40 h, the Naptha had been taken up completely in the 12HSA3Cl and formed an easily removable thick aggregate (FIG. 55 (IV N)). The gel was removed from the vial with a spatula and its surface was wiped quickly with a tissue to remove surface water. The weight of the gel (shown in FIG. 56 N) was determined immediately thereafter (Table 14).

TABLE 14

% of recovery of gasoline, xylol and Naptha from water in the 12HSA3Cl.[a]

| Hydrocarbon liquid | Amount required for 100 % recovery (hydrocarbon plus gelator) | Recovered gel | % of recovery |
|---|---|---|---|
| Gasoline | 100.4 mg | 99.2 mg | 99 |
| Xylol | 102.0 mg | 101.2 mg | 99 |
| Naptha | 109.7 mg | 104.7 mg | 95 |

[a]The estimated error in the measurements is ±10%.

While exemplary articles and methods have been described in detail with reference to specific embodiments thereof, it will be apparent to those skilled in the art that various changes and modifications can be made, and equivalents employed without departing from the scope of the pending claims.

Each patent, patent application, publication, text and literature article/report cited or indicated herein is hereby expressly incorporated by reference in its entirety. In addition, the article "Robust Organogels from Nitrogen-Containing Derivatives of (R)-12-Hydroxystearic Acid as Gelators: Comparisons with Gels from Stearic Acid Derivatives" by V.

Ajay Mallia, Mathew George, Daniel L. Blair and Richard G. Weiss, published in *Langmuir,* 2009, 25 (15), pp 8615-8625, including the supporting documentation, is hereby expressly incorporated by reference in'its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

CITED REFERENCES (1) (a) Terech, P.; Weiss, R. G. *Chem. Rev.* 1997, 97, 3133 3159. (b) Shinkai, S.; Murata, K. 1. *Mater. Chenz.* 1998, 8, 485 495. (c) Abdallah, D. J.; Weiss, R. G. *Adv. Mater.* 2000, 12, 1237-1247. (d) van Esch, J. II.; Feringa, B. L. *Angell. Chem., Int.* 12(1.2000, 39, 2263 2266. (e) Saingeetha, N. M.; Maitra, U. *Chem. Soc. Rev.* 2005, 34, 821 836. (f) Weiss, R. G., Terech, P., Eds. *Molecular Gels. Materials with Self-Assembled Fibrillar Networks;* Springer: Dordrecht, The Netherlands, 2006. (g) George, M; Weiss, R. G. *Ace. Chem. Res.* 2006, 39, 489 497.

(2) van Esch, J. H.; Schoonbeek, F.; Loos, M. D.; Veen, E. M.; Kellog, R. M.; Feringa, B. L. In *Supramolecular Science. Where It IS and Where It Is Going;* Ungar, R., Dalcanale, E., Eds.; Kluwer Academic Publishers: The Netherlands, 1999; pp 233-259.

(3) Srivastava, S. P.; Saxena, A. K.; Tandon, R. S.; Shekher, V. *Fue1*1997, 76, 625 630.

(4) Abdallah, D. J.; Weiss, R. G. *Langmuir* 2000, 16, 352-355.

(5) Abdallah, D. J.; Sirchio, S. A.; Weiss, R. G. *Langmuir* 2000, 7558-7561.

(6) (a) Georg, M.; Weiss, R. G. 1. *Am. Chem. Soc.* 2001, 123, 10393 10394. (b) Ballabh, A.; Trivedi, D. R.; Dastidar, P *Chem. Mater.* 2006, 18, 3795 3800.

(7) (a) Marton, L.; McBain, J. W.; Vold, R. D. *J. Am. Chem. Soc.* 1941, 63, 1990 1993. (b) Zana, R. *Langmuir* 2004, 20, 5666 5668. (c) Novales, B.; Navilles, L.; Axelos, M.; Nallet, I.; Douliez, J.-P. *Langmuir* 2008, 24 62 68.

(8) Mieden-Gundert, G.; Klein, L.; Fischer, M.; Vogtle, F.; Ileuze, K.; Pozzo, J-L.; Vallier, M.; Fages, F. *Angell. Chem., Int. Ed.* 2001, 40, 3164 3166.

(9) Gaspar, L. J. M.; Baskar, G. 1. *Mater. Chem.* 2005, 15, 5144 5150.

(10) Lescanne, M.; Grondin, P.; D'Aleo, A.; Fages, F.; Pozzo, J-L.; Monval, O. M.; Reinheinicr, P; Collin, A. *Langmuir* 2004, 20, 3032-3041.

(11) Maskaev, A. K.; Manikovskaya, N. K.; Lendlel, I. V.; Fedorovskii, V. T.; Simurova, E. I.; Tcrcnt'eva, V. N. *Chem. Technol. Fuels Oils* 1971, 7, 109-112.

(12) (a) Terech, P.; Rodriguez, V.; Barnes, J. D.; Mckenna, Cr. B. *Langmuir* 1994, 10, 3406 3418. (b) Terech, P.; Patsquier, D.; Bordas, V.; Rossat, C. *Lingrnuir* 2000, /6, 4485 4494. (c) Tsau, J. S.; Ileller, J. P.; Prat ap, G. *Polym. Prepr.* 1994, 35, 737 738. (d) Tachihana, T.; Mori, T.; Ilori, K. *Bull. Chem. Soc. 1pn.* 1980, 53, 1714 1719. (e) Tachihana, T.; Mori, T.; Ilori, K. *Bull. Chem. Soc Jim.* 1981, 54, 73 80. (f) Tachibana, T.; Kitazawa, S.; Takeno, *Bull. Chem. Soc. Jpn.* 1970, 43, 2418-2421. (g) Tachibana, T.; Kambara, I I *Bull. Chem. Soc. Jpn.* 1969, 42, 3422-3424. (11) Tachibana, T.; Karribara, I I. *J. Chem. Soc.* 1965, 87, 3015 3016. (i) Terech, P. *Colloid Polym. Sci.* 1991, 269, 490 500.

(13) George, M.; Weiss, R. Cr. In *Molecular Gels. Material with Self Assembled Fibrillar Networks;* Weiss, R. G.; Teroch, P., Eds.; Springer: Dordrecht, The Netherlands, 2006; pp 449-551.

(14) Burrows, A. D. In *Structure and Bonding;* Mingos, D. M. P., Ed.; Springer-Verlag: Berlin, 2004; Vol. 108, pp 55-96.

(15) George, M.; Tan, Cl.; John, V. T.; Weiss, R. G. *Chem. Eur. J.* 2005, 11, 3243-3255.

(16) (a) Nowak, A. P.; Breedveld, V.; Pakstis, L.; Ozhas, B.; Pine, D. J.; Pochan, D.; Deming, T. J. *Nature* 2002, 417, 424-428. (b) Zhang, S.; Holmes, T.; Lockshin, C.; Rich, A. *Proc. Natl. Acad. Sci. U.S.A S.A.* 1993, 90, 3334 3338. (c) Rarriachandran, S.; Tseng, Y.; Yu, Y. B. *Biomacromolecules* 2005, 6, 1316 1321. (d) Xu, J.; Liu, Z. S.; Ethan, S. Z. *J. Am. Oil Chem. Soc.* 2008, 85, 285-290. (e) Kundu, S. K.; Matsunaga, T.; Yoshida, M.; Shibayarria, M. *J. Phys. Chem. B* 2008, 112, 11537-11541.

(17) Alexander, L. E. *X-ray Diffraction Methods in Polymer Science;* John Wiley &. Sons: New York, 1969; pp 102-104.

(18) Takahashi, A.; Sakai, M.; Kato, T. *Polym. J.* 1980, 12, 335 341.

(19) The transition between the opaque and clear gel states is reversible and first order according to DSC thermograms.

(20) Huang, X.; Weiss, R. G. *Tetrahedron* 2007, 63, 7375 7385.

(21) Scheiner, S. *Hydrogen Bonding: A Theoretical Perspective;* Oxford University Press: Now York, 1997; p 121.

(22) (a) Hirst, A. R.; Coates, I. A.; Boucheteau, T. R.; Miravet, J. F.; Escuder, B.; Castelletto, V.; Hai-inky, I. W.; Smith, D. K. *J. Am. Chem. Soc.* 2008, 130, 9113 9121. (b) Mukkamala, R.; Weiss, R. G. *Langmuir* 1996, 12, 1474 1482. (c) Lu, L.; Cocker, T. M.; Bachman, R. E.; Weiss, R. G. *Langmuir* 2000, 16, 20-34.

(23) Ahdallah, D. T. Lu, L.; Weiss, R. G. *Chem. Mater.* 1999, 11, 2907-2911

(24) George, M.; Weiss, R. G. *Langmuir* 2002, 18, 7124 7135.

(25) (a) Lin, Y.; Kachar, B. Weiss, R. G. *J. Am. Chem. Sco.* 1989, 111, 5542 5551. (h) Furman, I.; Weiss, R. G. *Langmuir* 1993, 9, 2084 2088.

(26) Ahdallah, D. J.; Weiss, R. G. *Chem. Mater.* 2002, 14, 406 41.3.

(27) Davey, R. J.; Garside, *J. From Molecules to Crystallizers;* Oxford University Press: New York, 2000; Chapter 2 and references cited therein.

(28) (a) Liu, X. Y.; Sawant, P. D. *Adv. Mater.* 2002, 14, 421 426. (b) Liu, X. Y.; Sawant, P. D. *Appl. Phys. Lett.* 2001, 19, 3518 3520.

(29) Rogers, M. A.; MLtrangoni, A. G. *Cry.st. Growth Des.* 2008, 8, 4596 4601.

(30) Ostuni, E.; Kamaras, P.; Weiss, R. Cr. *Angew. Chem., Int. Ed.* 1996, 35, 1324 1326.

(31) Using.JA DE software from Materials Data Inc., Release 5.0.35 (SPS), Livermore, Calif.

(32) (a) Using Chem 3D Ultra software (Cambridge Soft Corporation) and adding the van der Waals radii of the terminal atoms according to (b) Bondi, A *J. Phys. Chem.* 1964, 68, 441-451.

(33) (a) Lescanne, M.; Grondin, P.; D'Aleo, A.; Fages, F.; Pozzo, J-L.; Monval, O. M.; Reinheimer, P.; Collin, A. *Langmuir* 2004, 20, 3032 3041. (h) Brinksma, J.; Fedi-lull, B. L.; Kellog, R. M.; Vrecker, R.; Esch, J. V. *Langmuir* 2000, 16, 9249 9255. (c) Huang, X.; Raghavan, S. R.; Terech, P.; Weiss, R. G. J. *Aril. Chem. Soc.* 2006, 128, 15341-15352. (d) Shirakawa, M.; Fujita, N.; Shinkai, S. *J. Am. Chem. Soc.* 2005, 127, 4164 4165. (c) Perccc, V.;

Pcterca, M.; Yurchcnko, M. E.; Rudick, J. G.; Heiney, P. A. *Chem.-Eur. J.* 2008, 14, 909-918.

(34) (a) Abdallah, D. J.; Bachman, R. E.; Perlstein, J.; Weiss, R. Cr. *J. Phys. Chem. B* 1999, 103, 9269 9278. (b) Abdallah, D. J.; Robertson, A.; Hsu, H. F.; Weiss, R. G. 1. *Arn. Chem..Soc.* 2000, 122, 3053-3062.

(35) Shank Lir, R.; Ghosh, T. K.; Spontak, R. J. *Soft Mauer* 2007, 3, 1116-1129.

What is claimed:

1. A composition comprising: (a) a compound of formula (IV):

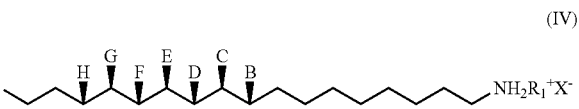

wherein
- $R_1$ is an alkyl group of the formula $C_nH_{2n+1}$, an aryl group or hydrogen,
- n is an integer from 1 to 6,
- X is an anion, and
- at least one of B, C, D, E, F, G and H is a hydroxyl group and the others are hydrogen,
- and the compound is in the (R) form,
- and either (b), (c) or (d), namely: (b) an active pharmaceutical ingredient and a pharmaceutically acceptable carrier; (c) a food; or (d) a cosmetically acceptable ingredient and a cosmetically acceptable carrier.

2. The composition of claim 1, wherein the anion is selected from the group consisting of chlorine, bromine, iodine, nitrate, boron trifluoride, acetate, nonanoate and oxalate.

* * * * *